United States Patent
Shirwaiker et al.

(10) Patent No.: US 12,179,194 B2
(45) Date of Patent: Dec. 31, 2024

(54) ULTRASOUND-BASED PATTERNING OF PARTICLES AND CELLS WITHIN FLUID MATRICES

(71) Applicant: North Carolina State University, Raleigh, NC (US)

(72) Inventors: Rohan Shirwaiker, Raleigh, NC (US); Parth Chansoria, Raleigh, NC (US); Lokesh Narayanan, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 958 days.

(21) Appl. No.: 17/207,057

(22) Filed: Mar. 19, 2021

(65) Prior Publication Data

US 2021/0260578 A1   Aug. 26, 2021

Related U.S. Application Data

(63) Continuation of application No. PCT/US2019/056859, filed on Oct. 18, 2019.
(Continued)

(51) Int. Cl.
*B33Y 40/00* (2020.01)
*B01L 3/00* (2006.01)
(Continued)

(52) U.S. Cl.
CPC ..... *B01L 3/50273* (2013.01); *B01L 3/502761* (2013.01); *B33Y 40/00* (2014.12);
(Continued)

(58) Field of Classification Search
CPC ....... B33Y 40/00; C12N 5/0062; C12N 13/00
See application file for complete search history.

(56) References Cited

U.S. PATENT DOCUMENTS 6,936,151 B1   8/2005   Lock
7,373,805 B2   5/2008   Hawkes et al.
(Continued)

FOREIGN PATENT DOCUMENTS

WO   2014029505 A1   2/2014
WO   2018022513 A1   2/2018

OTHER PUBLICATIONS

Bouyer et al., (2015) A bio-acoustic levitational (BAL) Assembly method for engineering of multilayered, 3D brain-like constructs, using human embryonic stem cell derived neuro-progenitors. Advanced Materials, 28(1) pp. 161-167 (Year: 2015).*
(Continued)

*Primary Examiner* — Kara D Johnson
(74) *Attorney, Agent, or Firm* — NK Patent Law

(57) ABSTRACT

Method of ultrasound-assisted 3D bioprinting includes depositing a bioink fluid matrix containing a suspension of cells into a chamber comprising two piezo transducers on opposing ends of the chamber. The method further includes vibrating the piezo transducers to generate longitudinal bulk acoustic waves within the bioink fluid matrix such that waves from opposing piezo transducers superimpose to form a standing bulk acoustic wave to drive the cells to cluster and align along one or more nodes or nodal planes formed within the bioink fluid matrix at points of intersection of the standing bulk acoustic wave. The nodes or nodal planes are spaced apart from each other by a distance equaling half a wavelength of the standing bulk acoustic wave. The nodes or nodal planes further mimic a contour of the vibrating surfaces of the piezo transducers.

21 Claims, 28 Drawing Sheets

Related U.S. Application Data

(60) Provisional application No. 62/747,789, filed on Oct. 19, 2018.

(51) Int. Cl.
  *C12N 5/00* (2006.01)
  *C12N 13/00* (2006.01)

(52) U.S. Cl.
  CPC ........... *C12N 5/0062* (2013.01); *C12N 13/00* (2013.01); *B01L 2200/0668* (2013.01); *B01L 2400/0436* (2013.01); *B01L 2400/0439* (2013.01)

(56) References Cited

U.S. PATENT DOCUMENTS

| | | |
|---|---|---|
| 8,863,958 B2 | 10/2014 | Kaduchak et al. |
| 8,932,520 B2 | 1/2015 | Goddard et al. |
| 9,645,080 B2 | 5/2017 | Matula et al. |
| 9,663,756 B1 | 5/2017 | Lipkens et al. |
| 9,738,867 B2 | 8/2017 | Lipkens et al. |
| 2014/0008307 A1 | 1/2014 | Guldiken et al. |
| 2015/0084232 A1 | 3/2015 | Rutz et al. |
| 2017/0304746 A1 | 10/2017 | Lipkens et al. |
| 2018/0117909 A1 | 5/2018 | Foresti et al. |

OTHER PUBLICATIONS

Greenhall et al., (2013) Continuous and unconstrained manipulation of micro-particles using phase-control of bulk acoustic waves. Applied Physics Letters, 103, 074103 (Year: 2013).*

Qiu et al., (Enhancement of acoustic energy density in bulk-wave-acoustophoresis devices using side actuation. Physical Review Applied, 17, 044043 (Year: 2022).*

Ravula et al., (2008) Characterization and modeling of a bulk acoustic wave particle focusing device. 2008 IEEE International Frequency Control Symposium, Honolulu, HI, USA, 2008, pp. 35-38, doi: 10.1109/FREQ.2008.4622951 (Year: 2008).*

ISA/US; International Search Report and Written Opinion for International Patent Application No. PCT/US19/56859 dated Mar. 3, 2020, 15 pages.

WIPO; International Preliminary Report on Patentability for International Patent Application No. PCT/US19/56859 dated Apr. 29, 2021, 12 pages.

* cited by examiner

| | 0.71 MHz | 1 MHz | 1.5 MHz | 2 MHz |
|---|---|---|---|---|
| 100 mVpp | 0.24 pN | 3.4 pN | 276 pN | 6 pN |
| 200 mVpp | 0.9 pN | 13 pN | 1106 pN | 24.3 pN |

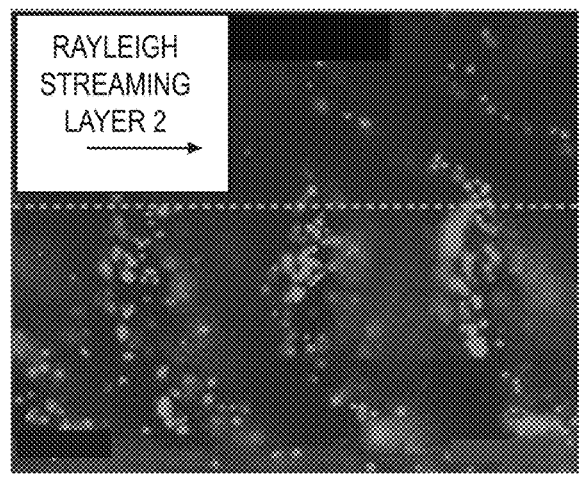
FIG. 12d
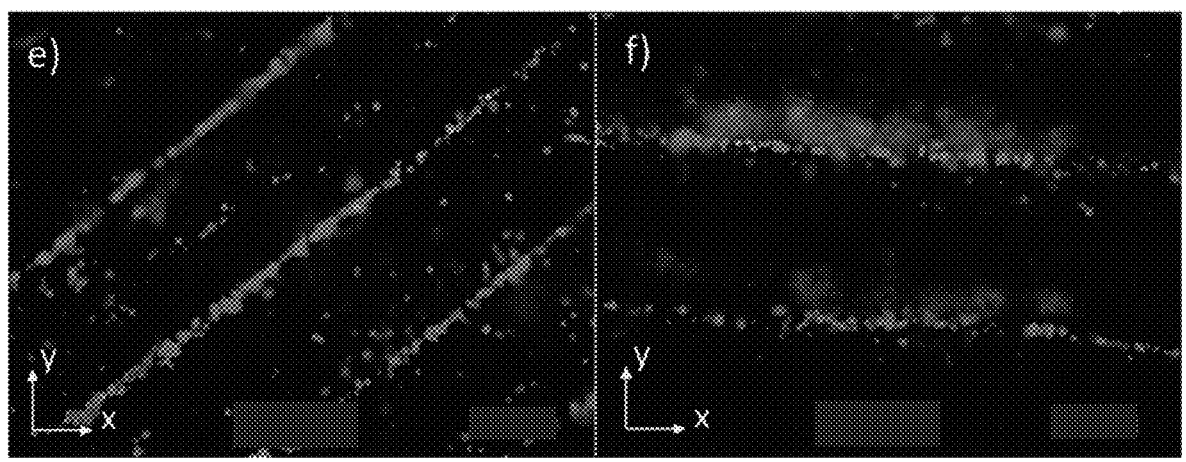
ZONE I
FIG. 12e
ZONE II
FIG. 12f
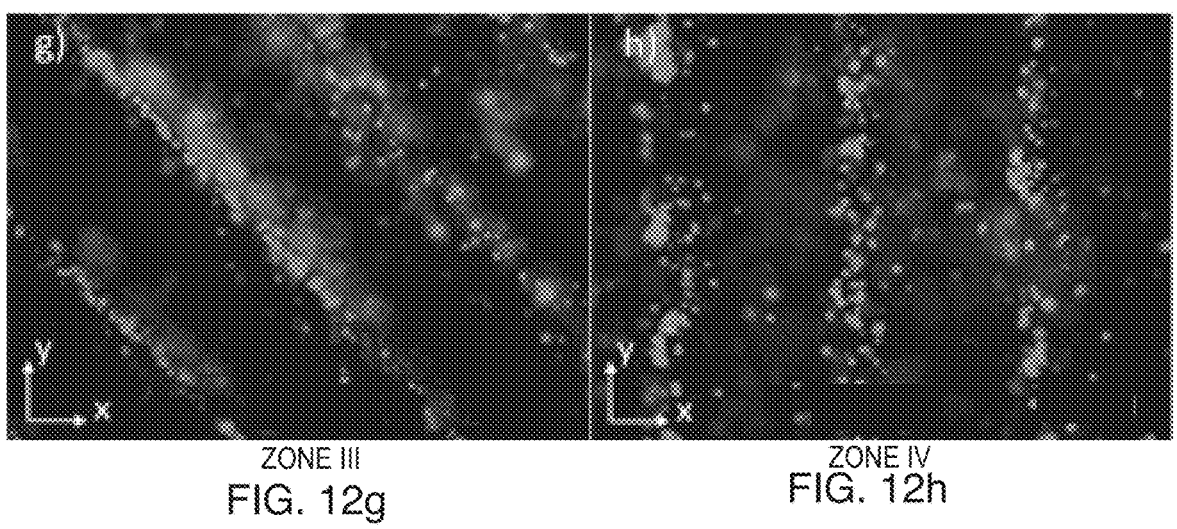
ZONE III
FIG. 12g
ZONE IV
FIG. 12h

ULTRASOUND-BASED PATTERNING OF PARTICLES AND CELLS WITHIN FLUID MATRICES

CROSS-REFERENCE TO RELATED APPLICATIONS

This application is a continuation of PCT Patent Application No. PCT/US2019/056859 entitled "ULTRASOUND-BASED PATTERNING OF PARTICLES AND CELLS WITHIN FLUID MATRICES," which was filed on Oct. 18, 2019, which claims priority to U.S. Provisional Patent Application No. 62/747,789 filed on Oct. 19, 2018, the entire contents of which are incorporated by reference herein.

STATEMENT OF FEDERALLY FUNDED RESEARCH

This invention was made with government support under grant number 1,652,489 awarded by the National Science Foundation. The government has certain rights to this invention.

TECHNICAL FIELD

The present invention relates generally to the field of manufacturing of a polymer matrix with anisotropic properties, and particularly to a non-contact acoustics-based manufacturing method for patterning of additives such as nanoparticles and cells within a polymer matrix to create composites including engineered tissues with preferentially anisotropic properties.

BACKGROUND

Material anisotropy is a physical design of natural objects. Manipulating of a physical design of an object to adjust the anisotropy level within a polymer matrix can create a specimen exhibiting desired mechanical loading and energy absorption characteristics. Engineering materials such as long fiber reinforced composites are widely used for such purposes due to their high strength to weight (S/W) ratios. Short fiber composites, on the other hand, are much easier to manufacture, but they lack the advantages resulting from high S/W ratios provided by long fibers. A preferential alignment of short fibers within a polymer matrix has the potential to greatly enhance specific strengths (e.g., compression, tensile) and/or stiffness of composites manufactured from short fibers.

Many human body tissues demonstrate anisotropy in the organization of their cells and extracellular matrix (ECM) fibers, and anisotropy is essential to their primary functions within the human body. Human body tissues created with a predetermined alignment of cells and human body tissues created with a predetermined alignment of cells and micro-scale or nano-scale fiber combinations can produce soft tissues that can help heal highly prevalent injuries.

Current surgical treatments including polymer/metal implants in orthopedics have several limitations and thus have significant scope for improvement. Accordingly, opportunities exist for improved approaches for patterning of additives such as nanoparticles and cells within a polymer matrix to create composites including engineered tissues with predetermined anisotropic properties.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

Disclosed herein is a method of ultrasound-assisted 3D bioprinting. According to various embodiments, the method comprises: depositing a bioink fluid matrix containing a suspension of cells or particles into a chamber comprising a piezo transducer and a reflector positioned on opposing ends of the chamber; vibrating the piezo transducer to generate longitudinal bulk acoustic waves within the bioink fluid matrix such that waves emanating from the piezo transducer and reflected waves from the reflector superimpose to form a standing bulk acoustic wave; and driving the cells or particles to cluster and align along one or more nodes or nodal planes formed within the bioink fluid matrix at points of intersection of the standing bulk acoustic wave to form a construct. The nodal planes are spaced apart from each other by a distance equaling half a wavelength of the standing bulk acoustic wave. The nodes or nodal planes mimic a contour of the vibrating surfaces of the piezo transducer or the reflector, or organize a pattern determined using computational modeling.

According to one or more embodiments, the method further comprises solidifying the bioink fluid matrix using one or more of: chemical, heat, and light treatment to entrap the aligned cells or particles in place.

According to one or more embodiments, the method further comprises gelling the bioink fluid matrix using one or more of: chemical, heat, and light treatment to entrap the aligned cells or particles in place.

According to one or more embodiments, a chamber shape and a number of piezo transducers is configured based on a predetermined pattern of cell arrangement.

According to one or more embodiments, the method further comprises providing additional piezo transducers wherein a control algorithm vibrates the piezo transducers in a specified sequence to obtain a predetermined pattern of cell arrangement.

According to one or more embodiments, the spacing between the piezo transducers is equal to an integer multiple of half the wavelength of the standing bulk acoustic wave.

According to one or more embodiments, the spacing between the piezo transducers is configured to accommodate a size of a construct of cell arrangement to be formed between the piezo transducers.

According to one or more embodiments, spacing between the piezo transducers is correlated to a frequency of the standing bulk acoustic wave.

According to one or more embodiments, the method further comprises increasing a frequency of the standing bulk acoustic wave to decrease a width of the nodal planes.

According to one or more embodiments, the method further increasing a voltage amplitude supplied to the transducers to decrease a width of the nodes or nodal planes.

According to one or more embodiments, the method further comprises increasing excitation duration or actuation duration of the piezo transducer to decrease a width of the nodes or nodal planes.

According to one or more embodiments, the method further comprises delaying a crosslinking initiation or a gelling initiation within the chamber to reduce a width of the nodes or nodal planes.

According to one or more embodiments, the method further comprises increasing a frequency of the standing bulk acoustic wave to decrease spacing between adjacent nodal planes.

According to one or more embodiments, the piezo transducers are electrically coupled to an intermediate high frequency radio frequency power amplifier.

According to one or more embodiments, the piezo transducer is electrically coupled to one or more of a function generator and a signal generator.

According to one or more embodiments, the chamber has a physical structure configured based on a shape of a pre-determined construct of cell arrangement.

According to one or more embodiments, the chamber is rectangular shaped with the piezo transducers located at opposing sides of the rectangle.

According to one or more embodiments, a dispenser of the bioink fluid matrix and an apparatus for orienting the piezo transducer and an apparatus for gelling or solidifying the suspension of cells or particles by one or more of a crosslinking process and a gelling process are integrated within a 3D-printing head.

According to one or more embodiments, an apparatus for orienting the piezo transducer forms part of a separate 3D-printing head.

According to one or more embodiments, the piezo transducers are mounted on a rotating bracket, wherein the method further comprises rotating the rotating bracket to align the piezo transducers in a predetermined orientation.

According to one or more embodiments, the method further comprises cross-linking the aligned cells or particles nodes or nodal planes by one or more of a gelling process and a solidifying process.

According to one or more embodiments, the bioink fluid matrix is a homogenous suspension of one or more of: cells, proteins, micro particles, nano-particles, micro-fibers and nano-fibers.

According to one or more embodiments, spacing between the piezo transducer and the reflector is equal to an integer multiple of half the wavelength of the standing bulk acoustic wave.

According to one or more embodiments, the method further comprises transferring the chamber comprising a completed construct with aligned cells or particles to an incubator to mature the construct over a predetermined time period under predetermined environmental conditions.

Disclosed herein is a method of ultrasound-assisted 3D bioprinting. According to one or more embodiments, the method comprises: depositing a bioink fluid matrix containing a suspension of cells or particles into a chamber, the chamber comprising two piezo transducers on opposing ends of the chamber; vibrating the piezo transducers to generate longitudinal bulk acoustic waves within the bioink fluid matrix such that waves from opposing piezo transducers superimpose to form a standing bulk acoustic wave; and driving the cells or particles to cluster and align along one or more nodes or nodal planes formed within the bioink fluid matrix at points of intersection of the standing bulk acoustic wave to form a construct. The nodes or nodal planes are spaced apart from each other by a distance equaling half a wavelength of the standing bulk acoustic wave. The nodes mimic a contour of the vibrating surfaces of the piezo transducers, or a pattern determined using computational modeling.

According to one or more embodiments, spacing between the piezo transducers is equal to an integer multiple of half the wavelength of the standing bulk acoustic wave.

According to one or more embodiments, the method further comprises transferring the chamber comprising a completed construct with aligned cells or particles to an incubator to mature the construct over a predetermined time period under predetermined environmental conditions.

Disclosed herein is a method of ultrasound-assisted 3D bioprinting. According to one or more embodiments, the method comprises: depositing a bioink fluid matrix containing a suspension of cells into a chamber comprising a piezo transducer and a reflector positioned on opposing ends of the chamber; vibrating the piezo transducer to generate longitudinal bulk acoustic waves within the bioink fluid matrix such that waves emanating from the piezo transducer and reflected waves from the reflector superimpose to form a standing bulk acoustic wave; and driving the cells to cluster and align along one or more nodes or nodal planes formed within the bioink fluid matrix at points of intersection of the standing bulk acoustic wave to form a construct. The nodal planes are spaced apart from each other by a distance equaling half a wavelength of the standing bulk acoustic wave. The nodes or nodal planes mimic a contour of the vibrating surfaces of the piezo transducer or the reflector, or organize a pattern determined using computational modeling.

According to one or more embodiments, the method further comprises transferring the chamber comprising a completed construct with aligned cells to an incubator to mature the construct over a predetermined time period under predetermined culture conditions.

Disclosed herein is a method for aligning particles into predetermined patterns within a fluid matrix. According to one or more embodiments, the method comprises: depositing a homogeneous fluid matrix containing a suspension of particles into a chamber comprising a piezo transducer and a reflector positioned on opposing ends of the chamber; vibrating the piezo transducer to generate longitudinal bulk acoustic waves within the fluid matrix such that waves from the piezo transducer superimpose to form a standing bulk acoustic wave; and driving the particles to cluster and align along one or more nodes or nodal planes formed within the fluid matrix at points of intersection of the standing bulk acoustic wave to form a construct. The nodes or nodal planes are spaced apart from each other by a distance equaling half a wavelength of the standing bulk acoustic wave. The nodes or nodal planes mimic a contour of the vibrating surface of the piezo transducer, the reflector, or organize in other patterns determined through computational modeling.

According to one or more embodiments, spacing between the piezo transducer and the reflector is equal to an integer multiple of half the wavelength of the standing bulk acoustic wave.

According to one or more embodiments, the method further comprises transferring the chamber comprising a completed construct with particles to an incubator to mature the construct over a predetermined time period under predetermined environmental conditions.

Disclosed herein is a method of ultrasound-assisted 3D bioprinting a tissue construct. According to one or more embodiments, the method further comprises: providing a chamber comprising at least two piezo transducer-reflector pairs, wherein each piezo transducer and a corresponding reflector are positioned on opposing ends of the chamber, wherein each piezo transducer-reflector pair is angled relative to each of another piezo transducer-reflector pair; depositing a bioink fluid matrix containing a suspension of cells or particles into the chamber; vibrating a first piezo transducer at a first frequency to generate longitudinal bulk acoustic waves within the bioink fluid matrix such that waves emanating from the first piezo transducer and reflected waves from an opposing reflector superimpose to form a standing bulk acoustic wave to drive the cells or particles to cluster and align along one or more nodes or nodal planes formed within the bioink fluid matrix at points where an amplitude of the standing bulk acoustic wave is zero, and initiating crosslinking of the cells or particles aligned at the one or more nodes to retain the cells or particles in position to form a first layer of a tissue construct; and, vibrating a second piezo transducer at a second frequency to generate longitudinal bulk acoustic waves within the bioink fluid matrix such that waves emanating from the second piezo transducer and waves reflected from an opposing reflector superimpose to form a standing bulk acoustic wave to drive the cells or particles to cluster and align along one or more nodes or nodal planes formed within the bioink fluid matrix at points where an amplitude of the standing bulk acoustic wave is zero, and initiating crosslinking of the cells or particles aligned at the one or more nodes or nodal planes to retain the cells or particles in position to form a second layer of the tissue construct.

According to one or more embodiments, the method further comprises transferring the chamber comprising a completed tissue construct with aligned cells or particles to an incubator to mature the tissue construct over a predetermined time period under predetermined culture or environmental conditions.

Disclosed herein is a method of ultrasound-assisted 3D bioprinting a tissue construct. According to one or more embodiments, the method further comprises: providing a chamber comprising at least two pairs of opposing piezo transducers such that each piezo transducer in a pair is positioned on opposing ends of the chamber, wherein each pair of opposing piezo transducers is angled relative to each of the other pair of piezo transducers; depositing a bioink fluid matrix containing a suspension of cells or particles into the chamber; vibrating a first pair of piezo transducers at a first frequency to generate longitudinal bulk acoustic waves within the bioink fluid matrix such that waves emanating from opposing piezo transducers superimpose to form a standing bulk acoustic wave to drive the cells or particles to cluster and align along one or more nodes or nodal planes formed within the bioink fluid matrix at points where an amplitude of the standing bulk acoustic wave is zero, and initiating crosslinking of the cells or particles aligned at the one or more nodes to retain the cells or particles in position to form a first layer of a tissue construct; and, vibrating a second pair of piezo transducers at a second frequency to generate longitudinal bulk acoustic waves within the bioink fluid matrix such that waves emanating from opposing piezo transducers superimpose to form a standing bulk acoustic wave to drive the cells or particles to cluster and align along one or more nodes or nodal planes formed within the bioink fluid matrix at points where an amplitude of the standing bulk acoustic wave is zero, and initiating crosslinking of the cells or particles aligned at the one or more nodes or nodal planes to retain the cells or particles in position to form a second layer of the tissue construct.

According to one or more embodiments, the method further comprises transferring the chamber comprising a completed tissue construct with aligned cells or particles to an incubator to mature the tissue construct over a predetermined time period under predetermined culture or environmental conditions.

Disclosed herein is a method of ultrasound-assisted 3D bioprinting a tissue construct. According to one or more embodiments, the method further comprises: providing a chamber comprising at least three piezo transducer-reflector pairs, wherein each piezo transducer and a corresponding reflector are on opposing ends of the chamber, wherein each piezo transducer-reflector pair is angled relative to each of another piezo transducer-reflector pair; depositing a bioink fluid matrix containing a suspension of cells into the chamber; vibrating a first piezo transducer at a first frequency to generate longitudinal bulk acoustic waves within the bioink fluid matrix such that waves emanating from the first piezo transducer and reflected waves from an opposing reflector superimpose to form a standing bulk acoustic wave to drive the cells to cluster and align along one or more nodes or nodal planes formed within the bioink fluid matrix at points where an amplitude of the standing bulk acoustic wave is zero, and initiating crosslinking of the cells aligned at the one or more nodes to retain the cells in position to form a first layer of a tissue construct; vibrating a second piezo transducer at a second frequency to generate longitudinal bulk acoustic waves within the bioink fluid matrix such that waves emanating from the second piezo transducer and waves reflected from an opposing reflector superimpose to form a standing bulk acoustic wave to drive the cells to cluster and align along one or more nodes or nodal planes formed within the bioink fluid matrix at points where an amplitude of the standing bulk acoustic wave is zero, and initiating crosslinking of the cells aligned at the one or more nodes or nodal planes to retain the cells in position to form a second layer of the tissue construct; vibrating a third piezo transducer at a third frequency to generate longitudinal bulk acoustic waves within the bioink fluid matrix such that waves emanating from the third piezo transducer and reflected waves from an opposing reflecting surface superimpose to form a standing bulk acoustic wave to drive the cells to cluster and align along one or more nodes or nodal planes formed within the bioink fluid matrix at points where an amplitude of the standing bulk acoustic wave is zero, and initiating crosslinking of the cells aligned at the one or more nodes or nodal planes to retain the cells in position to form a third layer of the tissue construct.

According to one or more embodiments, the method further comprises forming subsequent layers above the third layer of the tissue construct.

According to one or more embodiments, the method further comprises: curing the cells of the first layer in place followed by depositing the bioink fluid matrix containing a suspension of cells into the chamber to form the second layer; curing the cells of the second layer in place followed by depositing the bioink fluid matrix containing a suspension of cells into the chamber to form the third layer; curing the cells of the third layer in place followed by depositing the bioink fluid matrix containing a suspension of cells into the chamber to form subsequent layers.

According to one or more embodiments, the cells of the layers are entrapped in place using a vat photopolymerization process.

According to one or more embodiments, the method further comprises transferring the chamber comprising a completed tissue construct with aligned cells to an incubator to mature the tissue construct over a predetermined time period under predetermined culture conditions.

According to one or more embodiments, a first piezo transducer-reflector pair is angled is assigned a 0° orientation, a second piezo transducer-reflector pair is angled is assigned a 45° orientation, and third piezo transducer-reflector pair is angled is assigned a 90° orientation.

According to one or more embodiments, the cells in the first layer are aligned along a 0°-180° orientation, the cells in the second layer are aligned along a 0°-180° orientation, and the cells in the third layer are aligned along a 0°-180° orientation.

According to one or more embodiments, the method further comprises adjusting a vibrating frequency or amplitude of at least on the first, second, and third piezo transducers to alter pressure amplitude at and resulting locations of the one or more nodes or nodal planes.

According to one or more embodiments, the cells comprise human adipose-derived stem cells (hASC) or human osteosarcoma cells (MG63).

According to one or more embodiments, initiating the crosslinking of the cells comprises a gelling process, wherein the gelling process comprises one or more of UV curing, chemical crosslinking, and thermal crosslinking.

According to one or more embodiments, initiating the crosslinking of the cells comprises use of a selective ultraviolet (UV) curing process.

According to one or more embodiments, the method further comprises transferring the chamber comprising a completed single or multi-layered construct with aligned cells to an incubator to mature the construct over a predetermined time period under a predetermined culture condition.

According to one or more embodiments, the nodes or nodal planes may mimic a contour of the vibrating surfaces of the piezo transducers, or can be other patterns generated due to the wave mechanics within the chamber that can be estimated using computational modeling of the wave mechanics within the chamber.

According to one or more embodiments, the nodes or nodal planes are spaced apart from each other by a distance equaling half a wavelength of the standing bulk acoustic wave. The nodes or nodal planes may mimic a contour of the vibrating surfaces of the piezo transducers, or can be other patterns generated due to the wave mechanics within the chamber that can be estimated using computational modeling of the wave mechanics within the chamber.

According to one or more embodiments, the method further includes solidifying the bioink fluid matrix using one or more of: chemical, heat, and light treatment to entrap the organized cells in place.

According to one or more embodiments, a chamber shape and a number of piezo transducers or transducer-reflector pairs are configured based on a predetermined pattern of cell arrangement.

According to one or more embodiments, the method further includes increasing the frequency of the standing bulk acoustic wave to decrease the width of the nodes or nodal planes.

According to one or more embodiments, the method further includes increasing the voltage amplitude supplied to the transducers to decrease the width of the nodes or nodal planes.

According to one or more embodiments, the method further includes increasing the duration of excitation of the transducers to decrease the width of the nodes or nodal planes.

According to one or more embodiments, the piezo transducers are electrically coupled to a function generator.

According to one or more embodiments, the chamber is rectangular shaped with one piezo transducer and a reflector located at opposing sides of the rectangle.

According to one or more embodiments, the bioink fluid matrix is a homogenous suspension of cells or particles within a fluid matrix.

According to one or more embodiments, the bioink fluid matrix is a homogenous suspension of other biologically relevant materials such as collagen fibrils within a fluid matrix.

According to one or more embodiments, each of the cells of first, second and third layers are cured in place using a chemical crosslinking process.

BRIEF DESCRIPTION OF THE DRAWINGS

FIG. 21(a) illustrates the cross-patterning ultrasound alignment chamber that contains orthogonally arranged transducer-reflector pairs; FIG. 21(b) illustrates a schematic representation of the SBAW generated due to transducer excitation; FIG. 21(c) illustrates the bioink being printed as adjacent strands (blue lines depict that rectilinear pattern of deposition) into the chamber pre-filled with PBS buffer to constitute the first layer of the construct; FIG. 21(d) illustrates transducer #1, when excited using a sinusoidal voltage signal; FIG. 21(e) illustrates the alginate being gradually crosslinked by introducing the crosslinker ($CaCl_2$) to entrap the aligned cells within the first layer; FIG. 21(g) illustrates transducer #2, when excited using a sinusoidal voltage signal; and, FIG. 21(h) illustrates the crosslinker (CaCl₂) being introduced to gradually crosslink the second alginate layer while entrapping the aligned cells, as provided in accordance with some embodiments of the presently disclosed subject matter.

DETAILED DESCRIPTION

Figure 1:
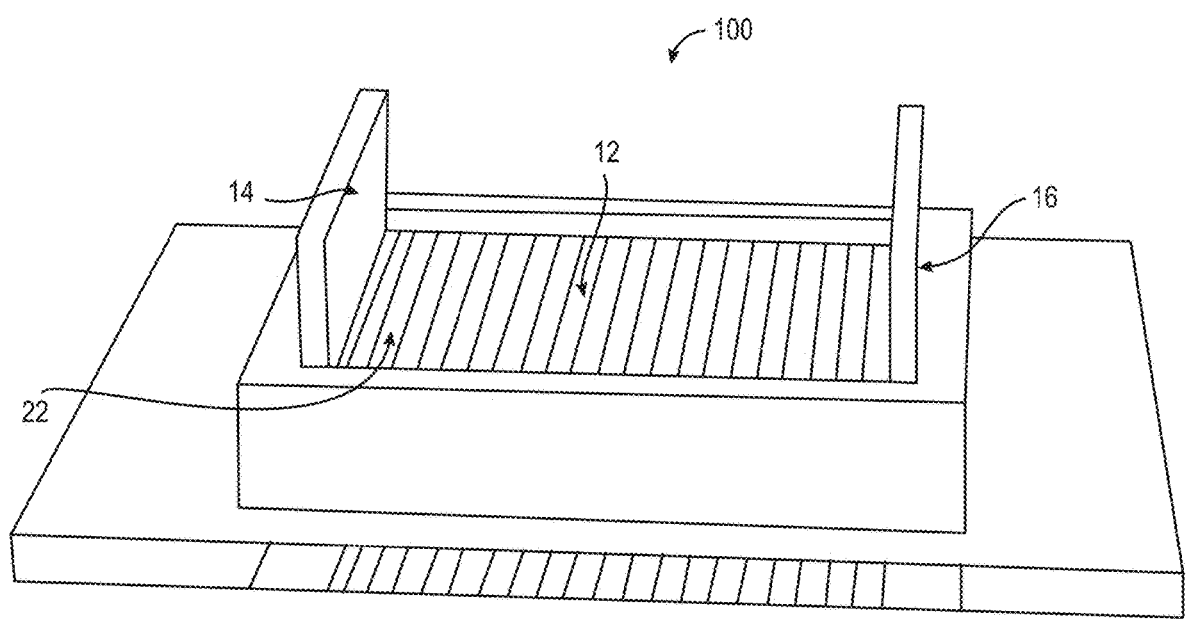
FIG. 1 illustrates a perspective view of an ultrasound-assisted 3D bioprinting device, as provided in accordance with some embodiments of the presently disclosed subject matter.

The following description and drawings are illustrative and are not to be construed as limiting. Numerous specific details are described to provide a thorough understanding of the disclosure. However, in certain instances, well-known or conventional details are not described in order to avoid obscuring the description. Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and is not intended to further limit the scope and meaning of the disclosure or of any exemplified term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

Biofabrication processes including bioprinting have gained prominence over the last decade because of their ability to incorporate living cells within the process of creating engineered tissue constructs. However, use of biofabrication technology to achieve native soft tissue-specific cellular organization is still in its infancy. While a majority of the current processes allow the recapitulation of the patient-specific macro-scale three-dimensional (3D) geometry of the tissue under consideration, they lack the ability to align cells into controlled spatial patterns.

Musculoskeletal soft tissues such as ligaments, tendons and knee menisci are characterized by unique organization of their cellular and extracellular constituents, which is central to their primary functions. For example, the cells and collagen fibers of ligaments and tendons, which primarily experience uniaxial tensile loads, are generally well-aligned along the direction of tensile loading. Likewise, the predominantly circumferential organization of collagen bundles and cells in the semilunar wedge-shaped menisci allow it to resist hoop stresses experienced in the knee joint. Such structure-function relationships are also evident in other types of soft tissues including cardiac tissue, conical stroma, liver tissue, vasculature, and intestines. Unfortunately, soft tissue injuries are highly prevalent (e.g., over a million annual incidences of anterior cruciate ligament and meniscus injuries), and current treatments including surgical repair, allo or autografts and metal-polymer implants have limitations. Hence, investigation and development of engineered tissue alternatives has become relevant.

Biofabrication processes including bioprinting have gained prominence over the last decade because of their ability to incorporate living cells within the process of creating engineered tissue constructs. However, use of biofabrication technology to achieve native soft tissue-specific cellular organization is still in its infancy. While a majority of the current processes allow the recapitulation of the patient-specific macro-scale three-dimensional (3D) geometry of the tissue under consideration, they lack the ability to align cells into controlled spatial patterns. The homogenous distribution of cells throughout the bulk constructs subsequently leads to an unorganized cell-secreted extracellular matrix (ECM) network as the constructs mature, which is undesirable.

Several biological and engineering applications of composites require very specific organization of additives/reinforcements (cells, proteins, micro/nano-particles/fibers etc.) within the matrix. For example, in tissues such as ligaments and tendons, the cells and cell-secreted extracellular matrix (ECM) proteins are aligned uniaxially, while in the knee meniscus, these are arranged circumferentially and radially in an orthogonal array. Such anisotropic organization has a direct bearing on the function performed by the tissue.

Disclosed herein a new non-contact acoustics-based manufacturing method for patterning of additives and/or reinforcements such as cells, proteins, micro particles, nano-particles, fibers and similar other items in order to create composites with preferential anisotropic properties. These additives and/or reinforcements are henceforth alternately referred to as "particles" within the matrix. In other words, the term "particles" as used herein refers to items such as cells, proteins, micro particles, nano-particles, micro-fibers, nano-fibers, and similar other items.

According to various embodiments of the presently disclosed subject matter, fluid matrix-particle suspension is deposited using conventional depositing techniques into a chamber designed to resemble the shape of the desired construct. Once the transducers are activated and form the standing bulk acoustic wave (SBAW) and the additives and/or reinforcements such as cells, proteins, micro particles, nano-particles, fibers and similar other item have aligned, the fluid matrix is solidified/gelled using chemical, heat, or light-based crosslinking methods to entrap the aligned particles in place—primarily for uniaxial patterns. The manufacturing may be undertaken either as a single bulk or in layers at a time. In various embodiments, the chamber shape and number of transducers can be customized to achieve more complex non-uniaxial patterns. Using a control algorithm, transducers can be powered in a predetermined sequence to obtain complex patterns as needed. Further, at least in one embodiment, fluid dispensing mechanism and acoustic alignment apparatus are integrated into, and form part of, an integrated 3D-printing head. The acoustic apparatus can consist of a rotating bracket onto which pair of transducers (or a transducer and a transducer-reflector) is mounted. In a continuous process, the fluid-particle suspension may be deposited, then aligned by the acoustic apparatus, and subsequently cross-linked. Distance between transducers can be adjusted to accommodate size of construct in between.

Accordingly, disclosed herein are methods, devices, and systems for non-contact acoustics-based manufacturing method for patterning of additives/reinforcements within a polymer matrix to create composites with preferentially anisotropic properties. Embodiments of the methods as described herein can allow for creation of cells, growth additives and similar other substances within the biomaterial matrix in desired alignments that imitate natural tissue. Embodiments of the methods as described herein can advantageously allow the growth of tissues such as MCL (medical collateral ligament) and anterior cruciate ligament (ACL), tendons, knee meniscus, cardiac tissue, corneal stroma, liver tissue, vasculature, and intestines in a 3D set up based on predefined specifications.

Embodiments of the methods as described herein can advantageously provide for: (1) non-contact approach minimizing effects on particle properties compared to "pick and place" approaches; (2) ultrasonic piezo transducers and ultrasound based patterning that allows for patterning of additives/reinforcements; in bio context, this permits mimicking of natural, complex tissues such as those found in the knee; and (3) Layered Manufacturing (LM) techniques that enable creation of highly complex structures with specific characteristics that can be varied across the cross-section of the construct in 3D space based on application requirements.

Various methods according to the subject matter as described herein further include acoustic manipulation and alignment of particles to fabricate 3D structures with preferentially organized particles. Embodiments of the methods as described herein involve depositing a homogeneous suspension of particles (fluid matrix containing particles) into a chamber with a pair of ultrasonic piezo transducers on opposite ends (single transducer and opposing solid reflector can also be used). When transducers are activated by a single power source and generator, their vibrations induce longitudinal bulk acoustic waves (BAW) within the fluid matrix. BAW from opposing vibrating transducers superimpose and create a standing bulk acoustic wave (SBAW). These forces can then cause particles within the fluid matrix to cluster at the nodes or nodal planes (separated by half the wavelength of the frequency parallel to the vibrating surfaces). As described herein, the non-contact approach accordingly advantageously uses sound waves to manipulate particles and is scaffoldless. Preferential alignments of short fibers within the polymer matrix can greatly enhance specific strengths (e.g., compression, tensile) and/or stiffness of the composites fabricated using the technics as described herein.

In one embodiment, the method adopts layered manufacturing (LM) principles which enable creation of highly complex structures with specific structural, mechanical, and biological characteristics that can be varied across the cross-section of the construct based on the application requirements. In the context of bioprinting of engineered tissues and organs, the method allows for creation of cells and/or growth additives within the biomaterial matrix in desired alignments mimicking natural tissue. For example, living cells may be aligned inside alginate hydrogel in a uniaxial pattern relevant for ligaments and tendons. A new range of short fiber composites such as collagen fibrils in GelMA hydrogel could also be created that combines the aforementioned benefits of alignment with the flexibility of layered manufacturing.

Embodiments of the methods as described herein introduce new non-contact label-free processes to engineer 3D constructs featuring preferential alignment of cells relevant to native tissues using ultrasound. Embodiments of the methods can include a fundamental process principle that entails the manipulation of cells into controlled spatial patterns using acoustic radiation force fields resulting from a longitudinal SBAW in the bioink. Embodiments of the methods and processes disclosed herein offer a synergistic mechanism for biofabrication of multi-layered constructs with intrinsic cellular patterns by the use of appropriate ultrasonic excitation and bioink deposition and crosslinking parameters to generate acoustic radiation forces large enough to rapidly align and entrap cells while maintaining their viability.

Embodiments of the present invention provide for a novel non-contact label-free process to engineer 3D constructs featuring preferential alignment of cells relevant to native tissues using ultrasound. Whereas surface acoustic waves (SAW)-based approaches may be well-suited for two-dimensional (2D) (i.e., planar) patterning or manipulation of single or multi-cell clusters in the microfluidics domain, they are inadequate for bulk 3D patterning in thicker viscous hydrogel matrices. In contrast, embodiments as disclosed herein use the ultrasound-assisted biofabrication (UAB) approach and its adaptation to 3D-bioprinting (UABp) that advantageously utilize BAW instead of SAW to create preferentially aligned 3D cellular constructs relevant for tissue engineering applications.

Embodiments of the methods as described herein can apply fundamental mechanics of the UAB process, and further apply critical process-structure relationships in biofabricating 3D constructs with highly organized cellular arrays using computational modeling and experimental design. A method of bioprinting of a multi-layered human knee meniscus featuring physiologically-relevant circumferential cellular patterns is also described herein. In one analysis, alginate was used as the model hydrogel due to its biocompatibility and immunoisolation characteristics. Further, in some methods, human adipose-derived stem cells (hASC) were used as the model cell line due their ability to differentiate into adipocytes, osteoblasts, chondrocytes, and fibroblasts, which are constitutive of musculoskeletal tissues.

Figure 2:
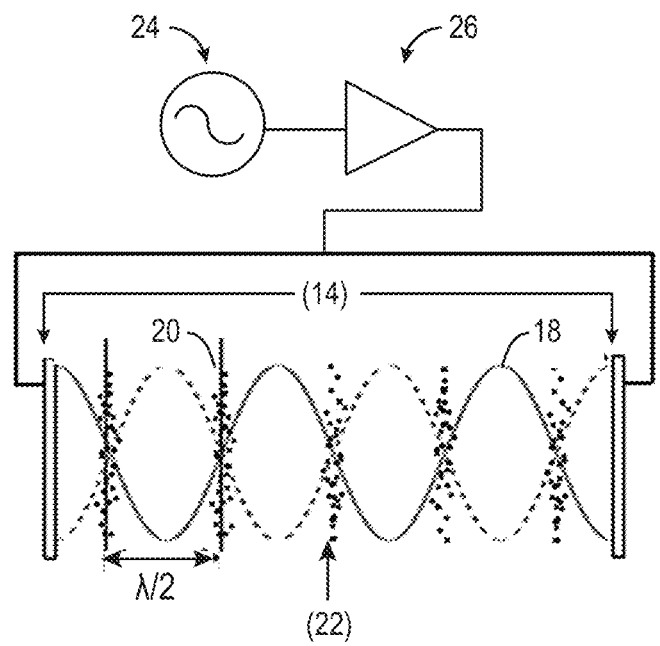
FIG. 2 is a structural schematic diagram of an ultrasound-assisted 3D bioprinting device including two piezo transducers with micro-particles clustered in strands at pressure nodes, as provided in accordance with some embodiments of the presently disclosed subject matter.
Figure 3:
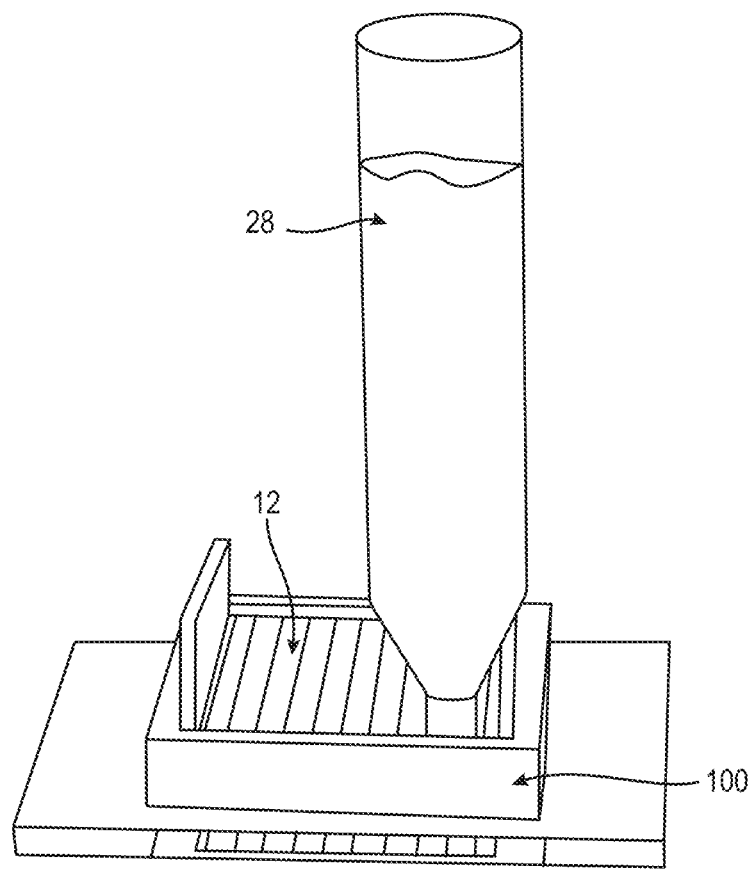
FIG. 3 illustrates a perspective view of a fluid matrix flowing from a container (e.g., 3D printer printhead) into an ultrasound-sound assisted bioprinting device ultrasound-assisted 3D bioprinting device, as provided in accordance with some embodiments of the presently disclosed subject matter.

According to one embodiment of the method, as illustrated in FIGS. 1-3 below, the method for aligning particles into predetermined patterns within a fluid matrix 12 comprises depositing a homogeneous fluid matrix 12 containing a suspension of particles 22 into a chamber 100 comprising a piezo transducer 14 and a reflector 16 positioned on opposing ends of the chamber 100. The method further comprises vibrating the piezo transducer to generate longitudinal bulk acoustic waves within the fluid matrix 12 such that waves from the piezo transducer 14 superimpose to form a standing bulk acoustic wave 18 to drive the particles 22 to cluster and align along one or more nodes or nodal planes 20 formed at locations where the standing bulk acoustic wave 18 intersects itself, wherein the nodes or nodal planes 20 are spaced apart from each other by a distance equaling half a wavelength (212) of the standing bulk acoustic wave 18, wherein the nodes or nodal planes 20 are parallel to, or mimic the contour of, a vibrating surface of the piezo transducer 14.

According to one or more embodiments, the spacing between the piezo transducer 14 and the reflector 16 is equal to an integer multiple of half the wavelength of the standing bulk acoustic wave. Signal generator 24 coupled to one or more piezo transducers 14 through RF amplifier 26 helps generate the acoustic vibrations on the piezo transducer(s) 14, as shown in FIG. 2. In one or more embodiments, fluid matrix 12 flows into the chamber 100 from a dispensing head 28, as shown in FIG. 3.

In the above noted example, since the vibrating surfaces are flat, the nodal planes are flat and parallel to the vibrating surface. In an embodiment wherein the vibrating surface is cylindrical, the nodes would represent concentric cylinders; in other words, the nodes or nodal planes would accordingly mimic the contour of the vibrating surface of the vibrating surface(s).

According to one embodiment, a method of ultrasound-assisted 3D bioprinting comprises depositing a bioink fluid matrix containing a suspension of cells into a chamber comprising two piezo transducers 14, instead of one as shown in FIG. 1, on opposing ends of the chamber. In this embodiment, the reflector 16 is replaced with an additional transducer 14. The remaining method remains similar to the fluid matrix embodiment. In detail, the method can further comprise vibrating the pair of piezo transducers 14 to generate longitudinal bulk acoustic waves 18 within the bioink fluid matrix such that waves from opposing piezo transducers superimpose to form a standing bulk acoustic wave 18 to drive the cells to cluster and align along one or more nodes 20 formed at locations where the standing bulk acoustic wave 18 intersects itself, wherein the nodes 20 are spaced apart from each other by a distance equaling half a wavelength (λ/2) of the standing bulk acoustic wave 18, with the nodes being parallel to, or mimicking a contour of, the vibrating surfaces of piezo transducers 14.

In various embodiments, the bioink fluid matrix can be a homogenous suspension of cells, proteins, micro particles, nano-particles, micro-fibers, nano-fibers, and/or similar other items.

The frequency applied at the transducer(s) as well as distance between transducers or transducer-reflector are variables that can be adjusted based on the process design. Frequency in the ultrasound range is selected as appropriate for a perceived application. Several variations of the embodiments are possible based on the desired application. In one embodiment, the fluid matrix-particle suspension is deposited into a chamber designed to resemble the shape of the desired construct. The suspension can be deposited using any common fluid dispensing technique such as, for example, extrusion through a nozzle, syringe, pipette, an inkjet head, and similar other technics. In other words, the method of fluid deposition itself is not central to the acoustics-based manufacturing method.

According to the embodiments as described herein, once the transducers are activated to create the SBAW, the particles will align within the fluid matrix at separations of half the wavelength of applied frequency. The fluid matrix is then solidified/gelled using chemical, heat, or light-based cross-linking methods to entrap the aligned particles in place. The chemical cross-linking agent can be introduced into the chamber at any stage of the alignment process, depending on the cross-linking time and concentration of the cross-linking agent. Similarly, for heat and light-based cross-linking of the bulk construct, the temperature of the chamber or light intensity can be increased at a rate that ensures that the particles are aligned before the fluid matrix is solidified or gelled. Heat/light cross-linking of selective regions of the construct can also be performed using a movable point source of energy. The construct can be made as a single bulk or in layers one at a time. The alignment of particles in the cross-linked layer underneath will not be affected by the SBAW to align particles within the non-cross-linked fluid in the layer above.

Figure 5:
FIG. 5 illustrates an overview of the computational modeling and experimental characterization associated with a bioprinting using an ultrasound-assisted 3D bioprinting device, as provided in accordance with some embodiments of the presently disclosed subject matter.

In at least one embodiment, the chamber shape and number of transducers can be customized to achieve more complex non-uniaxial patterns. For example, FIG. 5 shows design of an octagonal chamber with 4 pairs of transducers-reflectors to align particles circumferentially within the fluid matrix to resemble the organization in a knee meniscus. The control algorithm would allow for the transducers to be activated sequentially or in a preferred order so as to obtain desired patterns. This embodiment can be extended to where the pairs of transducers or transducers-reflectors are not affixed to the chamber, and their location can be manipulated to obtain more complex patterns. Again, the order of excitation of the pairs can be easily controlled via a control algorithm.

In at least one embodiment, a digitally-driven 3D-printing method is applied wherein the fluid dispensing mechanism as well as the acoustic alignment apparatus forms part of an integrated 3D-printing head. The acoustic alignment apparatus can consist of a rotating bracket onto which a pair of transducers (or a transducer and a reflector) are mounted. As a part of a continuous process, in sequence, the fluid-particle suspension is deposited, then the particles get aligned by the acoustic apparatus, and subsequently cross-linked, for example, by chemical, heat, or light-based cross-linking strategies, as explained earlier. The degree of rotation and the distance between the transducers or transducer-reflector can be advantageously adjusted to accommodate the size of the construct in between.

Embodiments of the methods disclosed herein can advantageously provide for a new processing system by way of a bioprinting machine and an improved method of fabricating engineered tissues such as ligaments, tendons, knee meniscus, and similar other tissues. Embodiments of the methods disclosed herein can find applications in clinical, diagnostic, and research fields. Embodiments of the methods disclosed herein can also be easily extended to creating functional polymer, metal, or ceramic based composites with highly enhanced specific mechanical properties for non-biological applications. For example, the methods disclosed herein can allow for predetermined arrangement of particles such as, for example, nanoparticles in 3D structures with predetermined orientation, alignment and concentration of the particles within a fluid matrix followed by solidifying or gelling to result in an improved polymer matrix than what is conventionally known in the relevant art.

The inventors analyzed the fundamental mechanics of the UAB process and characterized the critical process-structure relationships in biofabricating 3D constructs with highly organized cellular arrays using computational modeling and experimental design. According to one example, the bioprinting of a multi-layered human knee meniscus featuring physiologically-relevant circumferential cellular patterns is illustrated herein. In this example, alginate was used as the model hydrogel due to its wide usage in tissue engineering on account of its biocompatibility and immunoisolation characteristics. Human adipose-derived stem cells (hASC) were used as the model cell line given their ability to differentiate into adipocytes, osteoblasts, chondrocytes, and fibroblasts, which are constitutive of musculoskeletal tissues. The inventors understand that this is the first study to characterize BAW-based biofabrication and demonstrate its extension to 3D-bioprinting.

Figure 4A:
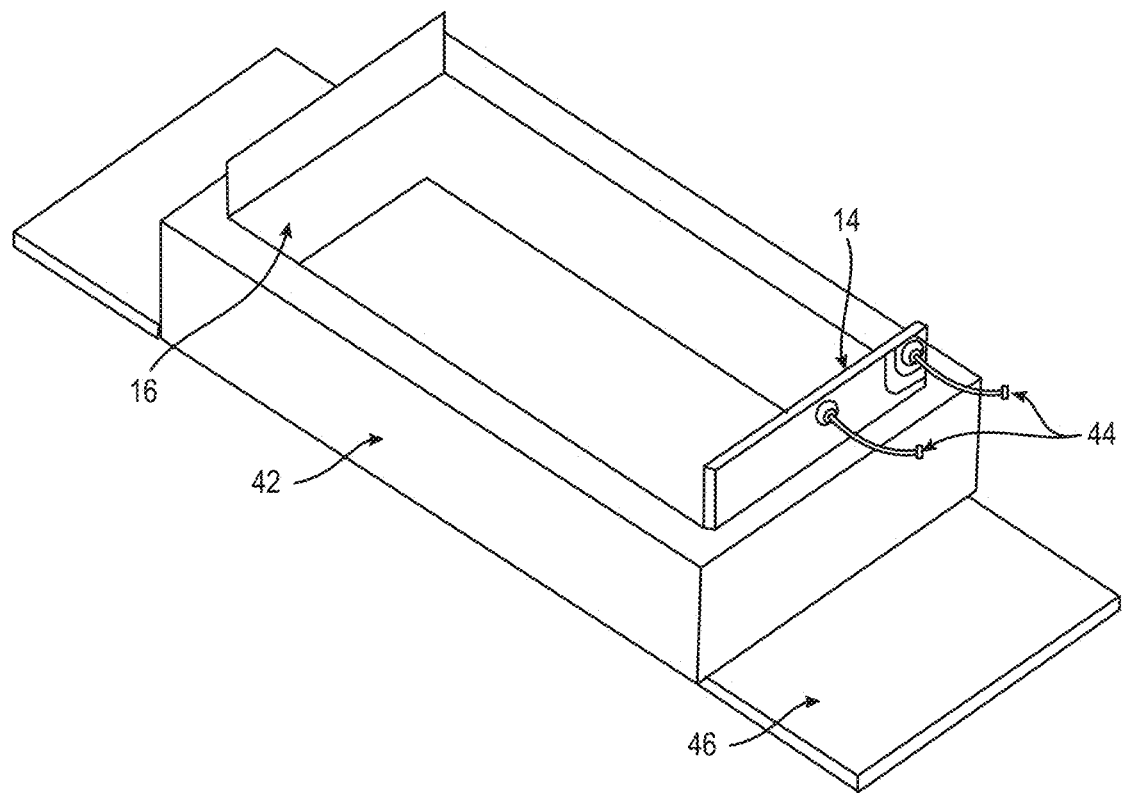
FIG. 4a illustrates a perspective view of a platform used for ultrasound-assisted biofabrication (UAB) and bioprinting (UABp); and, FIG. 4b illustrates a structural schematic diagram of an ultrasound-assisted 3D bioprinting device including one piezo transducer and an opposing reflective surface, and a depiction of acoustic field distribution with nodal and antinodal regions within bulk ultrasonic standing wave (BUW), with the cells clustering at the nearest nodal region forming a cellular array, as provided in accordance with some embodiments of the presently disclosed subject matter.
Figure 4B:
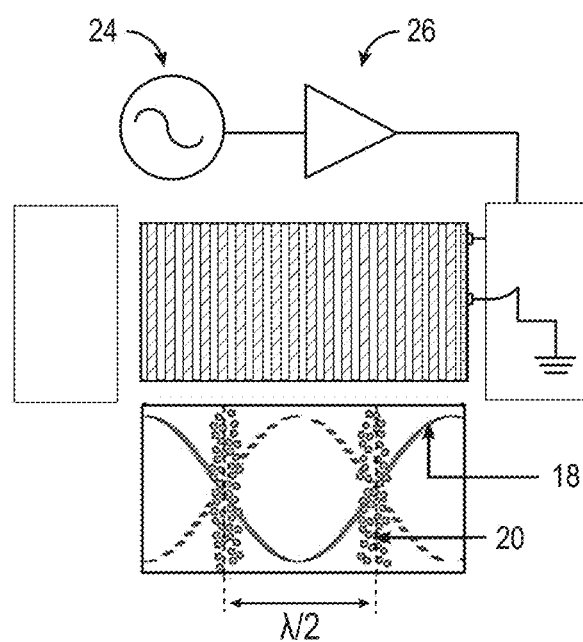

FIGS. 4a and 4b illustrate a schematic of the platform central to UAB along with the mechanics of aligning cells suspended in the bioink using ultrasound. FIG. 4a illustrates a platform for ultrasound-assisted biofabrication (UAB) and bioprinting (UABp). FIG. 4b illustrates a depiction of acoustic field distribution with nodal and antinodal regions within bulk ultrasonic standing wave (BUW). The cells cluster at the nearest nodal region forming a cellular array. As shown in FIG. 4a, the apparatus includes rectangular enclosure 42, connections to amplifier 44, and glass slide 46. In this embodiment, piezo transducer 14 is a piezo ceramic plate transducer. In on example, rectangular enclosure 42 can have a height of 10 mm, width of 20.5 mm and a length of 42 mm. In this example, the pressure wave generated from a vibrating piezo-transducer in contact with the bioink interferes with the wave's reflection from an opposing reflecting surface, resulting in a longitudinal standing bulk acoustic wave 18 in the bioink, prior to it being crosslinked. Since the transducer is actuated by a sinusoidal voltage signal with frequency in the ultrasonic range, the resulting wave will be referred to as bulk ultrasonic wave (BUW) henceforth. The acoustic pressure along the X-axis (FIG. 1) of the BUW is given by equation (1).

$$p(x, t) = P_o \cos(2\pi f t)\cos\left(\frac{2\pi f x}{c}\right) \quad (1)$$

where, $P_o$ is the pressure amplitude in the bioink layer at the interface with the transducer, f is the transducer vibration frequency, and c is the longitudinal pressure wave speed in the bioink. An advantageous hard wall boundary condition of zero fluid particle velocity (equation (2)) at the reflector (x=L) constrains the separation between the transducer and reflective glass surface (L), necessary to generate a BUW, to an integer multiple of half wavelength (λ) of ultrasound (equation (3)).

$$y(L, t) = -\frac{1}{\rho_b}\int_0^t \frac{\partial p}{\partial x}dt = 0 \quad (2)$$

$$L = \frac{nc}{2f} = \frac{n\lambda}{2} \quad (3)$$

where $\rho_b$ is the density of bioink and n is the number of pressure nodes (p=0) in BUW, which appear as 2D planes parallel to the ultrasound-emitting transducer surface and separated by half the wavelength. Each cell, assumed to be a near buoyant spherical particle, suspended between any two adjacent pressure nodes in the bioink experiences acoustic radiation force (equation (4)), which pushes it towards the nearest pressure node.

$$F_{radiation} = \left(\frac{\pi}{24}\right)(k_b - k_c)d^3\left(\frac{2\pi}{\lambda}\right)P_0^2\sin\left(\frac{2\pi x}{\lambda}\right) \quad (4)$$

where d is the cell diameter, and $k_b$ and $k_c$ are the compressibility of the bioink (hydrogel solution) and cell, respectively. While the cell traverses to a pressure node, it experiences a fluid resistive force from the bioink (equation (5)).

$$F_{resistive} = 3\pi\eta dv \quad (5)$$

where η is the dynamic viscosity, and v is the instantaneous velocity of the cell.

Equations (1)-(5) can have several practical implications. First, increasing the ultrasound frequency would result in smaller separation between the pressure nodes and resulting cell clusters at the nodes. Second, $F_{radiation}$ exceeding $F_{resistive}$ would facilitate movement of cells to the nodes. As such, $F_{resistive}$ will be higher in bioinks with higher viscosities. In this scenario, the correspondingly higher $F_{radiation}$ can be achieved by increasing the pressure amplitude. Finally, increasing the duration of transducer actuation will increase the probability of cells clustering near the pressure nodes.

According to at least one embodiment, the UAB platform is comprised of two primary units—bioink chamber and power-signal source (see FIG. 4b). The bioink chamber design is primarily informed by equation (3), wherein the separation between the BUW-inducing transducer and reflectors (L) has to be an integer multiple of half the wavelength. For each of the four frequencies (table 1), L=42 mm satisfies this requirement. Accounting for the transducer thickness that is a characteristic of its resonant frequency and reflective cover glass thickness (0.2 mm), the chamber was custom-designed for each frequency to achieve an effective L of 42 mm and width and thickness of 20.5 mm and 10 mm, respectively. The rectangular enclosures were 3D-printed out of acrylonitrile butadiene styrene (ABS) (uPrint SE Plus, Stratasys, Eden Prairie, Minn.) and covered with Tegaderm™ film (3M Technologies, St. Paul, Minn.) to render the surfaces biocompatible and electrically insulating. Next, a Corning® cover glass (Sigma-Aldrich, St. Paul, Minn.) and appropriate piezo ceramic plate transducer (Steiner and Martins Inc., Dorsal, Fla.) covered with Tegaderm film were attached to opposing ends of the ABS enclosure. Finally, the upfitted enclosure was affixed onto a Corning microscope slide (Sigma-Aldrich) on the bottom to complete the bioink chamber construction. Each chamber was tested to ensure there was no leakage of liquid or current. At the beginning of each experiment, the transducer terminals were connected to a function generator (Keysight Technologies Inc. Santa Rosa, Calif.) via an intermediate high frequency radio frequency power amplifier (Electronics & Innovation Ltd., Rochester, N.Y.).

FIG. 5 provides an overview of the computational modeling (Study 1) and experimental characterization (Studies 2 through 5). As part of Study 1, a multi-physics finite element (FE) model was created to determine the longitudinal BUW pressure distribution characteristics that govern the alignment of suspended cells. This formed the basis of Study 2 wherein the effects of ultrasound frequency (0.71 MHz, 1 MHz, 1.5 MHz, and 2 MHz) and signal source voltage amplitude (100 mVpp and 200 mVpp) on the alignment characteristics (spacing between adjacent arrays of aligned cells and the degree of cell concentration at pressure nodes) of hASC suspended in alginate solution was experimentally characterized. In Study 3, the effects of the two extreme frequencies (0.71 and 2 MHz) and the two amplitudes on the metabolic activity of aligned hASC in crosslinked alginate constructs over 4 days were investigated. In Study 4, the effects of alginate solution viscosity (70 cP and 5 cP) and actuation duration (10 and 20 min) on hASC viability and alignment characteristics were assessed. Finally, in Study 5, the UABp of multi-layered alginate constructs with circumferential hASC alignment patterns was demonstrated.

Computational modeling of BUW pressure distribution was conducted as follows. Under ideal theoretical conditions (section 2), BUW nodes appear along planes parallel to the actuated transducer and reflectors. The effects of potential wave reflection from the chamber sidewalls was neglected, and strain across the surface of the transducer in response to the sinusoidal voltage signal was assumed to be isotropic. However, these assumptions did not hold in the practice. Therefore, built upon foundational analysis by Scholz et al, the inventors have developed a 2D linear acoustic FE model in COMSOL Multiphysics® (Comsol Inc., Burlington, Mass.) to more accurately map the BUW pressure distribution in the bioink chamber of the UAB platform in response to the four ultrasonic frequencies (Table 1). Table 1 below illustrates transducer frequencies and corresponding theoretical spacing between adjacent BUW pressure nodes and expected number of such nodes (assuming c=1500 m/s).

TABLE 1

| f | 0.71 MHz | 1 MHz | 1.5 MHz | 2 MHz |
|---|---|---|---|---|
| $\lambda/2$ | 1.05 mm | 0.75 mm | 0.5 mm | 0.375 mm |
| n | 40 | 56 | 84 | 112 |

Acoustic-Piezoelectric interaction (frequency domain) interface with multiphysics attributes was set-up as shown in FIGS. 4a and 4b. Given that the primary component of alginate solutions is water (98%), water with frequency dependent attenuation per unit length was assigned as the liquid domain between the piezo-transducer and glass reflector. Elastic and material constants in stress-charge form as well as dielectric and structural loss coefficients were assigned to the transducer as specified by the manufacturer. A fixed constraint was assigned to all edges of the chamber enclosure other than the transducer edge that interfaces with the liquid. To this edge, considering 50 dB amplification of input voltage, a harmonic perturbation with amplitude of 32 V or 16 V, corresponding to 100 mVpp or 200 mVpp input voltage, respectively, was applied. To define the multiphysics interface, an acoustic structure boundary was defined at all edges where liquid is in contact with solid, and the piezoelectric effect was defined at the transducer. A free triangular mesh was defined for all domains with maximum element size of 30 μm to fulfill the convergence criterion of mesh size less than $\lambda/10$ for each frequency. At each frequency, the transducer thickness was modeled as per manufacturer's thickness specification. The model was computed (top view) at the four frequencies and two voltage amplitudes tested in the subsequent experimental design.

According to at least one embodiment, the alginate-hASC bioink was prepared as follows. Passage 1 hASC (StemPro™ R7788115, Thermo Fisher Scientific, Waltham, Mass.) were used, and cryopreserved cells were thawed and cultured (37° C., 5% CO2) in T-75 flasks (Nunc™ Easy Flask™, Thermo Fisher Scientific) with MesenPRO RS™ basal medium with growth supplement (Thermo Fisher Scientific) and 1% L-Glutamine (Thermo Fisher Scientific) at a seeding density of 250,000 cells per flask. Media changes were performed every 48 hours until 80% confluency was reached.

A higher viscosity sodium alginate (Manugel® GMB, DuPont, Wilmington, Del.) was used as the bioink matrix in all four experimental studies. Additionally, a lower viscosity sodium alginate (Protanal® LFR 5/60, DuPont) was used in Study 4. For each study, for one or both alginates as necessitated by the experimental design, 30 ml of 2% w/v hydrogel solution was prepared by mixing the appropriate proportions of alginate powder in sterile phosphate buffered saline (PBS) (Sigma-Aldrich) in a 50 ml tube and vortexing for 1 min followed by sonication at 60 Hz for 1 hour. The solution was then incubated (37° C.) for 72 hours to make it more homogenous. Finally, the solution was autoclaved at 121° C. and 16 psi for 30 min (BioClave 16, Benchmark Scientific Inc, Sayreville, N.J.) for terminal sterilization. Relevant to study 4, the average dynamic viscosity of the higher and lower viscosity autoclaved solutions were determined to be 70 cP and 5 cP, respectively, using a rheometer (Brookfield, Middleborough, Mass.).

To concoct the bioink, the hASC were harvested from 80% confluent flasks by washing with 4 ml of Hank's balanced salt solution (Sigma-Aldrich) followed by addition of 2 ml of 0.25% Trypsin-EDTA (Sigma-Aldrich). The trypsinized cell suspension was neutralized with 4 ml of media after 5 min and centrifuged at 120 g for 5 min to obtain the cell pellet. The pellet was gently mixed with the appropriate volume of sterilized 2% alginate solution to obtain the bioink with a concentration of 1×106 cells/ml.

Figure 6A:
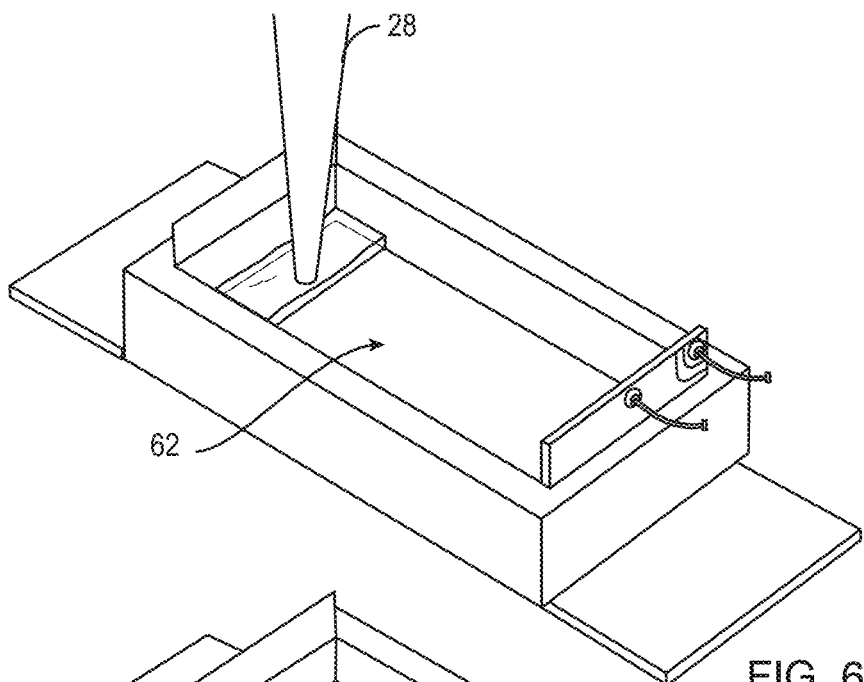
FIG. 6a illustrates a perspective diagram of a biofabrication of alginate constructs with ultrasonically aligned cells with aginate bioink 62 with homogeneously suspended cells ($1\times10^6$ cells/ml) deposited into the bioink chamber containing PBS buffer.
Figure 6B:
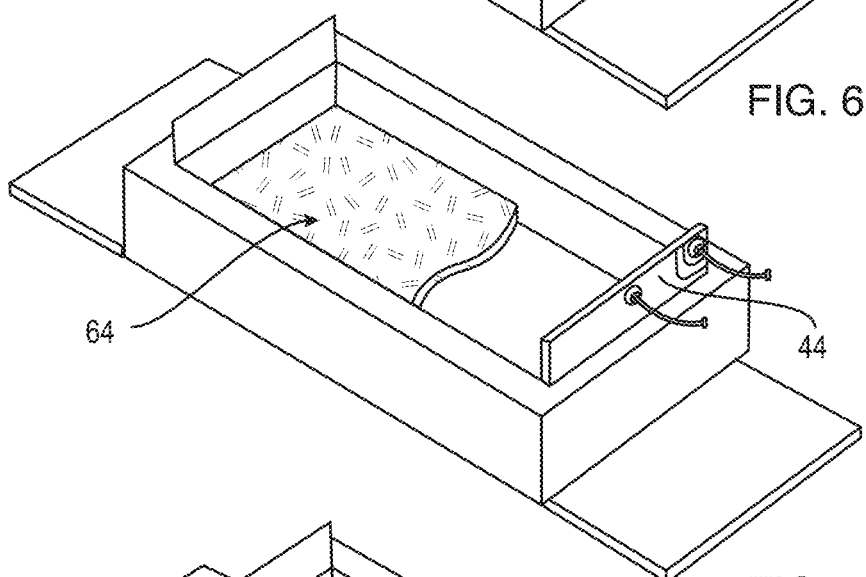
FIG. 6b is a perspective view illustrating a transducer actuated in a thickness mode to yield a thickened bioink 64; and, FIG. 6c is a perspective view illustrating chemically crosslinked bioink 66 that is as the cells align along nodes or nodal planes parallel to transducer surface, as provided in accordance with some embodiments of the presently disclosed subject matter.
Figure 6C:
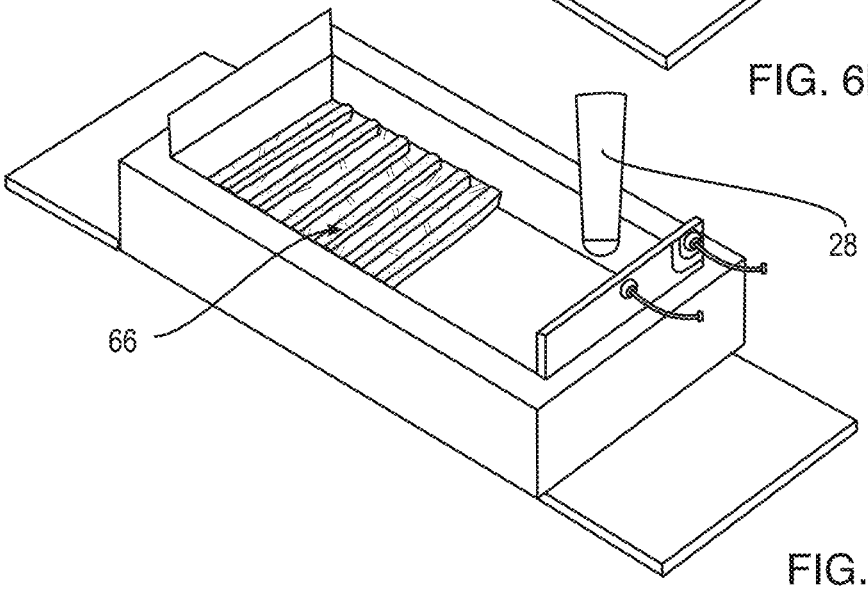
FIG. 6d illustrates a photograph of a representative construct in a 2 MHz bioink chamber with aligned hASC.
FIG. 6i is microscopic view of the product of FIG. 6d as seen from the top at a scale bar=250 μm; and, FIG. 6j is a microscopic view of the product of FIG. 6d as seen at a cross-section at a scale bar=250 μm, as provided in accordance with some embodiments of the presently disclosed subject matter.
Figure 6D:
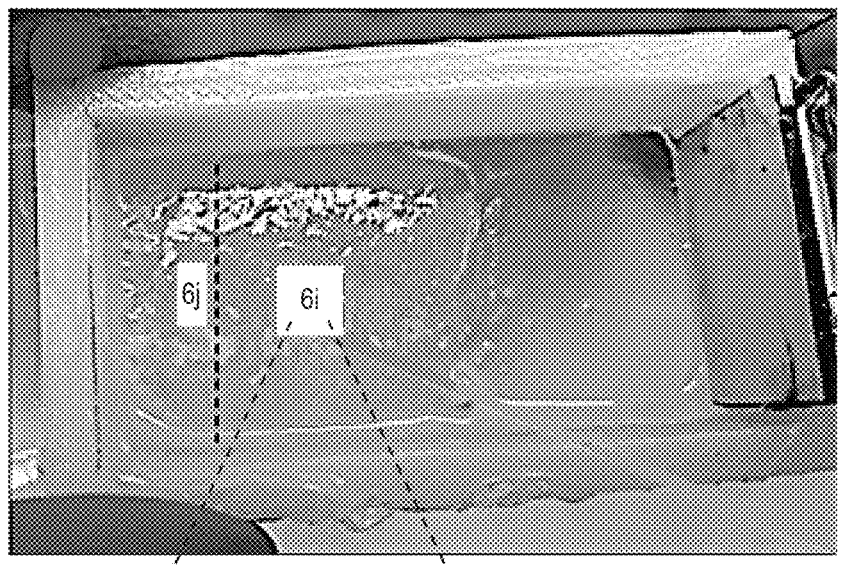
Figures 6I, 6J:
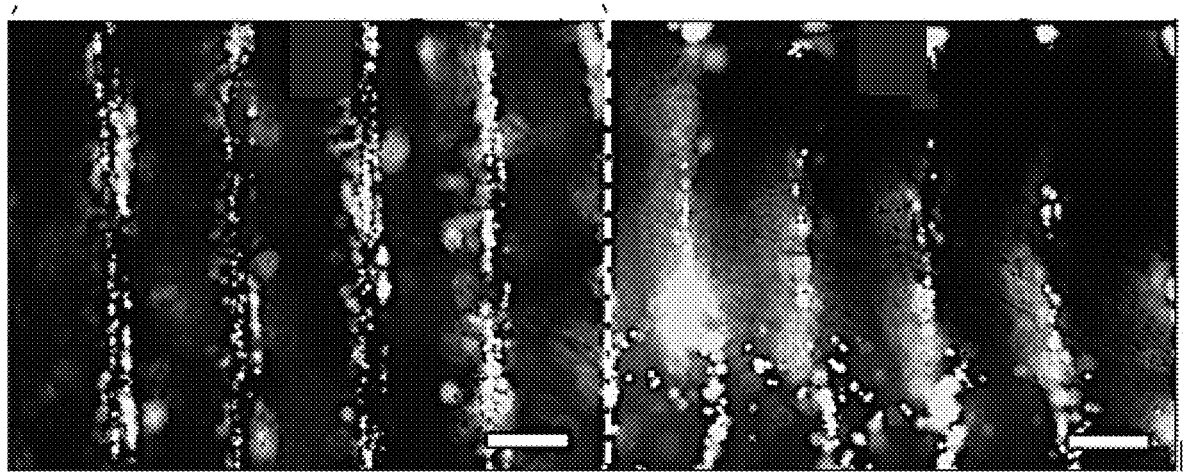

The fundamental protocol used to create alginate constructs with aligned cellular arrays using the UAB platform is illustrated in FIG. 6a-6j. The process parameters (frequency, amplitude, alginate viscosity, actuation duration) utilized in each experiment using this protocol were governed by the study design as illustrated in FIG. 5. FIG. 6a is a perspective illustration of an Alginate bioink with homogeneously suspended cells (1×106 cells/ml) deposited into the bioink chamber containing PBS buffer. FIG. 6b illustrates a transducer being actuated in thickness mode. FIG. 6c illustrates the bioink being chemically crosslinked as the cells align along nodes parallel to transducer surface. FIG. 6d illustrates a representative construct (in a 2 MHz bioink chamber) with aligned hASC; FIG. 6i illustrates the construct of FIG. 6d when viewed microscopically from the top, and FIG. 6j illustrates the construction of FIG. 6d when viewed microscopically at a cross-section, both at a scale bar=250 µm.

According to at least one embodiment, prior to each experiment, the bioink chamber was disinfected by repeated swabbing with 70% ethanol followed by 30 min exposure to UV radiation inside a biosafety cabinet. The transducer was then connected to the voltage source via the power amplifier. To begin fabrication of the construct, 4 ml of PBS was added to the chamber, and the appropriate actuation signal was applied in 1 s bursts with a 1.5 second pause to reduce Stokes drag on cells and prevent overheating and loss in compliance properties of the transducer. Next, 1 ml of the bioink with a concentration of 1×106 cells/ml was deposited into the actuated chamber. After 1 min, 4 ml of 0.5% w/v sterile $CaCl_2$ was introduced at the rate of 2 ml/min to initiate alginate crosslinking. The actuation signal was turned off after the intended duration. The construct was further crosslinked in 0.5%, 1% and 2% sterile $CaCl_2$ solution in serial 20 min intervals. This serial gelation protocol was established in our lab prior to commencing the experimental design in order to obtain reproducible high fidelity constructs that are minimally affected by the ion exchange that occurs during crosslinking. Finally, the gelled construct (thickness=3.5±0.5 mm) was aseptically transferred from the chamber to a six-well plate for further analyses.

UABp of alginate knee meniscus construct with circumferentially-aligned hASC was conducted as follows. Based on the fundamental principles of UAB (as explained earlier), an octagonal bioink chamber comprising of four pairs of piezo-transducers and opposing reflector surfaces was designed and fabricated following procedures described earlier, for example, with regards to FIGS. 5 and 6. This chamber was integrated with a BioassemblyBot™ (Advanced Solutions Life Sciences, Louisville, Ky.) for Study 5. Alginate (Manugel® GMB) disinfected by 1 h exposure to UV radiation was used as the bioink matrix for this study. The viscosity of this UV-disinfected solution (200 cP) makes it more suitable for 3D-bioprinting than the autoclaved solution (70 cP). Neutral red-stained (N 2889, Sigma-Aldrich) hASC suspended within this alginate (1×106 cells/ml) constituted the bioink. The STL file of a previously biomodeled medial knee meniscus, sliced with a layer height of 1.2 mm, was setup in TSIM® software (Advanced Solutions Life Sciences) to ensure that the subsequent bioprinting occurred within the octagonal bioink chamber. A total of 7 ml bioink was bioprinted with an extrusion pressure of $15×10^{-3}$ $N/mm^2$ at a speed of 12 mm/s in a total of 4 layers to create the 3D meniscus construct. Throughout the bioprinting cycle, circumferential alignment was imparted to cells within each layer through serial actuation of the transducers (200 mVpp) via high-frequency relays (G6K 2P RF, Omron Electronics LLC, IL). One-at-a-time transducer actuation (1 second actuation before switching to adjacent transducer) alleviated the need for burst mode signal and prevented interference of the pressure waves that would otherwise simultaneously emanate from the other transducers to disrupt the cell alignment. A gelation protocol similar to the one described earlier, with the crosslinker ($CaCl_2$) added between layers, was used to entrap the cells within the constructs as they were being aligned.

Assessment of constructs fabricated via UAB and UABp was conducted as follows. Cell viability, spacing between centroids of adjacent arrays of viable cells (henceforth referred to as inter-array spacing), and the degree of concentration of viable cells at the nodes (henceforth referred to as nodal concentration) were the three outcome metrics of interest for Studies 2 and 4. Cell metabolic activity was the primary metric for Study 3. The LIVE/DEAD® assay (Life Technologies, Carlsbad, Calif.) was used to assess hASC viability in the crosslinked constructs. The sample size was n=3 constructs for each of the treatment (UAB) and control (bioink not subject to UAB) groups. 1 ml of PBS containing 0.5 µl calcein AM and 2 µl EthD-I was added to each construct in a six-well plate and incubated for 15 min. Subsequently, each construct was imaged at three random locations using a fluorescence microscope (DM5500B, Leica Microsystems, Wetzlar, Germany) The live/dead images were analyzed using a custom MATLAB (MathWorks, Natick, Mass.) script to determine % cell viability (N=9 images per experimental and control group). Briefly, a maximal gradient method for edge detection was applied to sharpened grayscale translations of red and green fluorescent images, followed by Hough transformation to detect circles within a range of diameters relevant for hASC, and % cell viability computed from these estimates of live and dead cells.

To measure the inter-array spacing and the nodal concentration, the live/dead images of all experimental groups were analyzed using another custom MATLAB script (N=18 images per group). Briefly, an edge detection protocol was applied to detect "live" pixels corresponding to viable cells within a user-specified bounding box (n=2 per image) enclosing two adjacent aligned cellular arrays. The separation between the centroids of adjacent arrays of aligned cells signified the inter-array spacing. The standard deviation of positions of "live" pixels along the x-axis was a measure of the nodal concentration (inverse proportionality), with lower standard deviations indicating higher nodal concentrations.

The alamarBlue® (aB) assay (Thermo Fisher Scientific) was used to assess the hASC metabolic activity over 4 days. The sample size was n=3 constructs for each of the treatment and untreated control groups. An additional acellular control was included in each experiment to normalize the aB readings. Each crosslinked construct was cultured in 3 ml of media in a six-well plate (37° C., 5% $CO_2$), with media changes performed every 24 hours. At days 2 and 4, the supernatant media was replaced with 3 ml of fresh media containing 10% v/v of the aB reagent. After 4 hours, three 1 ml media samples from each construct were analyzed for absorbance on a micro-plate reader (Tecan, Männedorf, Switzerland) at 570 nm and 600 nm excitation and emission wavelengths, respectively. The absorbance data normalized to the acellular control is reported as % aB reduction.

In Study 5, top-down images of the meniscus construct were captured at different zones along its semi-lunar contour and at a vertical cross-section using a dissection microscope (EZ4 D, Leica Microsystems) and a fluorescence microscope (Leica DM5500B; 600 nm excitation) to ascertain the circumferential alignment of viable cells.

In terms of statistical analyses, for studies 2-4, two-way ANOVA and Tukey post-hoc tests were used to assess the effects of the corresponding two independent factors and their interactions on the appropriate metrics of interest. Additionally, for Studies 2 and 3, t-tests were performed to compare % cell viability and % aB reduction, respectively, between experimental and control groups. All tests were performed in JMP® (SAS, Cary, N.C.) and statistical significance assessed at $\alpha=0.05$.

Figures 7A, 7B:
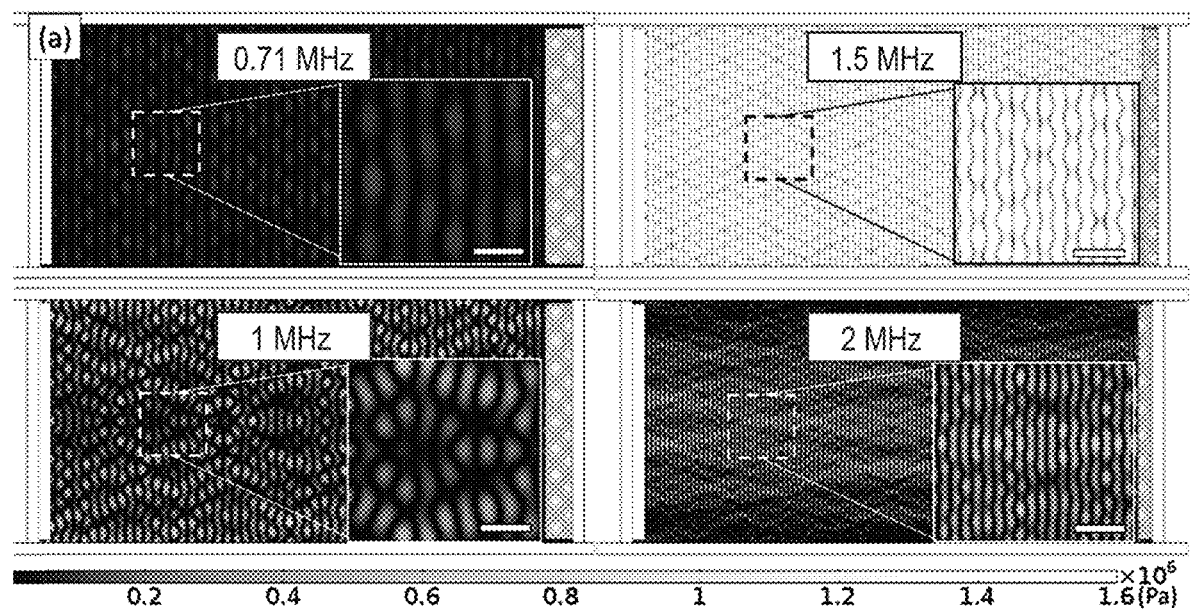
FIG. 7a illustrates a top view of the absolute acoustic pressure distribution across the UAB bioink chamber and magnified insets at scale bar=2 mm at 200 mVpp voltage amplitude across different frequencies in a computational model; and, FIG. 7b illustrates estimates of acoustic radiation force ($F_{radiation}$) experienced by cells at different frequencies and amplitudes, as provided in accordance with some embodiments of the presently disclosed subject matter.

A FE model of longitudinal BUW pressure distribution obtained in Study 1 is shown in FIGS. 7a and 7b. FIG. 7a illustrates a top view of the absolute acoustic pressure distribution across the UAB bioink chamber (and magnified insets; scale bar=2 mm) at 200 mVpp voltage amplitude across different frequencies. Thickness of transducers (indicated by cross-hatched pattern on the right in each figure) is dependent on the resonant frequency. Analogous to theory, the standing wave pattern consists of nodes parallel to the transducer surface. A non-uniform compliance of transducer along its emitting surface coupled with interference of pressure wave reflected from the sidewalls of the bioink chamber, which was modeled according to what is expected in practice, rendered a scalloped profile to the nodes or nodal planes in contrast to perfectly flat planes in theory. Furthermore, the number of FE-estimated nodes or nodal planes matched the theoretical estimates (see Table 1), and an increase in frequency resulted in a decrease in the width of the nodes or nodal planes as well as a decrease in the spacing between adjacent nodes or nodal planes.

FIG. 7b is a table providing estimates of $F_{radiation}$ experienced by cells at different frequencies and amplitudes. The peak acoustic pressure was found to have a direct relationship with the applied voltage amplitude. In addition, a non-linear dependence of pressure on transducer frequency was also evident, with maximum peak pressure achieved at 1.5 MHz and minimum at 0.71 MHz. The theoretical estimates of $F_{resistive}$ experienced by cells at different frequency-amplitude combinations, computed from the FE-estimated pressure amplitudes for hASC (d=21 µm, $k_c$=40×10$^{-11}$ Pa$^{-1}$) in water ($k_b$=45.8×10$^{-11}$ Pa$^{-1}$), are presented in FIG. 7b. Higher amplitude resulted in higher $F_{radiation}$ across all frequencies, and the highest $F_{radiation}$ was generated at 1.5 MHz for each voltage amplitude, following the similar non-linear relationship with frequency as acoustic pressure.

Representative live/dead images at different frequency-amplitude combinations and summary of the % cell viability data from the experimental design are presented in FIG. 8. Results of the two-way ANOVA indicate that the interaction of frequency and amplitude had an effect on the viability of hASC (p=0.0018). The hASC viability of 1 MHz-200 mVpp and 1.5 MHz-200 mVpp groups was significantly lower in comparison to every other treatment group as well as their corresponding untreated controls (p<0.05). Of the other treatment groups, the hASC viability in only the 0.71 MHz-200 mVpp group was significantly lower than its corresponding untreated control (p<0.05).

The lower viability in the 1.5 MHz-200 mVpp group can be attributed to the elevated acoustic radiation force experienced by the cells. The estimated $F_{radiation}$ for this group was at least an order of magnitude higher than other groups (see FIG. 5). Among all treatment groups, the 1 MHz-200 mVpp and 0.71 MHz-200 mVpp groups exhibited the highest magnitude of perturbations during the experiments. These perturbations resulted from non-uniform strains exerted across the wave-emitting surface of the "non-ideal" transducer (as opposed to isotropic strain expected from a theoretically "ideal" transducer). Furthermore, the estimated $F_{radiation}$ in the 1 MHz-200 mVpp group was at least three orders of magnitude higher than that in the 0.71 MHz-200 mVpp group. The combination of the perturbations and acoustic radiation force can be postulated to have affected the hASC viability of that group.

Figure 8A:
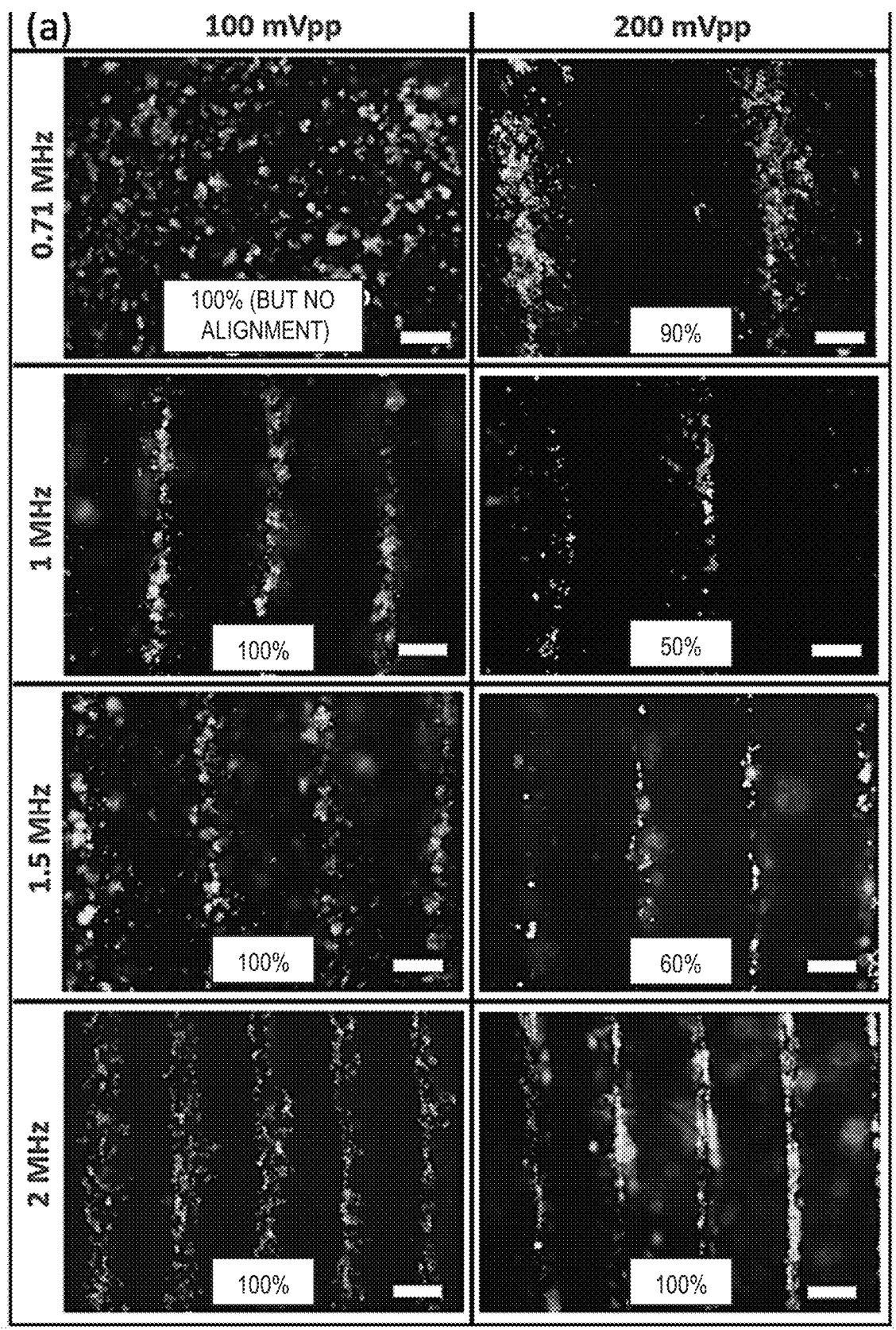
FIG. 8a illustrates representative microscopic live and dead images of hASC-alginate constructs for various treatment and control groups at a scale bar=250 µm; and, FIG. 8b illustrates a summary of % cell viability data at various frequencies and voltage amplitudes, as provided in accordance with some embodiments of the presently disclosed subject matter.
Figure 8B:
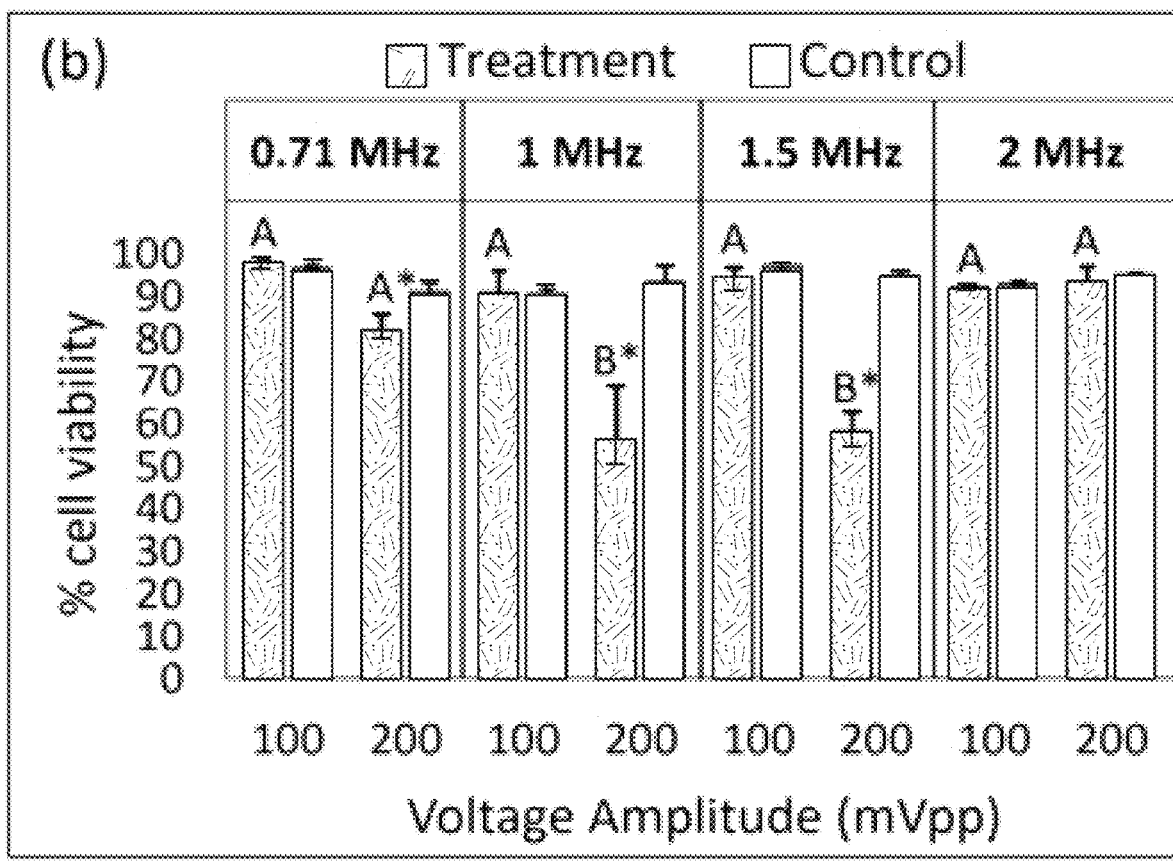

FIG. 8a illustrates representative live/dead images of hASC-alginate constructs for all treatment and control groups at a scale bar=250 µm. FIG. 8b provides a summary of % cell viability data. Groups denoted by A and B were significantly different from each other (p<0.05). ANOVA indicates a significant interaction effect of frequency and amplitude. * indicates significant reduction in cell viability between corresponding treatment and control groups. (p<0.05).

Figure 9A:
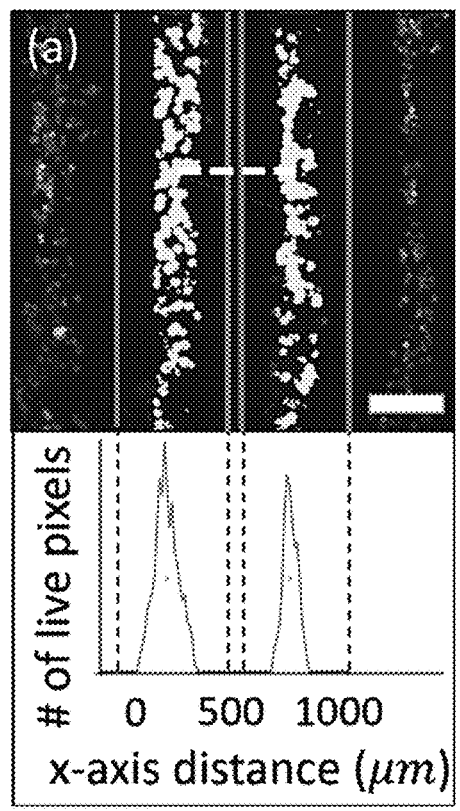
FIG. 9a illustrates representative microscopic images highlighting the measurement of inter-array spacing and nodal concentration using MATLAB analyses at a scale bar=250 µm; and, FIG. 9b illustrates a summary of inter-array spacing on the left side image, and nodal concentration data on the right side image, both at various frequencies and voltage amplitudes, as provided in accordance with some embodiments of the presently disclosed subject matter.
Figure 9B:
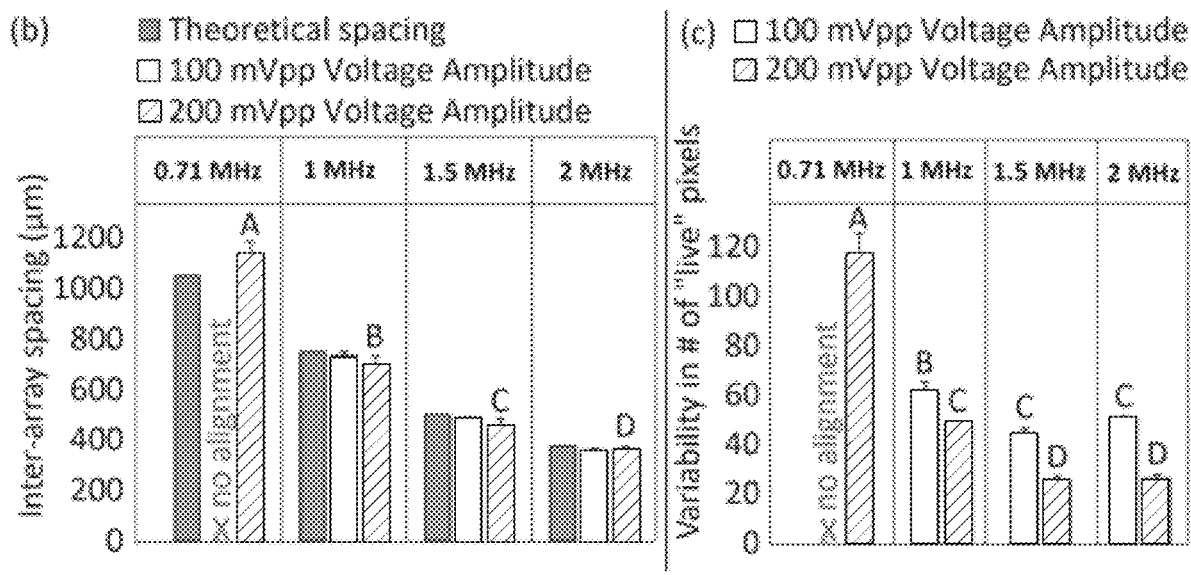

The inter-array spacing for all treatment groups in the experimental design is summarized in FIGS. 9a and 9b. FIG. 9a illustrates representative images highlighting the measurement of inter-array spacing and nodal concentration using MATLAB analyses at a scale bar=250 µm. The left side graph of FIG. 9b provides a summary of inter-array spacing, and the right side graph of FIG. 9b provides nodal concentration data, respectively. Groups denoted by A, B, C, and D were significantly different from each other (p<0.05). Frequency had a significant effect on the inter-array spacing while interaction of frequency and amplitude had a significant effect on the nodal concentration.

The theoretical values of the spacing (λ/2; see Table 1) are also included in the plot. Of the eight treatment groups, cell alignment was not observed in only one –0.71 MHz-100 mVpp. This can be attributed to low acoustic radiation force at this factor combination; the estimated $F_{radiation}$ for this group was at least three orders of magnitude lower than that for the other groups. Results of the ANOVA show that frequency had a significant effect on the inter-array spacing (p<0.0001), but the amplitude or their interaction did not. Furthermore, the mean inter-array spacing for each treatment was very close to its corresponding theoretical estimate. These findings corroborate the theory.

The nodal concentration data is summarized on the right side chart of FIG. 9b. ANOVA results show that the interaction effect of frequency and amplitude was significant (p=0.0187). This indicates that at higher amplitudes and frequencies, the cells were more closely clustered along the nodal plane. Post-hoc tests indicate that the nodal concentrations were highest for the 1.5 MHz-200 mVpp and 2 MHz-200 mVpp groups.

Figure 10:
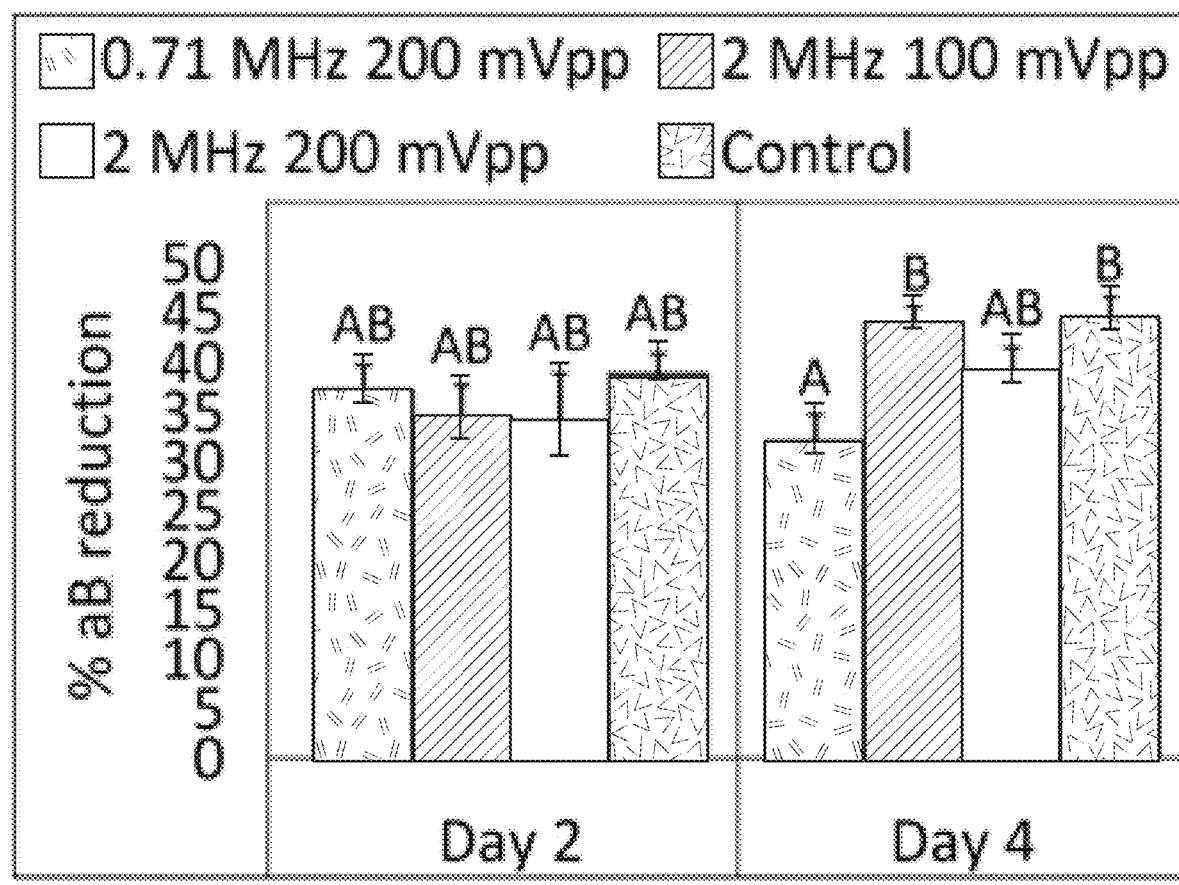
FIG. 10 illustrates results of hASC metabolic activity in constructs fabricated at different frequency-amplitude combinations over 4 days in comparison to untreated control groups, as provided in accordance with some embodiments of the presently disclosed subject matter.

With regard to Study 3, the effects of frequency and amplitude on metabolic activity of aligned hASC: The % aB reduction data from the experimental design is summarized in FIG. 10. Accordingly, FIG. 10 illustrates results of hASC metabolic activity in constructs fabricated at different frequency-amplitude combinations over 4 days in comparison to untreated control groups. The groups denoted by A and B were significantly different from each other (p<0.05). The groups denoted by AB were not different from either A or B groups. The interaction effect of frequency-amplitude combination and time point was significant. 0.71 MHz-100 mVpp combination was not included in the analyses since no alignment was observed.

The 0.71 MHz-100 mVpp group was excluded from the experimental design due to the lack of cell alignment as reported earlier. For the two-way ANOVA, the frequency-amplitude combination was included as one factor and time point as the other. Results show that the interaction effect of frequency-amplitude and the time point on hASC metabolic activity was significant (p=0.0031).

Whereas the hASC viability in the 0.71 MHz-200 mVpp group was lower than its untreated control (FIG. 8b) immediately after fabrication, the difference between their cell metabolic activities at day 2 was not statistically significant. As such, at day 2, there was no statistically significant difference in the hASC metabolic activity between any of the four groups. Moreover, for each group, the change in metabolic activity from day 2 to 4 was also not significant. The primary difference observed in this experimental design was between the 0.71 MHz-200 mVpp group and the 2 MHz-100 mVpp and control groups at day 4.

The effects of bioink viscosity and actuation duration on hASC viability and alignment characteristics were studied as part of Study 4. Previously, during Study 2, the bioink viscosity and actuation duration were held constant while assessing the effects of frequency and amplitude. For this study, all constructs were fabricated at 2 MHz and 200 mVpp while the bioink viscosity and actuation time were varied as per the experimental design.

Figure 11A:
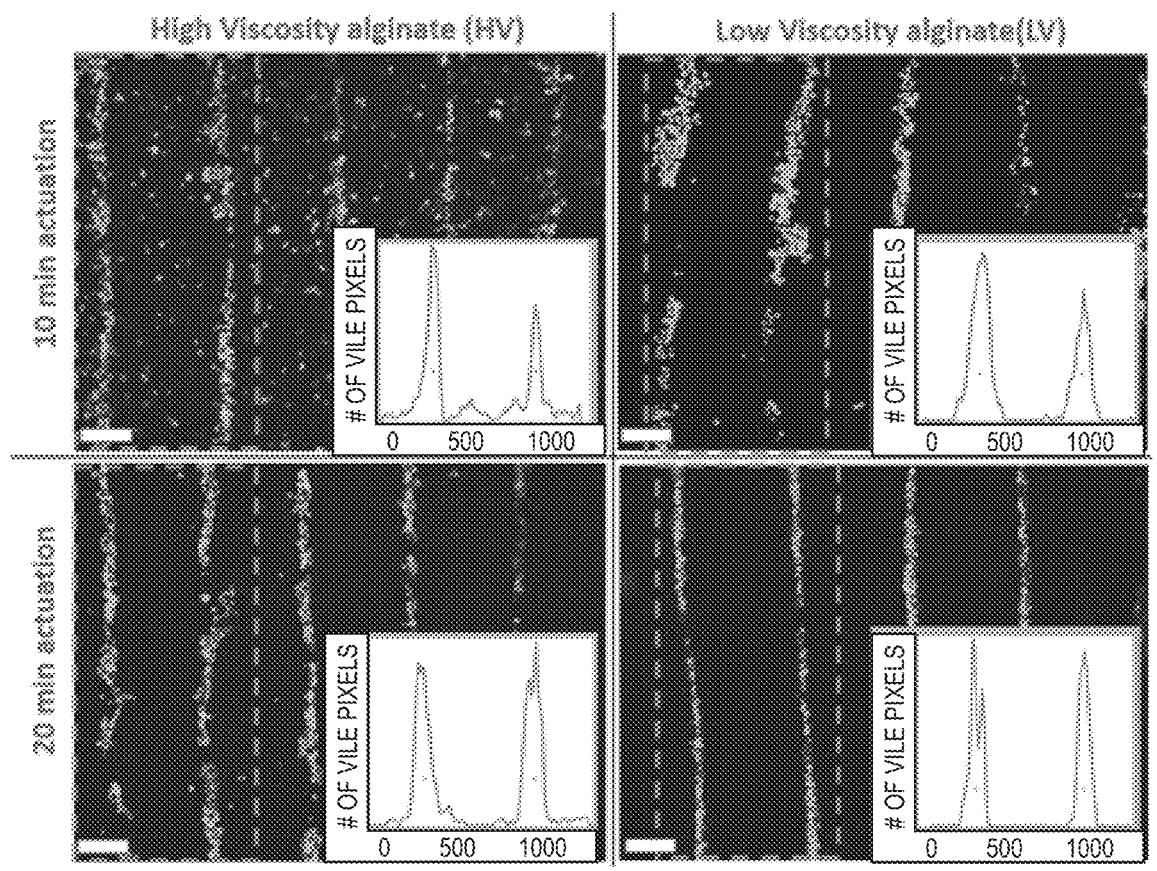
FIG. 11a illustrates representative live and dead images and intensity plots (insets) depicting the number of "live" pixels along 1 mm of the X-axis within the bounding box (red dotted rectangle) at a scale bar=250 µm; and, FIG. 11b illustrates a summary of variability in "live" pixels (inversely proportional to nodal concentration) from the experimental design, as provided in accordance with some embodiments of the presently disclosed subject matter.
Figure 11B:
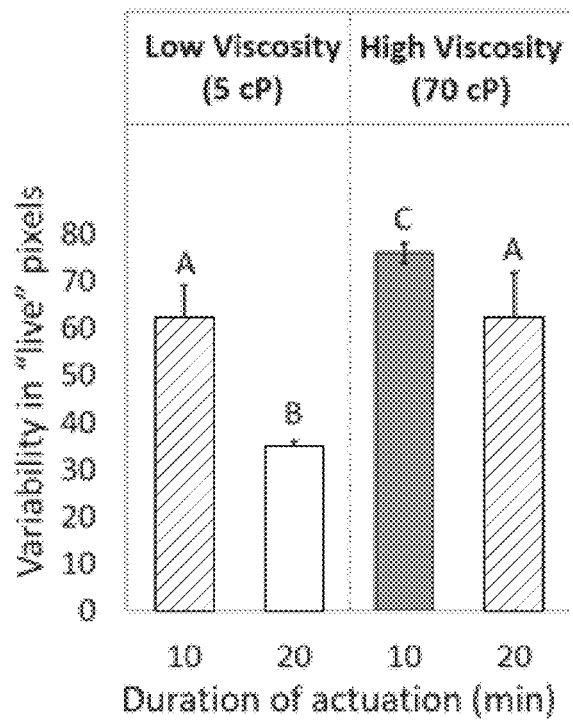

FIG. 11 depicts representative live/dead images of constructs of different treatment groups and a plot summarizing the nodal concentration data. FIG. 11a provides an illustration of representative live/dead images and intensity plots (insets) depicting the number of "live" pixels along 1 mm of the X-axis within the bounding box (red dotted rectangle) at a scale bar=250 μm. FIG. 11b illustrates a summary of variability in "live" pixels (inversely proportional to nodal concentration) from the experimental design. Groups denoted by A, B, and C were significantly different from each other (p<0.05). Both bioink viscosity and duration of ultrasonic actuation had a significant effect on alignment of hASC in alginate. The study found that viability was 100% across all groups, indicating that actuating 2 MHz transducers with 200 mVpp for up to 20 mins did not adversely affect the viability of aligned hASC in crosslinked bioinks of viscosities up to 70 cP. However, ANOVA results show that the main effects of viscosity and actuation duration on the nodal concentration were significant (p=0.0027 and p=0.0029, respectively). Among the four treatment groups, the hASC were most tightly clustered along the nodes or nodal planes in the low viscosity bioink after 20 min of actuation. At the other extreme, the spread of the hASC array was the widest in the high viscosity bioink with shorter actuation duration.

Figure 12A:
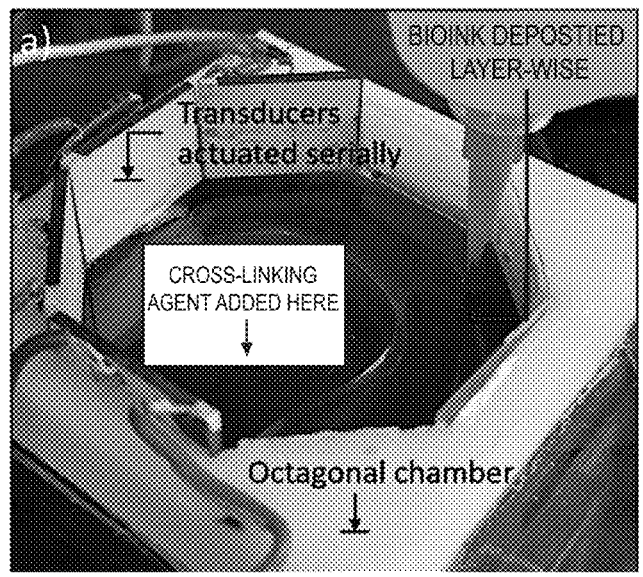
FIG. 12a illustrates a bioprinting (UABp) of a biomodeled human knee meniscus construct featuring circumferentially aligned cells wherein alginate-hASC bioink is bioprinted into the octagonal UAB chamber following the biomodeled tool-path.
Figure 12B:
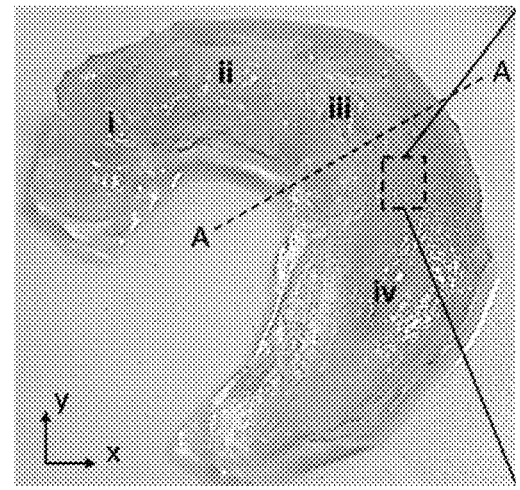
FIG. 12b illustrates a picture of the bioprinted construct; and, FIG. 12c illustrates a dissection microscope image depicting transition of alignment orientation of neutral red stained hASC, as provided in accordance with some embodiments of the presently disclosed subject matter.
Figure 12C:
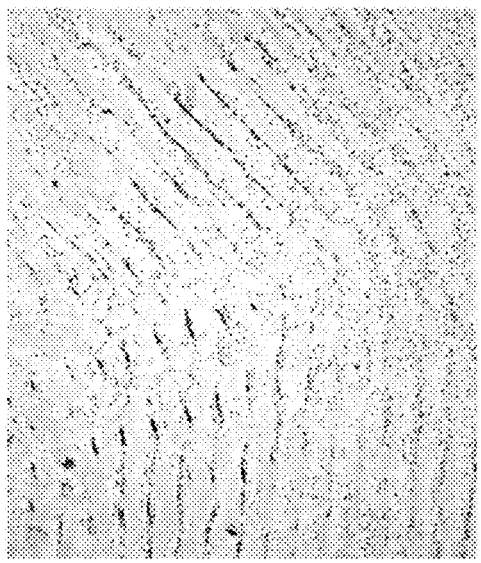
FIG. 12d illustrates a cross-sectional image depicting hASC alignment across multiple layers along the construct thickness; and, FIG. 12e-h illustrate representative fluorescence images highlighting four regions with differing cell alignment directions, as provided in accordance with some embodiments of the presently disclosed subject matter.

Multilayered meniscus construct with circumferential hASC alignment fabricated via UABp were studied as part of Study 5: FIG. 12 shows the meniscus construct with circumferentially-aligned hASC fabricated using UABp. FIG. 12a illustrates alginate-hASC bioink being bioprinted into the octagonal UAB chamber following the biomodelled tool-path. Transducers are actuated serially using high frequency relays with a switching time of 1 s, which aligns the cells before the patterns are entrapped via crosslinking. FIG. 12b illustrates the bioprinted construct. FIG. 12c provides a dissection microscope image depicting transition of alignment orientation of neutral red stained hASC between directions. FIG. 12d illustrates a cross-sectional image depicting hASC alignment across multiple layers along the construct thickness. The cross-section image of FIG. 12d accordingly highlights the non-linear arrangement of cell clusters along the construct thickness. This is induced by Rayleigh streaming, and is indicative of a greater compliance near the center of the transducers compared to its outer edges.

FIGS. 12e through 12h illustrate representative fluorescence images highlighting four regions with differing cell alignment directions. All images were captured with the same x-y reference axes at a scale bar=250 μm. Accordingly, the fluorescence images of the top view (FIGS. 12e through 12h) depict neutral red stained viable hASC clustering along nodes or nodal planes parallel to the faces of individual transducers.

Accordingly, embodiments of the presently disclosed subject matter introduce a new biofabrication and bioprinting process using ultrasound for non-contact manipulation of cells into physiologically relevant patterns in single and multilayered 3D hydrogel matrices. It is advantageous that the viability of cells not be adversely affected by the biofabrication process.

Embodiments presented herein further provide for the assessment of the interplay between moderate frequencies at higher amplitude and the resulting streaming on cell viability and metabolic activity over prolonged intervals to determine if the cells can recover from the immediate stresses encountered during UAB manipulation.

One of the advantageous aspects of the presently disclosed subject matter includes the corroboration of the underlying theory governing the alignment of cells suspended in the bioink using ultrasound. As explained above, results show that the alignment characteristics of the hASC arrays can be controlled via the acoustical parameters. The spacing between adjacent arrays of clustered cells (FIG. 9) (analogous to "inter-fiber spacing" in scaffolds) tallies with the theoretical spacing between adjacent pressure nodes (Table 1), and it is inversely proportional to the applied frequency. Furthermore, at a given frequency, the concentration of cells clustering along the pressure nodes or nodal planes (analogous to "fiber width" in scaffolds) is directly proportional to the frequency and voltage amplitude actuating the transducer (FIG. 9) and the actuation duration (FIG. 11) and inversely proportional to the bioink viscosity (FIG. 11). For example, at the 2 MHz frequency, the average width of the cellular arrays formed in the low viscosity bioink with 200 mVpp actuation for 20 min was 50 μm, in contrast to the average width of 65 μm and 108 μm noted in the high viscosity ink with 200 mVpp for 10 min and 100 mVpp for 20 min, respectively. The results of Studies 1-4 taken together signify that while using UAB, optimization of at least four critical parameters—bioink viscosity, frequency, amplitude, and actuation duration—is necessary in order to create tissue-specific patterns of interest while maintaining the viability and functionality of cells. By using the appropriate combinations of these parameters and bioink chamber designs with one or more transducer-reflector pairs, UAB provides the flexibility to produce controlled patterns of viable cells, which is a foremost step in creating engineered tissues with biomimetic ECM organization.

In moving towards tissue-specific applications, additional relevant parameters that will need to be characterized include the frequency of the burst mode of actuation and the type of cells and their concentration in the bioink. The inventors determined during pilot studies that burst mode actuation is critical to UAB because continuous actuation can adversely affect the transducer compliance characteristics over time. Continuous actuation also results in heat generation which can be detrimental to cells within the bioink. As such, the frequency of burst mode actuation can impact the UAB processing time and fidelity of the alignment patterns within constructs. With regards to the cell type, the size, density, and compressibility of cells will govern the radiation and drag forces that they experience, which in turn will dictate their alignment characteristics and functional responses to ultrasound. In addition to the characterization of a more comprehensive set of cellular, bioink and acoustical parameters and bioink chamber design to achieve high fidelity, high viability, tissue-specific patterns of interest, the UAB process (and its adaptations) can be further enhanced by optimizing the transducer design and constitution. By exploring appropriate impedance matching and in-process cooling strategies, better transducer compliance resulting in more uniform BUW generation can be achieved. This would help reduce the perturbations and Rayleigh streaming, thereby improving the cell viability.

This would also help linearize the currently scalloped profile of cell arrays along the nodes or nodal planes and improve the pattern fidelity.

A further advantageous aspect of the presently disclosed subject matter includes the demonstration of the UABp process that allows biomimicry at multiple length scales. Although 3D meniscal scaffolds have been investigated before, as the inventors understand, Study 5 is the first illustration of bioprinting a human medial knee meniscus construct with patient-specific macro-geometry and tissue-specific micro-architectural patterns of viable cells. This was achieved with an alginate bioink of higher viscosity than the ones used in preceding UAB experimental designs, which is in the viscosity range most relevant to bioprinting high fidelity structures. Although inventors have demonstrated UABp in the context of extrusion bioprinting, the underlying ultrasound-patterning principle can be extended to other forms of bioprinting including inkjet, laser-assisted, DLP and SLA-based techniques. Through astute bioink and process design and optimization, an extensive gambit of cellular patterns, for example, crisscross configuration in connective tissues or radial arrangement of hepatocytes in hepatic lobules, coupled with integration of multiple cell types in each layer is conceivable with UABp.

By successfully demonstrating non-contact 3D cell patterning in viscous hydrogels and mapping the process-structure relationships to achieve good fidelity and cell viability, embodiments of the presently disclosed subject matter can establish the foundation for creating biomimetic 3D tissues using UAB. Embodiments of the presently disclosed subject matter also provide for future studies focusing on UAB-based patterning of application-specific cell lines while investigating the bioink properties, inter-array spacing, and nodal concentrations to guide cellular morphology, differentiation and intercellular signaling to produce ECM that matches the hierarchical fibrous structure of mammalian tissues. With UAB, a non-reliance on chemotactic or physical cues for creating ECM alignment and a possibility of scalability and flexibility takes us a step closer to creating functional therapeutic engineered tissue substitutes.

The inventors have investigated the process of patterning cells in hydrogel matrices using BAW via a novel UAB platform design using computational modeling and experimental designs. The multiphysics model highlighted the effects of frequency and source signal amplitude on the acoustic pressure distribution, which were corroborated by the alignment characteristics of hASC arrays observed in the experimental studies. The experimental studies demonstrate that the bioink viscosity, frequency, amplitude, and actuation duration, and especially their interactions, impact the cell viability and alignment characteristics. The following should be noted: 1) the combinations of moderate frequency and high amplitude adversely affect cell viability, 2) the inter-array spacing is inversely proportional to the frequency, and 3) the nodal concentration is directly proportional to the amplitude and actuation duration and inversely proportional to the bioink viscosity.

Through the five studies, the inventors have laid out a process map of the process-structure interactions in UAB and discussed how the process design and fidelity of resulting patterned constructs can be enhanced moving forward. Embodiments of the presently disclosed subject matter accordingly provide for future studies focusing on investigating the effects of the UAB process parameters and cellular patterns on the organization and mechanical anisotropy of ECM secreted by patterned cells.

FIG. 13 through FIG. 20 further set of aspects of the presently disclosed subject matter. The methods and embodiments disclosed by way of FIGS. 13-20 further apply relationships between the SBAW frequency, alignment patterns, and cell viability determined via 3D multi-physics computational modeling and designed experiments with two types of cells (human adipose-derived stem cells (hASC) and human osteosarcoma cells (MG63)) within chemically-crosslinkable alginate and photo-crosslinkable gelatin methacrylate (GelMA) hydrogels. The vat photo-polymerization-based bioprinting of a multi-layered GelMA construct with cellular strands oriented in a 0-45-90° lay pattern across layers is also illustrated herein to highlight the layer-wise control offered by the process and its versatility.

The embodiments accordingly apply a bioprinting technique that uses ultrasonic standing bulk acoustic waves (SBAW) to align cells into controllable anisotropic patterns within viscous bioinks while maintaining high cell viability. A 3D computational model was developed by the inventors to discern the SBAW pressure pattern in response to multiple ultrasonic frequencies (0.71-2 MHz). Then, the alignment patterns and viabilities of human adipose-derived stem cells (hASC) and human osteosarcoma cells (MG63) in alginate as a function of the SBAW frequency was experimentally analyzed by the inventors. Computational results indicated the formation of parallel pressure strands with higher pressure amplitudes near the bottom of the deposited layer, which is corroborated by experimental images of cell alignment. The inter-strand spacing is found to be affected by the frequency (p<0.0001), while an interaction effect between the cell type and frequency governs the width of the strands (p=0.02). Further, the synergistic bioprinting and SBAW-induced patterning of hASC within alginate and gelatin methacrylate (GelMA) constructs in tandem with chemical and photo-crosslinking, respectively can be demonstrated. Pertinent cell alignment and viability of at least 80% were noted in the alginate and GelMA constructs across the experimental design space. Furthermore, the vat photo-polymerization-based bioprinting of a 3-layered GelMA construct with hASC strand lay pattern of 0-45-90° across the layers has also been demonstrated with respect to FIGS. 13 through 20.

Figure 13:
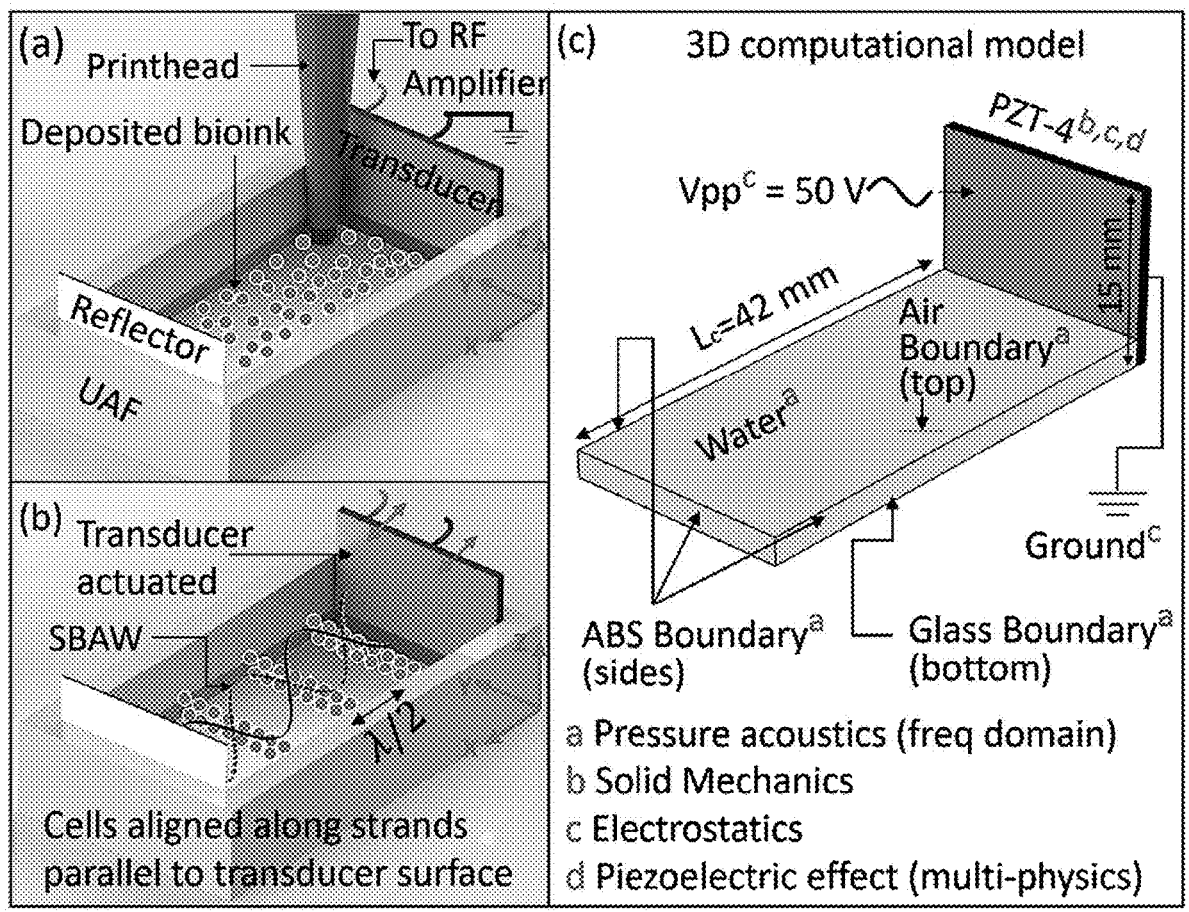
FIG. 13(a) illustrates an ultrasonic alignment fixture (UAF) for aligning cells in viscous bioinks.
FIG. 13(b) illustrates a SBAW pressure distribution within the UAF as it exerts radiation force on the cells to arrange them along straight strands; and, FIG. 13(c) illustrates a setup of the 3D linear acoustic model of the top view of the UAF illustrating the multi-physics interfaces in COMSOL, as provided in accordance with some embodiments of the presently disclosed subject matter.

FIG. 13 illustrates the process of using ultrasound to pattern cells along parallel strands within the bioink. Specifically, FIG. 13(a) illustrates an ultrasonic alignment fixture (UAF) for aligning cells in viscous bioinks, FIG. 13(b) illustrates a SBAW pressure variation within the UAF exerts radiation force on the cells to arrange them along straight strands, and FIG. 13(c) illustrates a setup of the 3D linear acoustic model of the top view of the UAF illustrating the multi-physics interfaces in COMSOL. According to at least one embodiment, the method utilizes an ultrasonic alignment fixture (UAF) that consists of an electroacoustic transducer and an opposing rigid reflector inside a hollow encasing. The bioink (fluid matrix with cells) is deposited within the hollow encasing, and the transducer is excited via a sinusoidal high frequency voltage signal. This excitation is in the form of ultrasonic frequency vibrations that create a longitudinal bulk acoustic pressure wave in the fluid. This pressure variation can be expressed as a combination of complex harmonic terms:

$$p(x,t)=A e^{i\omega(t-x/c)}+B e^{i\omega(t+x/c)} \tag{1a}$$

where, i is an imaginary number, ω is the angular frequency (ω=2πf, where f is the ultrasonic frequency) and c is the speed of sound in the bioink. In Eq. (1a), the first and second term with their associated scalar coefficients (A and B) represent pressure waves travelling in the positive and negative x-direction (emitted and reflected waves, respectively), with p(x,t) being the resulting interference. A and B can be solved for using the boundary conditions of spatially non-varying pressure at the transducer end (x=0) and a zero spatial pressure gradient at the reflective end (x=L):

$$p(0,t)=P_0 e^{i\omega t} \quad (2a)$$

$$\partial p/\partial x \text{ (at } x=L)=0 \quad (3a)$$

where $P_0$ is the pressure amplitude. Solving these boundary conditions results in the SBAW with pressure varying only along the x-axis (since the transducer excitation is along the x-axis), given by:

$$p(x,t)=P_0 \cos(\omega t)\cos(\omega x/c) \quad (4a)$$

The nodes of this pressure variation are planes parallel to the transducer-reflector surfaces and are spaced out by $\lambda/2$, where 2 is the ultrasound wavelength (c/f). Eq. (4a) is followed up with a boundary condition on the transducer-reflector distance given by:

$$LSW=n\lambda/2 \quad (5a)$$

where n (an integer) denotes the number of pressure nodes. This imposes a design constraint on the UAF, wherein LSW needs to be an integer multiple of half the wavelength for a successful formation of SBAW. For speed of sound in water (c=1500 m/s), an LSW of 42 mm suffices the design constraint for the four frequencies that will be computationally and experimentally investigated in this work (0.71, 1, 1.5, 2 MHz). Once the SBAW is created, the resulting acoustic radiation force (ARF) exerted on the cells suspended in the bioink causes them to traverse and align at the nearest pressure nodes. This force is given by:

$$ARF=(\pi/3c)(ks-kc)r^3 \omega P0^2 \sin(2\omega x/c) \quad (6a)$$

where ks and kc are the compressibility of bioink and cell, respectively, and r is the cell radius. From Eq. (6a), it is evident that the ARF would increase by increasing the frequency, pressure amplitude, and the radius of the cell. In viscous bioinks, the movement of a cell towards the nearest pressure node due to the ARF would be slowed down by viscous drag force (DF) from the bioink, given by:

$$DF=6\pi\eta rv \quad (7a)$$

where $\eta$ is the dynamic viscosity of the bioink and v is the instantaneous velocity of the cell. Greater ARF amplitude would increase the rate of movement of the cells, thereby increasing the DF. This may increase the shear forces on the cells, in turn, affecting their viability.

According to at least one embodiment, the UAF encasing was 3D printed out of acrylonitrile butadiene styrene (uPrint SE Plus, Stratasys, MN) and attached onto a glass substrate using a biocompatible glue (MG30, Infinity Bond Adhesives). The same glue was then used to attach an electroacoustic transducer (piezo-ceramic plate type, SM 111 material, Steiner & Martins Inc, FL) as the wave generating surface and a glass cover slip (BRAND®, Millipore Sigma, Burlington, Mass.) as the rigid reflector on opposite ends of the encasing. The sinusoidal voltage signal to excite the transducers was generated from a function generator (Keysight Technologies Inc., CA) and amplified from an RF amplifier (Electronics & Innovation Ltd., NY).

To determine the pressure variation patterns and amplitudes, which would subsequently govern the corresponding cellular patterns and viability characteristics, a 3D finite element analysis (FEA) model was formulated in the Acoustic-Piezoelectric interaction interface in COMSOL Multiphysics® (Comsol Inc., MA). The interfaces were setup as shown in FIG. 13(c). Since both alginate and GelMA solutions contain at least 95% water, the liquid between the transducer and reflector was assigned as water with sound attenuation per unit length (dB/m) dependent on frequency. To the boundaries of the liquid domain not contacting the transducer, a material dependent acoustic impedance (Zm) was assigned as:

$$Z_m=\rho_m c_m \quad (8a)$$

where $\rho m$ is the density of the medium that water is in contact with at that boundary, and cm is the speed of sound in that medium. These boundaries constituted 3D printed ABS at the sides ($\rho_{m(ABS)}$=1070 kg/m³ and cm(ABS)=2230 m/s), glass at the bottom ($\rho_{m(glass)}$=8000 kg/m³ and $c_{m(glass)}$=4540 m/s) and air at the top ($\rho_{m(air)}$=1.22 kg/m³ and $c_{m(air)}$=343 m/s).

In the solid mechanics and electrostatics interfaces, manufacturer-defined compliance attributes were assigned to model the deformation characteristics of the electroacoustic transducer. These included an isotropic structural loss factor of 1/1800, a dielectric dissipation factor of 0.4, and coefficients of the stiffness matrix (cE) and coupling matrix ($e^T$) of $c_{E(11)}$=$c_{E(22)}$=86 GPa, $c_{E(33)}$=73 GPa, $c_{E(66)}$=172 GPa, and $e^T_{(31)}$=$e^T_{(32)}$=−12.4 C/m², $e^T_{(33)}$=23.36 C/m², respectively, in the stress charge form of transducer compliance:

$$T=c_E S+e^T E \quad (9a)$$

where T is the stress exhibited by the transducers, and S and E are the strain and applied electric field, respectively. To the transducer surface contacting water, a harmonic perturbation having voltage amplitude of 25 V was applied, while the other surface was grounded. A fixed constraint was also applied to the transducer at the grounded surface. For the entire model, at each frequency (0.71, 1, 1.5, 2 MHz), a mapped rectangular mesh with maximum element size of 0.03 mm (<$\lambda$/10 at each transducer frequency) was used to achieve convergence. The model was computed for four separate 3D setups, each having transducer thickness dependent on the resonant frequency as per the manufacturer specifications. On a desktop computer with 32 GB of RAM and 16 GB of dedicated graphics, the computation for each geometry with approximately 4.5×10⁶ degrees of freedom lasted approximately 13 minutes.

In terms of the bioink preparation for preparing the cells, cryopreserved hASC (R7788115, Thermo Fisher Scientific, MA) or MG63 (CRL®1427™, ATCC, VA) were plated in T-75 flasks (Nunc™ Easy Flask™, Thermo Fisher Scientific). The hASC were proliferated in MesenPro RS basal media with growth supplement (Thermo Fisher Scientific) and 1% L-Glutamine (Thermo Fisher Scientific). The MG63 cell media comprised of 90% v/v minimum essential medium without L-glutamine (MilliporeSigma, MA) and 10% v/v fetal bovine serum (Thermo Fisher Scientific). The T-75 flasks were incubated at 37° C. and 5% $CO_2$ with media changes on alternate days until 80% confluency.

The cells used for the first set of experiments to study alignment characteristics in alginate were stained using neutral red dye (MilliporeSigma). These cells were incubated in 5 ml of filter sterilized cell growth media supplemented with 5 mg of dye for 45 min. The cells were then harvested using TrypLE Express enzyme (Gibco, Thermo Fisher Scientific) and spun at 100 g for 5 min to form a cell pellet.

For the set of experiments to analyze cell viability via Live/Dead® assay 3 hours post-bioprinting, the cells were not stained with neutral-red dye, since this dye would have confounded the results of the viability assay by labeling all viable cells fluorescent in the red emission spectra.

The alginate matrix constituted a 2% w/v solution of high molecular weight alginate powder (Manugel® GMB, DuPont, DE) in PBS (MilliporeSigma). After adding the powder to PBS, the solution was rigorously vortexed for 10 second, sonicated for 5 min, and then autoclaved at 121° C. and 16 psi for 30 min to form the sterile alginate matrix ($\eta$~70 cP). It was then stored at 37° C. until further experiments.

The GelMA matrix ($\eta$~30 cP at 37° C.) comprised of 5% w/v sterile GelMA containing 0.25% w/v LAP photo-initiator (CELLINK, Gothenburg, Sweden). The GelMA was stored at 4° C. until the day of the experiment and equilibrated at 37° C. for 30 min prior to the bioink preparation.

To formulate the bioinks, the supernatant media atop the cell pellet was gently aspirated, followed by addition of appropriate volumes of alginate or GelMA solutions. The bioinks were constituted with a concentration of 1 million cells/ml using gentle pipetting.

The inventors characterized the progression of alignment over time in alginate first because it is more viscous of the two bioinks, and successful cell alignment in alginate would ensure alignment in GelMA. Towards this, three separate UAFs were made for each frequency group to align the neutral-red stained cells and assess two alignment pattern characteristics—inter-strand spacing and strand width. During these experiments, the UAFs were filled with 4 ml of PBS and kept on the imaging platform with bottom illumination within a dissection microscope (EZ4, Leica Microsystems, Germany). 1 ml of the bioink was subsequently deposited and allowed to disperse for 30 seconds. A sinusoidal voltage signal with amplitude of 25 V, applied in intermittent bursts of 1 second with 1 second pauses, was applied to the transducer to create well-defined cellular strands within 1 min of excitation at each of the four frequencies for each of the two cell types. Top view images were captured at 0 second (time of commencement transducer excitation) and 60 seconds. From the images captured at 60 seconds, inter-cellular strand spacing (distance between centroids of adjacent strands) and strand width (horizontal distance between extremities of each strand) were measured using custom MATLAB (Mathworks, MA) scripts. For each frequency and cell type, these inter-strand spacing and strand widths were determined at three randomly selected locations per image from three images per sample for three independently fabricated samples (i.e., n=27 data points per group).

After characterizing the fundamental alignment characteristics based on variations in ultrasonic frequency and cell type, the inventors investigated the persistence of alignment and cell viability in 3D cellular constructs following synergistic bioprinting, ultrasonically-induced alignment, and bioink crosslinking in the second study. The alginate and GelMA constructs were bioprinted in a commercial bioprinter (CELLINK) and crosslinked via chemical- and photo-crosslinking methods, respectively, at the four aforementioned frequencies. These experiments were performed using hASC-based bioinks, since these non-cancerous cells are being extensively utilized for therapeutic tissue engineering research and applications.

In preparation for bioprinting, the UAF was setup on the bioprinter build platform, and 3 ml of the bioink (alginate or GelMA) was loaded into a 3 ml syringe extruder cartridge (BioX, CELLINK). Another 10 ml cartridge was filled with 4 ml of filter sterilized 1% w/v $CaCl_2$ in PBS to be used for crosslinking the alginate. A 22G nozzle (inner Ø=0.72 mm) was attached to the bioink cartridge, while a 30G nozzle (inner Ø=0.16 mm) was used for the low viscosity crosslinker.

To fabricate the alginate constructs, 2 ml of bioink (at 37° C.) was printed into UAF pre-filled with 4 ml of PBS as adjacent strands in a 20×40 mm geometry at an extrusion pressure of 3 kPa and print speed of 10 mm/s. In tandem, the transducer was actuated by a 25 V sinusoidal voltage signal in bursts of 1 second followed by 1 second pauses. This was commensurate with the outcomes of the previous alignment study. The burst mode of excitation especially helped to minimize the impedance heating of the transducer and any deleterious effects thereof. After 1 min of excitation, 4 ml of the crosslinker was printed into the UAF at the rate of 1 ml/min achieved through an extrusion pressure of 16 kPa and print speed of 10 mm/s. The presence of PBS in the fixture during crosslinking ensured uniform dispersion of the $Ca^{2+}$ gelation ions. The transducer excitation was maintained for 5 min during the progression of crosslinking (15 min), which enabled the retention of cells in their aligned positions within the bioink. After 15 min of crosslinking, the construct was retrieved from the fixture using flat-headed forceps and subject to further assessment.

The general bioprinting protocol for GelMA constructs was similar, except that the fixtures were not pre-filled with PBS, and UV exposure was used instead of $CaCl_2$ to crosslink the constructs. Briefly, 2 ml of bioink at 37° C. was printed into the UAF at an extrusion pressure of 2 kPa and print speed of 10 mm/s, followed by excitation of the transducer (25 V sinusoidal voltage with 1 second bursts). After 1 min of excitation, the bioink was crosslinked by exposure to 405 nm UV, with a separation of 50 mm between the in-built UV LED and the dispensed bioink. The transducer excitation was switched off after 5 min while the UV exposure was allowed to continue up to 15 min, and the crosslinked construct was retrieved using flat headed forceps. The average thickness of the alginate and GelMA constructs was 2.5 mm.

The constructs containing neutral-red stained cells were imaged using a DSLR camera (EOS 80D, Canon, Japan). The constructs containing non-neutral-red stained cells (n=3 per group) were gently transferred to a 100 mm petri dish and incubated in 10 ml culture media for 3 hours. This step was necessary to ensure that the cells were able to recover from prior processing steps before analyzing their viability. After 3 hours, the viability assessment was performed using Live/Dead assay (Life Technologies, CA). Herein, the media was aspirated followed by addition of 2 ml of PBS containing 4 μl EthD-I and 1 μl calcein AM over the constructs. The constructs were then incubated for 30 min, and each construct was subsequently imaged at three randomly-selected locations using a fluorescent microscope (DM5500B, Leica Microsystems, Germany) The corresponding average % cell viability was determined for each group based on image analyses of live (green emission spectra) and dead (red emission spectra) cells using a custom MATLAB script.

To demonstrate/verify the versatility of the ultrasound-alignment approach, the inventors created a UAF variant by attaching three 2 MHz transducer-reflector pairs on a petri dish such that the pairs were angled relative to each other in increments of 45°. Therefore, if one pair was assigned the orientation 0°, the other pairs had orientation of 45° and 90°, respectively. A corresponding LSW of 54 mm was used to satisfy Eq. (5a) and successfully induce the SBAW. The transducers were excited via high frequency relays (G6K 2P RF, Omron Electronics LLC, IL) controlled by a microcontroller (Arduino Uno) that switched on the relevant relay, thereby exciting the corresponding transducer, as per the orientation required for a particular layer. This setup was utilized to bioprint a 3-layered GelMA construct via vat photo-polymerization, with cells aligned along 0°, 45° and 90° in the three layers, respectively. The cells can be aligned in any other angles between 0° and 180° as required by the application at hand.

To estimate the alignment characteristics of cells in this setup prior to the experiment, a 2D linear-acoustic computational model of the top view of the UAF with the three transducer-reflector pairs was setup in COMSOL. A 3D model similar to the one described previously was highly computationally intensive, and hence not practical. In the 2D model, the transducer compliance characteristics were the same as those used above, while the outer edges of the liquid (water) domain were assigned a sound hard boundary condition. A free tetrahedral mesh of maximum element size of 0.03 mm was used to achieve convergence. With $2 \times 10^7$ degrees of freedom, the solver computed the solution in approximately 35 min.

To fabricate the construct, first, 5 ml of GelMA bioink (1 million neutral-red stained hASC/ml) at 37° C. was deposited into the UAF, resulting in a layer height of 1.5 mm Transducer #1 was then excited at 25 V amplitude in burst mode, and the cells were allowed to align for 1 min A 405 nm 100 mW UV laser (405MD-100-1445, Q-Baihe) was subsequently traversed at 2 mm/s at a height of 30 mm above the GelMA layer to selectively crosslink a $20 \times 20$ mm$^2$ construct with hASC aligned and entrapped along the 0° orientation. Similarly, 5 ml of GelMA was deposited for layers 2 and 3, and transducers #2 and #3 actuated, respectively, with subsequent selective crosslinking to create the layers with cells aligned and entrapped along 45° and 90° orientation, respectively. The overall construct dimensions, therefore, were $20 \times 20 \times 4.5$ mm$^3$. The neighboring uncrosslinked bioink was then aspirated and the construct carefully extracted using flat-headed forceps for further imaging.

Two-way ANOVA and Tukey post-hoc tests were used to assess the effects of frequency (0.71, 1, 1.5 and 2 MHz) and cell type (hASC and MG63) on the alignment characteristics (inter-strand spacing and strand width) of cells in alginate (n=3 per group) in the first study. Similarly, two-way ANOVA and Tukey post-hoc tests were used to assess the effects of frequency (0.71, 1, 1.5 and 2 MHz) and bioink type (alginate, GelMA) on the viability of the aligned hASC (n=3 per group) in the bioprinted crosslinked constructs in the second study. All tests were performed in JMP® (SAS, Cary, N.C.) and statistical significance assessed at $\alpha = 0.05$.

Figure 14:
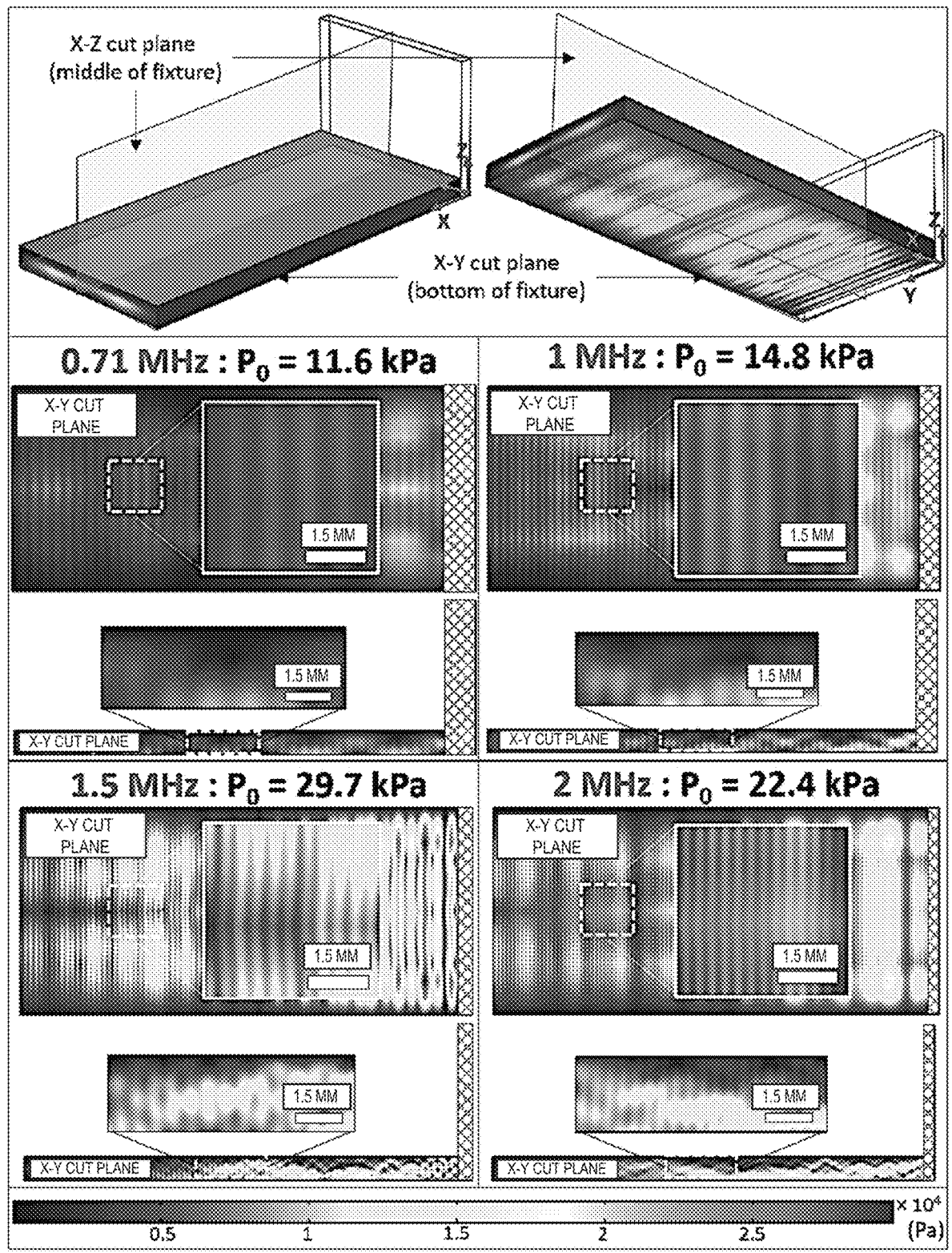
FIG. 14 illustrates acoustic pressure distribution in UAF as seen in 3D (top panel) and corresponding cut sections along x-y and x-z planes for analysis, as provided in accordance with some embodiments of the presently disclosed subject matter.
Figure 15:
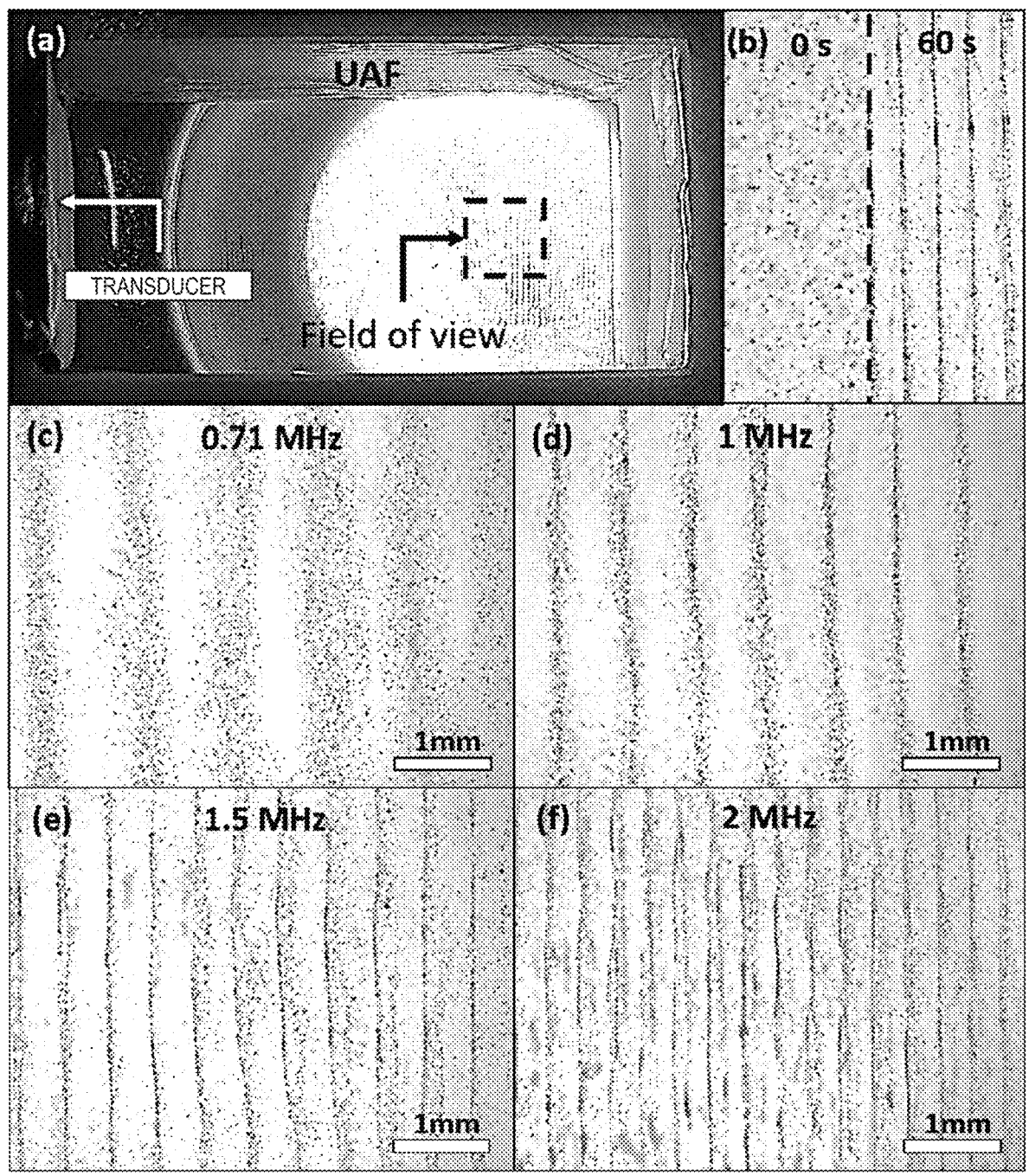
FIG. 15(a) illustrates a top view of UAF at 2 MHz.
FIG. 15(b) illustrates the alignment of hASC in alginate over 60 seconds in the 2 MHz fixture; and, FIGS. 15(c-f) illustrate hASC aligned within alginate at SBAW frequencies of 0.71, 1, 1.5, and 2 MHz, respectively, after 60 seconds of actuation, as provided in accordance with some embodiments of the presently disclosed subject matter.
Figure 16:
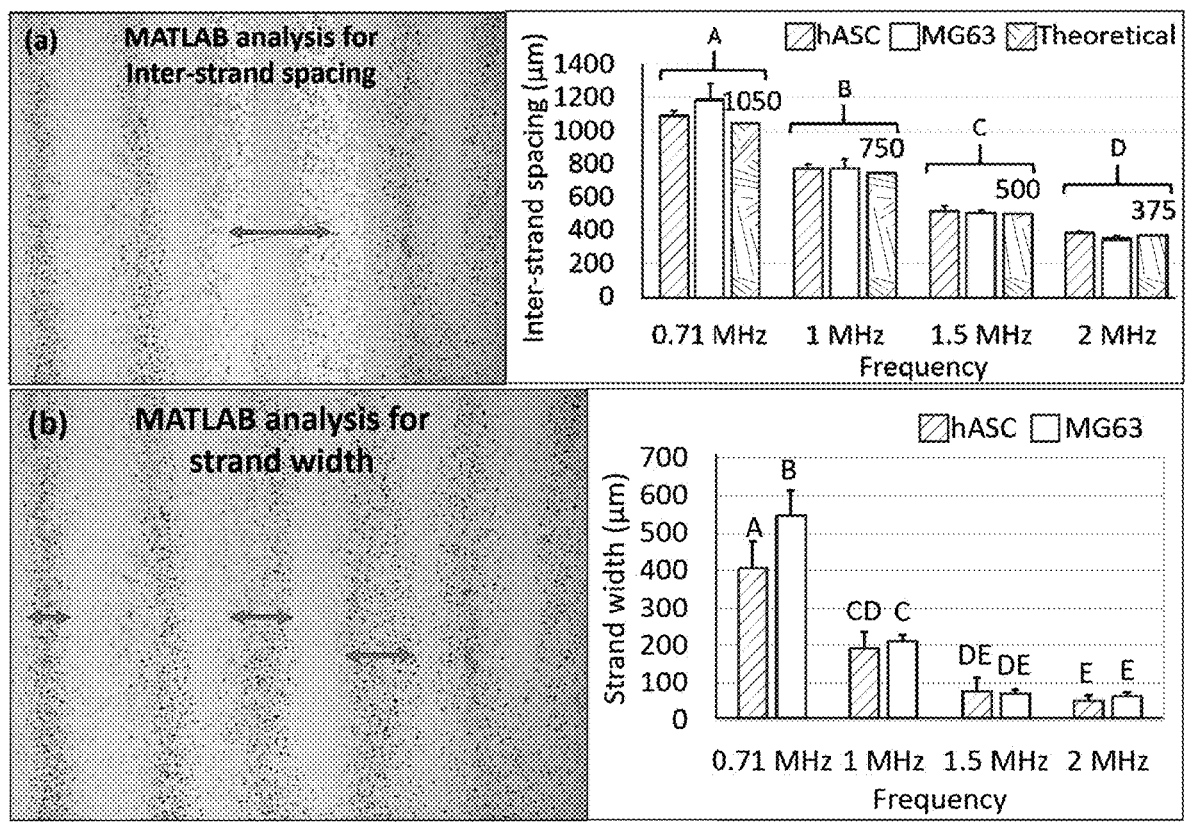
FIG. 16(a) illustrates a representative example of an output of MATLAB image analysis to determine inter-strand spacing based on centroid-centroid distance of adjacent strands of clustered cells (left), and corresponding results (right), as provided in accordance with some embodiments of the presently disclosed subject matter.
FIG. 16(b) illustrates a representative example of MATLAB image analysis to determine strand width as the distance between the extremities of individual strands of clustered cells (left), and corresponding results (right), as provided in accordance with some embodiments of the presently disclosed subject matter.

The computational results of variation of acoustic pressure in the UAF with respect to frequency are shown in FIG. 14. FIG. 14 accordingly illustrates acoustic pressure distribution in UAF as seen in 3D (top panel) and corresponding cut sections along x-y and x-z planes for analysis. Pressure distribution pattern along the x-y section (bottom view) depicts straight nodal lines at each frequency in accordance with the theory. The x-z sectional view elucidates the non-uniform pressure distribution along the depth of the fluid, with greater radiation pressures estimated near the glass bottom of the fixture. The relationship between frequency and pressure amplitude was non-linear, with the highest amplitude noted at 1.5 MHz and lowest at 0.71 MHz. In each fixture, the red-hatched pattern denotes the transducer, which had different thickness specific to each resonant frequency.

Whereas the pressure nodes manifest as uniform planes parallel to the transducer surface in theory, the computational results highlighted a pressure distribution pattern varying across the depth of the fluid, with larger pressure amplitudes at the bottom of the fixture, and almost zero pressure near the top. To better visualize this pressure distribution, two separate sections were taken—one along the x-z plane at the center of the UAF and another at the bottom of the UAF along the x-y plane. The pressure distribution in the bottom view (x-y plane) depicted straight nodal lines in accordance with the theory. The peak pressure amplitudes followed a non-linear relationship with respect to the frequency in decreasing order for 1.5 MHz (29.7 kPa), 2 MHz (22.4 kPa), 1 MHz (14.8 kPa), and 0.71 MHz (11.6 kPa), respectively.

At the boundaries of the fluid domain, a portion of the pressure wave emanating from the transducer (pi) gets reflected back into the fluid. The pressure of this reflected wave (pr) can be given as:

$$pr(x,t) = pi(x,t)(Zm - Zf)/(Zm + Zf) \quad (10a)$$

where Zf is the acoustic impedance of fluid, which in this case is water ($\rho f = 1000$ kg/m$^3$ and cf=1500 m/s). At the air-water boundary in the computational model, the acoustic impedance of air is negligible compared to that of water (Zm(air)<<Zf), which leads to an almost 180° out of phase reflection of the incident pressure wave as per Eq. (10a). The resulting interference yields the zero-pressure region at the top of the fluid domain (near the air-water boundary).

Upon application of the sinusoidal voltage signal, the resulting SBAW due to transducer vibration slowly aligned the cells at their nearest pressure nodes to form cellular strands. FIG. 15(a) illustrates a top view of UAF at 2 MHz. FIG. 15(b) illustrates the alignment of hASC in alginate over 60 seconds in the 2 MHz fixture. FIG. 15(c)-(f) illustrate hASC aligned within alginate at SBAW frequencies of 0.71, 1, 1.5, and 2 MHz, respectively, after 60 second of actuation. The alignment characteristics of MG63 cells were found to be similar to those of hASC. The progression of hASC alignment over 60 seconds is evident in FIG. 15(b). Although the pressure amplitude at 0.71 MHz was approximately an order of magnitude less than that at 1.5 MHz, distinct and measurable cellular alignment was observed after 60 seconds of actuation, nonetheless.

FIG. 16(a) illustrates a representative example of an output of MATLAB image analysis to determine inter-strand spacing based on centroid-centroid distance of adjacent strands of clustered cells (left), and corresponding results (right), which indicate a significant effect of frequency (p<0.0001) on the spacing. The spacing at each frequency was closely correlated with the theoretical spacing ($\lambda/2$), irrespective of the cell type. FIG. 16(b) illustrates a representative example of MATLAB image analysis to determine strand width as the distance between the extremities of individual strands of clustered cells (left), and corresponding results (right), which indicate a significant effect of the interaction of frequency and cell type (p=0.02) on the spacing. Letters A-D denote statistically significant post-hoc differences (p<0.01). As per results of the two-way ANOVA, the inter-strand spacing was significantly affected by the frequency (p<0.0001), and not by the cell type (p=0.98) or their interaction (p=0.058). Post-hoc results indicate that the spacing at each frequency was independent of the cell type, but for each cell type, spacing at each frequency was significantly different (p<0.01). The spacings also closely correlated with the theoretical spacing ($\lambda/2$), which is indicative of a high degree of controllability of the spatial distribution of the cells by altering the ultrasonic frequency. Results of two-way ANOVA show a significant interaction effect of cell type and frequency on the strand width (p=0.02). Corresponding estimates for strand width were highest at 0.71 MHz, which can be attributed to the smaller acoustic pressures at that frequency and a greater distance of traversal from the pressure antinode to the nearest node ($\lambda/4$) in the SBAW. The estimates of the widths were lower at 1.5 and 2 MHz on account of the higher acoustic pressure (at 1.5 MHz) and smaller traversal distance between the antinode and the nearest node (at 2 MHz). Comparing between hASC and MG63 cells, it is evident that the strand width was different between the two cell types only at 0.71 MHz (p=0.013). Herein, the relatively smaller strand width with hASC can be attributed to its comparatively larger cell radius, which results in these cells traversing and clustering faster due to higher radiation force. As per Eqs. (6a) and (7a) and literature, the increase in radiation force due to increase in radius is higher ($ARF \propto r^3$) than the corresponding increase in the drag force ($DF \propto r$), thereby resulting in smaller alignment times.

At any given cell concentration in the bioink, larger strand width would denote less dense packaging of the cells within their respective strands. A lesser cell density within individual strands may lead to an unaligned ECM formation due to the lack of relevant inter-cellular signaling cues. Towards this, smaller widths could be achieved by increasing the pressure amplitude (by increasing the voltage amplitude to the transducer). This could, however, increase the radiation pressure (and hence ARF), which would, in turn, increase the viscous drag on the cells, possibly affecting their viability.

Another alternative for reducing the strand width would be to allow cells more time to traverse to the nodes by delaying the time of introduction of the crosslinking mechanism. However, an important nuance to be noted is that too much delay in crosslinking initiation may cause the cells to settle down towards the bottom of the layer in their respective strands due to gravity, resulting in the loss of three-dimensionality of cell alignment (cells aligned across parallel planes). Therefore, a synergy of computational modeling and experiments, similar to the one described in this study, could be used to pre-determine the pressure amplitudes that are non-deleterious to the cells, and that would still result in cells aligning in parallel planes across each layer, with large enough cell densities (smaller width) to induce aligned ECM throughout the layer.

In conjunction with the strand width, it may be advantageous to allow sufficient gap between the strands to minimize cells within adjacent strands from bridging the gap and producing unaligned ECM fibers. The gap, however, cannot be too large or the ECM fibers will be too far apart, resulting in poor mechanical characteristics. Since the gap between the strands is a function of both inter-strand spacing and the strand width, it could be controlled by controlling the SBAW frequency (to control the inter-strand spacing), and its combination with the pressure amplitude and crosslinker initiation delay (to control the strand width). Such effects of the interplay of strand width and inter-strand spacing towards tissue-specific ECM organization can provide for additional advantageous aspects.

Figure 17:
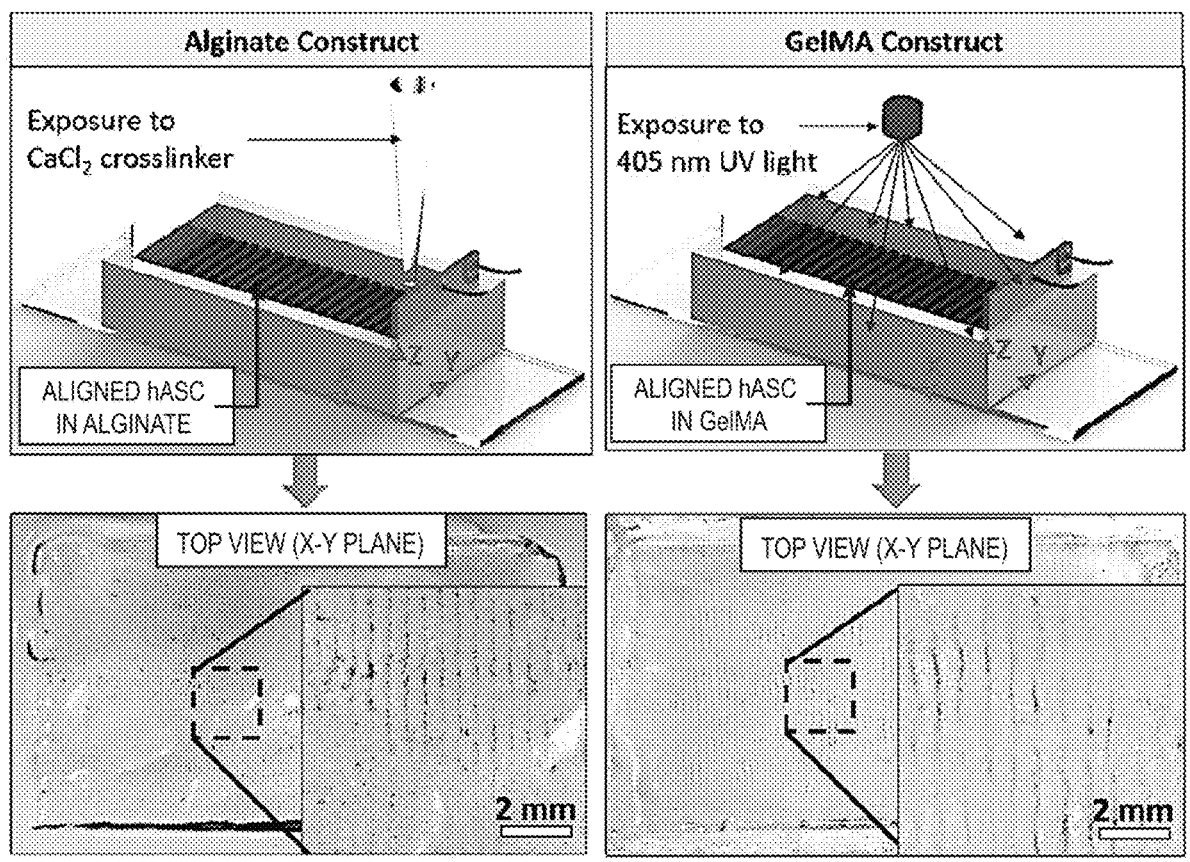
FIG. 17 illustrates crosslinking methods involving exposure to $CaCl_2$ or 405 nm UV light to crosslink alginate or GelMA, respectively, as provided in accordance with some embodiments of the presently disclosed subject matter.

FIG. 17 illustrates crosslinking methods involving exposure to $CaCl_2$ or 405 nm UV light to crosslink Alginate or GelMA, respectively. The corresponding crosslinked constructs with aligned cells depict preservation of alignment across the macro-geometry of the construct. FIG. 17 accordingly demonstrates the entrapping of aligned neutral red stained hASC within chemically crosslinked and photo-crosslinked constructs of alginate and GelMA fabricated via synergistic bioprinting and SBAW-assisted alignment. Since the neutral red dye selectively stains live cells, exhibition of redness in the cells post-bioprinting is indicative of the non-deleteriousness of the process.

Figure 18:
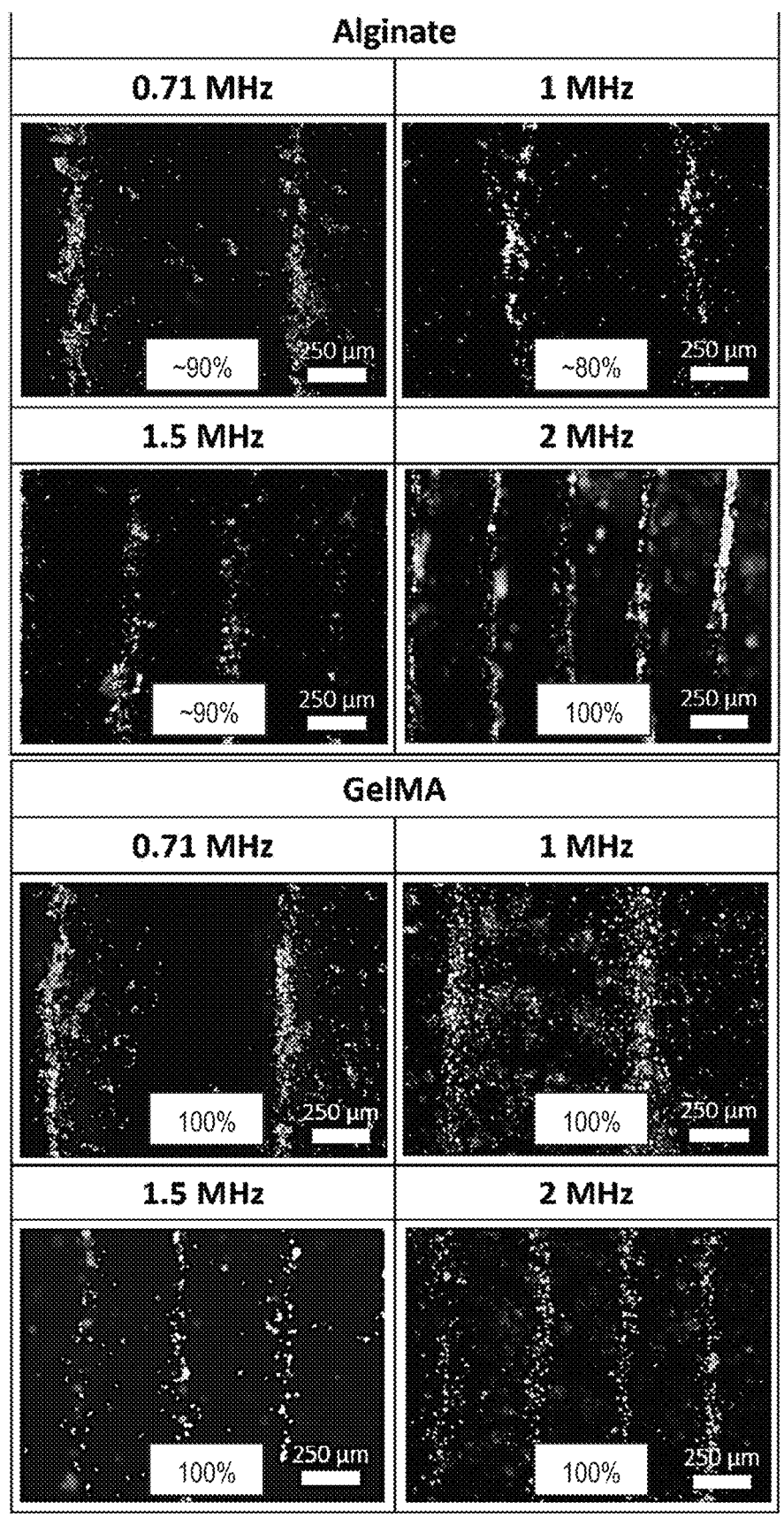
FIG. 18 illustrates representative Live/Dead® images of cells aligned within crosslinked alginate and GelMA constructs, as provided in accordance with some embodiments of the presently disclosed subject matter.

Representative live/dead images from the viability analysis of crosslinked constructs of both bioinks are shown in FIG. 18. Recall that the hASC used in this subset of experiments were not neutral-red stained. A viability of 100% was noted in all GelMA groups, while the viability of the alginate groups varied from 80-100%. Results of two-way ANOVA show a significant effect of the interaction of bioink type and frequency (p<0.0001) on the hASC viability. Post hoc tests within alginate indicate that the viability at 1 MHz was significantly lower than that of the other three groups. Furthermore, the viability at 0.71 MHz and 1.5 MHz were also significantly different than that at 2 MHz. To explain this non-linear trend of viability, three key factors can be considered—acoustic cavitation effects, fluid streaming-induced perturbations, and shear forces on the cells due to the viscous drag. Cavitation occurs when dissolved gas bubbles expand and collapse during the transducer excitation bursts, thereby creating localized surge in temperature and pressure, which has been demonstrated to rupture cell membranes. These effects were found to be higher at lower frequencies and higher pressure amplitudes. Streaming-induced perturbations occur when the transducer deformation is non-uniform across its surface due to manufacturing defects, thereby creating differences in acoustic pressures within the contacting fluid. These effects were found to be higher at moderate frequencies and may cause vortexing effects that may be deleterious to the cells. Lastly, larger radiation force acting on the cells increases their speed of migration to the node, thereby increasing the viscous drag and hence the shear forces on their cell membranes. These shear forces would be more enhanced for more viscous bioinks such as alginate than GelMA, resulting in comparatively lower viability at some frequencies. Across the four frequencies in alginate, the reduced viability at 0.71 MHz could be primarily attributed to the increased cavitation effects. The 1 MHz group exhibited higher radiation pressures than 0.71 MHz and thus could have been more susceptible to cavitation effects. Moreover, this group also exhibited increased streaming-induced perturbations, which, coupled with the effect of cavitation, could explain the lowest observed viability. Finally, the 1.5 MHz group was associated with the highest radiation forces (due to highest radiation pressures) and therefore increased shear forces on the migrating cells which may have lowered their viability. Nevertheless, a viability of at least 80% can lie within the acceptable range for tissue engineering applications, and the cell viability could potentially improve if the constructs are matured further under appropriate culture conditions inside a perfusion bioreactor.

To further improve the viability in the alginate groups that demonstrated less than 100% viability, the key would be to reduce the acoustic radiation pressure acting on the cells, thereby reducing their speed of traversal to the node and the corresponding drag forces acting on them, as well as the cavitation effects. This could primarily be achieved by reducing the voltage amplitude to actuate the transducer. However, it should be noted that there will be a practical lower limit on the voltage amplitude to still achieve alignment. This will be the voltage amplitude at which the acoustic radiation forces are large enough to result in reasonable alignment times as per the process and application. For example, for a voltage amplitude lower than 25 Vpp, initiation of the crosslinking would have to be deferred by more than the 1 min interval used in this work. To further improve viability, cavitation effects could also be lowered by use of surfactants, or by smaller actuation bursts to prevent large bubble formation in the bioinks. To prevent fluid streaming-induced perturbations, custom-made transducers with more uniform surface deformation (compliance) characteristics could be developed.

FIG. 18 illustrates representative Live/Dead® images of cells aligned within crosslinked Alginate and GelMA constructs, wherein a significant effect of the interaction of bioink type and frequency ($p<0.0001$) was noted. The selected UAB parameters resulted in constructs with hASC viability of at least 80%, which is relevant for tissue engineering applications.

Figure 19:
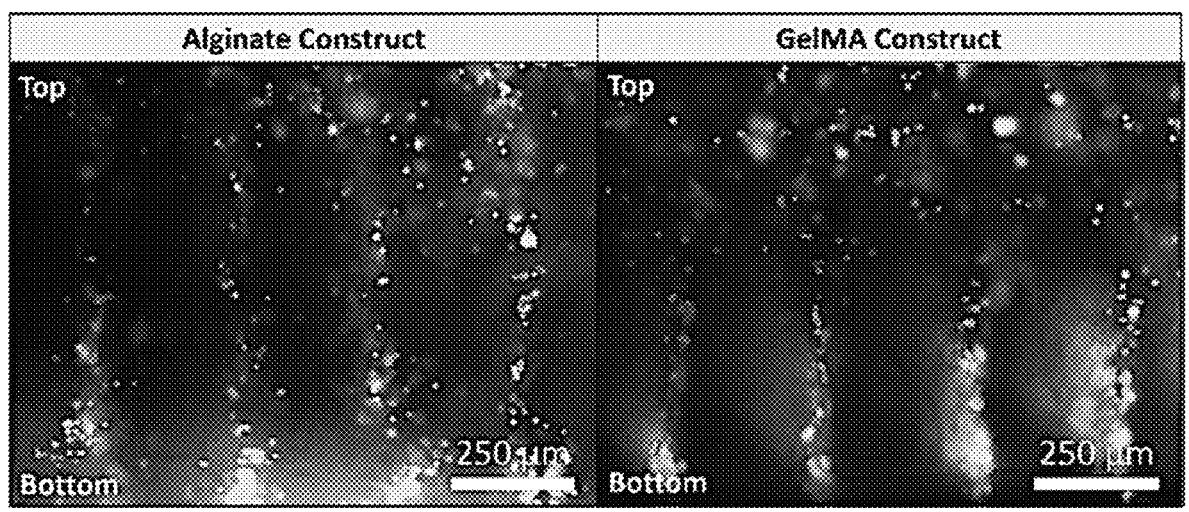
FIG. 19 illustrates representative Live/Dead® images of the side views (x-z cut plane) of the alginate and GelMA constructs at 2 MHz, as provided in accordance with some embodiments of the presently disclosed subject matter.

FIG. 19 illustrates representative Live/Dead® images of the side views (x-z cut plane) of the alginate and GelMA constructs at 2 MHz. The alignment characteristics of the alginate and GelMA constructs are commensurate with the computational model, wherein a higher density of cell alignment within the arrays was evident near the substrate. The alignment characteristics at other frequencies were similar.

Figure 20A:
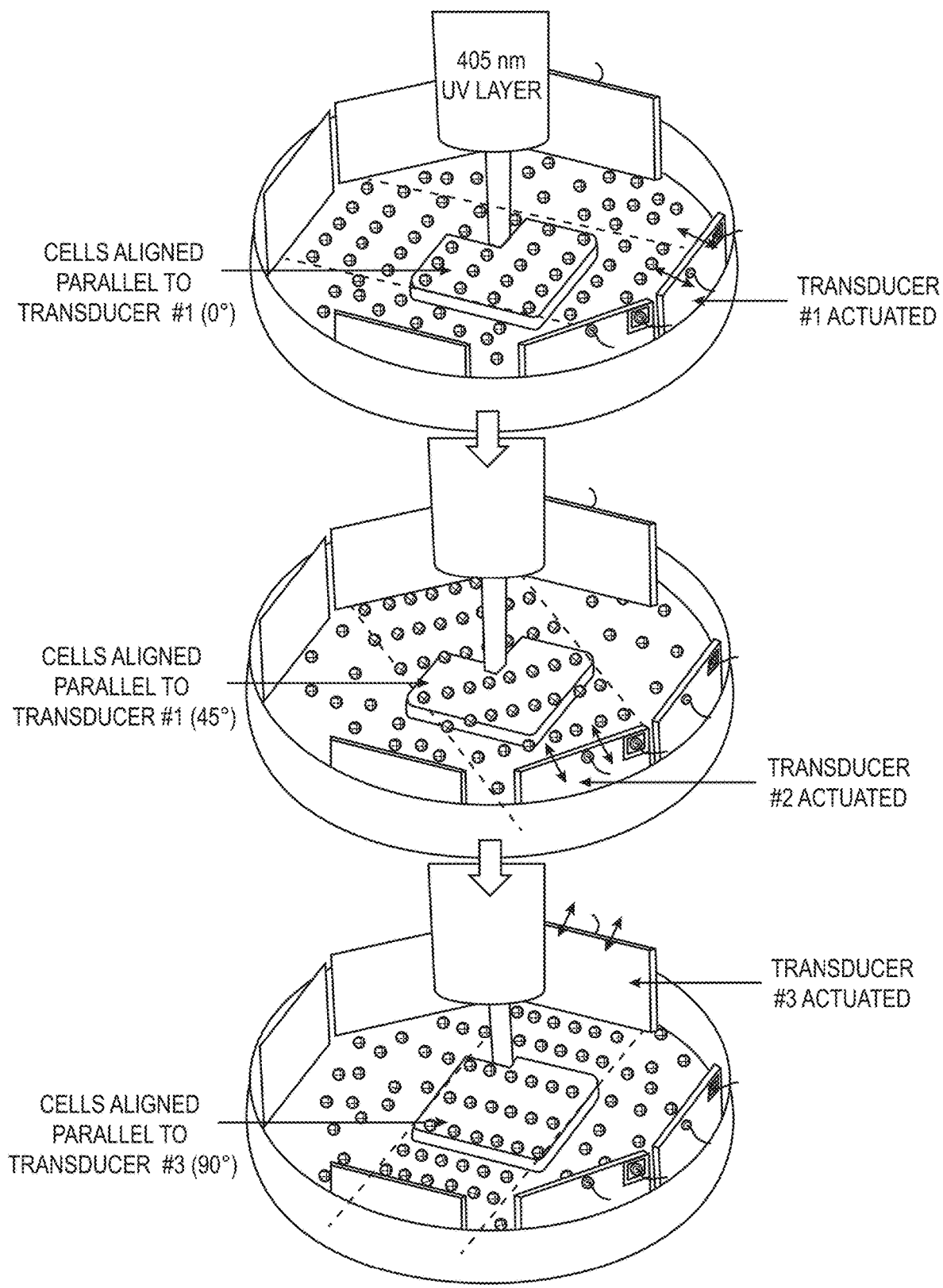
FIG. 20a illustrates vat photo-polymerization based UAB of 3 layered GelMA construct with 0°-45°-90° cell orientation, as provided in accordance with some embodiments of the presently disclosed subject matter. Specifically, a top portion of FIG. 20a illustrates the vat photo-polymerization based UAB of 3 layered GelMA construct with 0° cell orientation; a middle portion of FIG. 20(a) illustrates the vat photo-polymerization based UAB of 3 layered GelMA construct with 45° cell orientation; and, a bottom portion of FIG. 20a illustrates the vat photo-polymerization based UAB of 3 layered GelMA construct with 90° cell orientation.
Figure 20B:
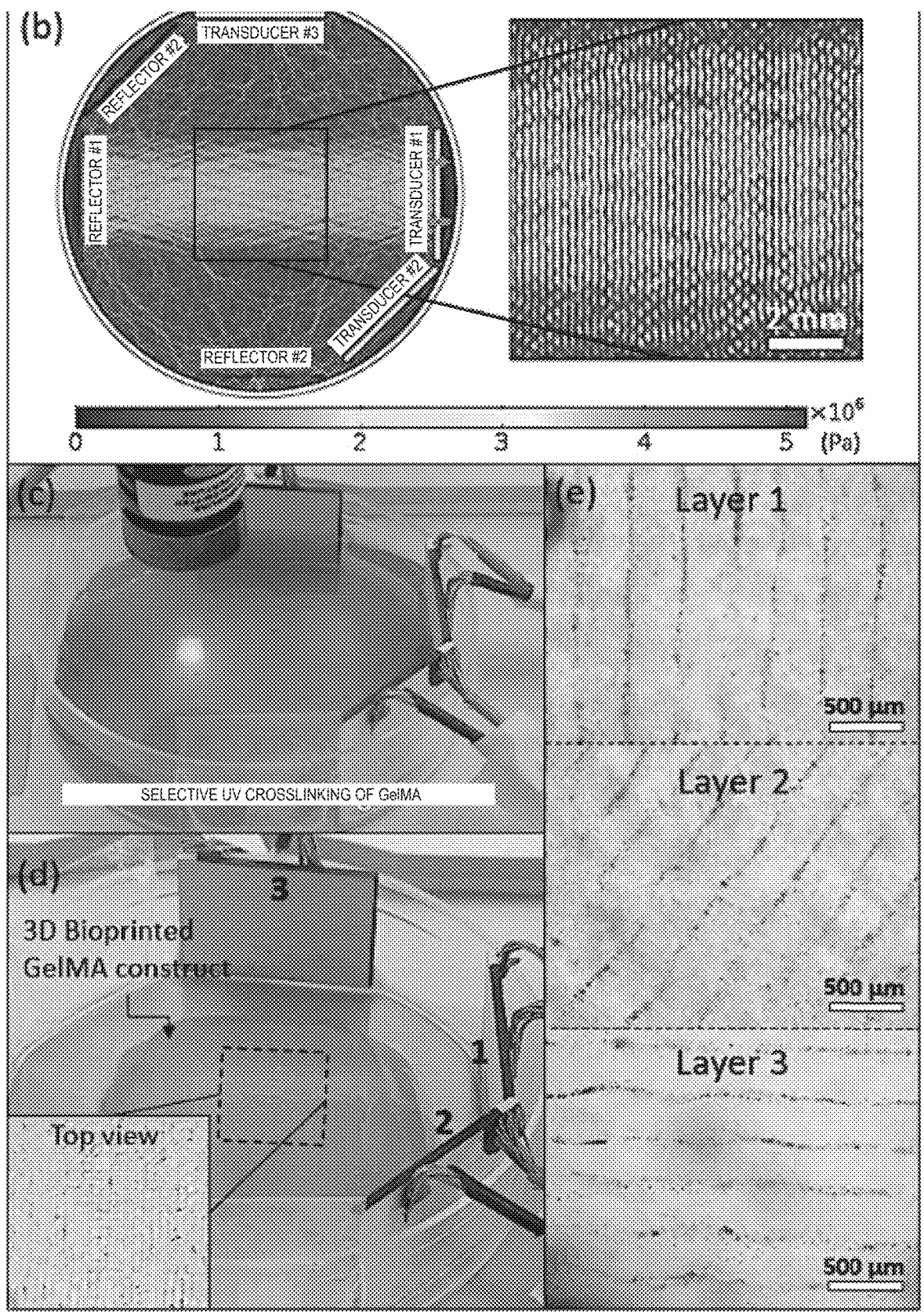
FIG. 20b illustrates an acoustic pressure distribution for a first layer of bioink within an ultrasonic alignment fixture (UAF) as seen from the top, which depicts nodal lines parallel to the actuated transducer with pressure distribution in layers 2 and 3 depicting nodal lines parallel to transducer 2 and 3, as provided in accordance with some embodiments of the presently disclosed subject matter. Specifically, a top portion of FIG. 20b (i.e., the portion marked (b)) illustrates the UAF as seen from the top and a magnified inset at scale bar=2 mm; a left middle portion of FIG. 20b (i.e., the portion marked (c)) illustrates a perspective view of the UAF showing selective UV crosslinking of GelMA; a left bottom portion of FIG. 20b (i.e., the portion marked (d)) illustrates a perspective view of a 3D bioprinted GelMA construct and a magnified inset of a top view of the 3D bioprinted GelMA construct; and, a lower right portion of FIG. 20b (i.e., the portion marked (e)) illustrates top views of Layer 1, Layer 2 and Layer 3 at scale bar=500 µm.

FIG. 20 accordingly illustrates 3D bioprinting of 3 layered GelMA construct with 0°-45°-90° cell orientation. FIG. 20(a) illustrates the actuation of transducer #1 after deposition of first layer of bioink orients the cells along the horizontally (0°: parallel to x-axis). Subsequent crosslinking using the UV laser crosslinks the GelMA solution into a hydrogel with entrapped cells in the 0° orientation. Similarly, deposition of layers 2 and 3 and associated transducer actuation and photopolymerization entraps the cells in 45° (45° relative to x-axis) and 90° (parallel to z-axis) orientation across the two layers. FIG. 20(b) illustrates acoustic pressure distribution for the first layer of bioink within the UAF as seen from the top, which depicts nodal lines parallel to the actuated transducer. Pressure distribution in layers 2 and 3 depicts nodal lines parallel to transducer 2 and 3. FIG. 20(c) illustrates selective ultraviolet (UV) crosslinking to create the bioprinted GelMA construct in FIG. 20 (d). The inset in the top view depicts the overlapping cell orientations (e) Microscopic brightfield images depicting 0°-45°-90° alignment pattern across layers 1-3, respectively. In both alginate and GelMA constructs, the cell density in the aligned arrays can be noted to be higher in the bottom regions, closer to the substrate. This was found to be in agreement with results of the computational model, wherein the radiation pressure diminishes towards the top of the constructs due to the air-water interface. Nevertheless, the overall alignment pattern depicts cellular strands as parallel planes, which may be difficult to achieve in a SSAW-based patterning that uses substrate vibrations to achieve cellular alignment.

The inventors have elucidated select process-structure function interrelationships that govern the alignment characteristics of multiple cell types within two types of viscous bioinks. Other functional characteristics of cells (e.g., phenotype, ECM formation, gene expression) in culture over time can also be assessed by the methods disclosed herein. For such longer term in vitro culture studies, especially for alginate, peptide modifications of its polymeric chains may be necessary to stimulate more favorable cellular responses. In general, using a higher viscosity bioink would necessitate the re-optimization of process parameters and crosslinking protocol to entrap the cellular patterns within the construct. In this case, while using higher voltage amplitudes would increase the pressure amplitude, thereby increasing the ARF to achieve quicker alignment, this could adversely affect the cell viability. At the same time, greater straining of the transducer at higher voltage amplitudes could also induce undesired turbulence due to acoustic streaming and distort the cell alignment. The inventors have identified that use of lower voltages coupled with a slower crosslinking protocol is advantageous to alleviate the streaming issue while achieving three-dimensional cellular alignment and higher viability. In general, altering the voltage amplitude would not affect the spacing between adjacent cellular strands, as this is dependent only on the applied ultrasound wavelength. However, changes in bioink viscosity might alter the spacing due to different speed of sound at the same frequency. As such, a proper optimization of the material and process parameters is required to achieve high fidelity of cellular alignment and high cell viability in the bioprinted constructs relevant to the tissue application.

Various embodiments disclosed herein include the integration of the SBAW-assisted alignment approach with bioprinting processes based on extrusion and vat photopolymerization principles. While other fundamentally different techniques for cell patterning such as electrophoresis, magnetophoresis, photophoresis or chemotaxis exist, unlike the label-free and contact-less approach of SBAW-assisted cell manipulation, these techniques require chemical or magnetic labeling, or complex and expensive apparatus which may not be integrable with bioprinting. Moreover, the fundamental mechanics to get parallel bands of cells within the entirety of the viscous bioinks would be very complex to model with these techniques, whereas the mechanics of SBAW-assisted cell alignment are straightforward and can provide repeatable results.

The methods disclosed herein can allow for the optimization of cell concentrations, strand width and inter-strand spacing, layer-wise alignment orientations and UAB parameters to achieve appropriate ECM responses and biomechanical properties using tissue-specific cells to develop various important tissues including ligaments, tendons and the knee meniscus. The capabilities of a process that uses ultrasonic SBAW to align multiple cell types within multiple types of bioinks have been disclosed herein. The process can take place within a custom-made UAF consisting of opposing transducer-reflector pairs, wherein the transducer vibration at ultrasonic frequencies creates the SBAW. The 3D computational model highlighted the acoustic pressure variations in the UAF as a pattern consisting of parallel nodal planes with greater pressure amplitudes near the bottom of the bioink layer. Experimental studies demonstrated cellular alignment along straight strands at the pressure nodal planes, with greater degree of cell alignment near the bottom of the constructs, which is in accordance with the computational model outcomes. The spacing between adjacent cell strands was governed only by the frequency and not the cell type, highlighting that repeatable alignment patterns can be created by just altering the frequency. The strand width was dependent on the transducer frequency and cell type, and the experimental values were in agreement with the corresponding analytical and computational estimates.

Embodiments disclosed herein demonstrate the successful bioprinting of aligned constructs with two bioinks possessing different crosslinking mechanisms. The resultant cell viability was found to be at least 80%, which further highlights the adequacy of this process for tissue engineering applications. The inventors successfully fabricated a 3-layered GelMA construct with 0-45-90° cell orientation in each layer, thereby asserting the flexibility of this approach to fabricate complex cellular architectures. Embodiments disclosed herein allow for the comprehensive characterization of cellular responses and ECM formation and biomechanical properties of constructs after maturation under appropriate culture conditions. Embodiments disclosed herein can further allow for the optimization of the bioinks and UAB process to create more complex alignment patterns using tissue-specific cells for targeted tissue engineering applications.

Figure 21:
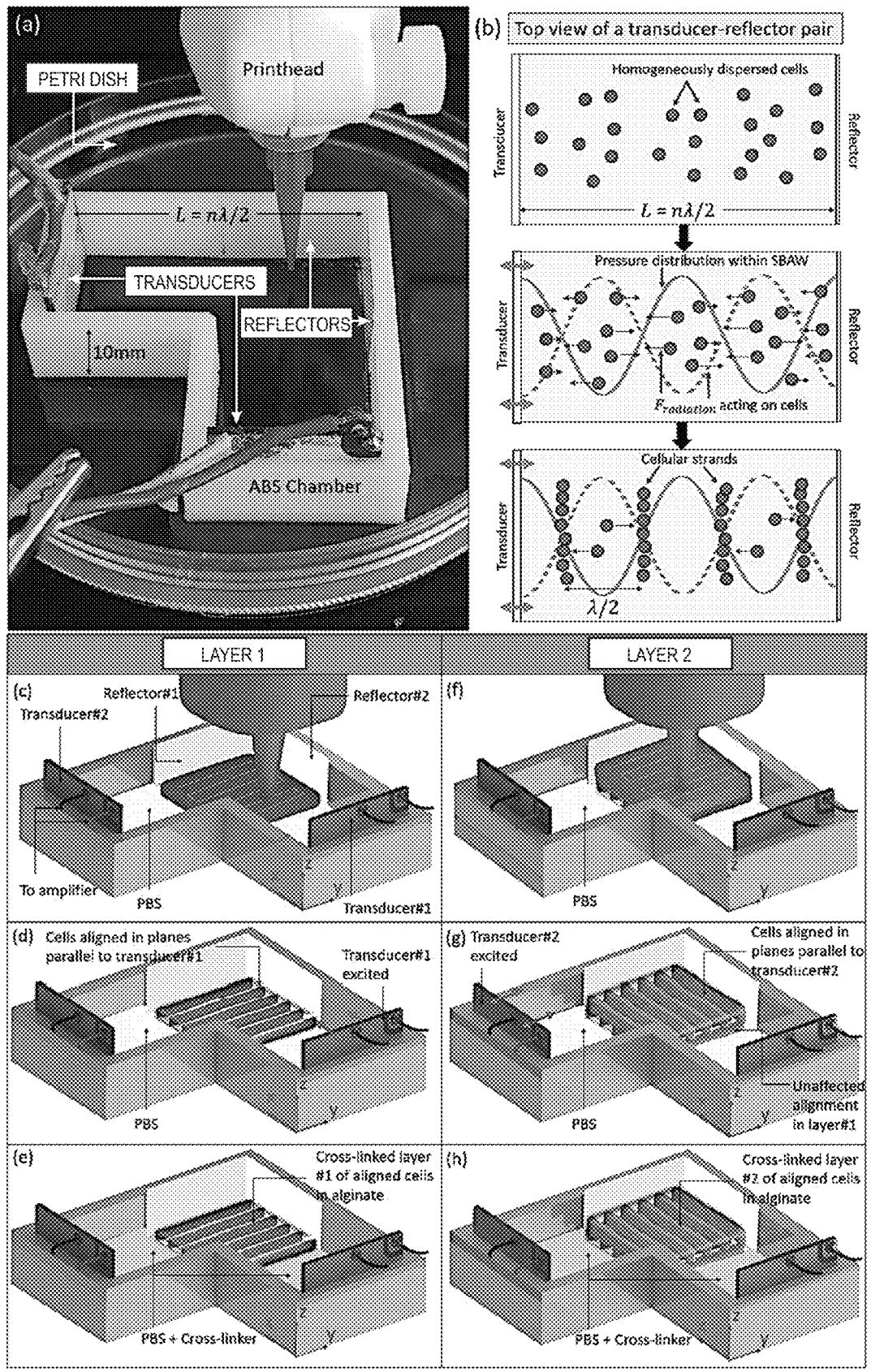
FIG. 21(1) illustrates the second layer of bioink is printed on top of the crosslinked first layer.
Figure 22:
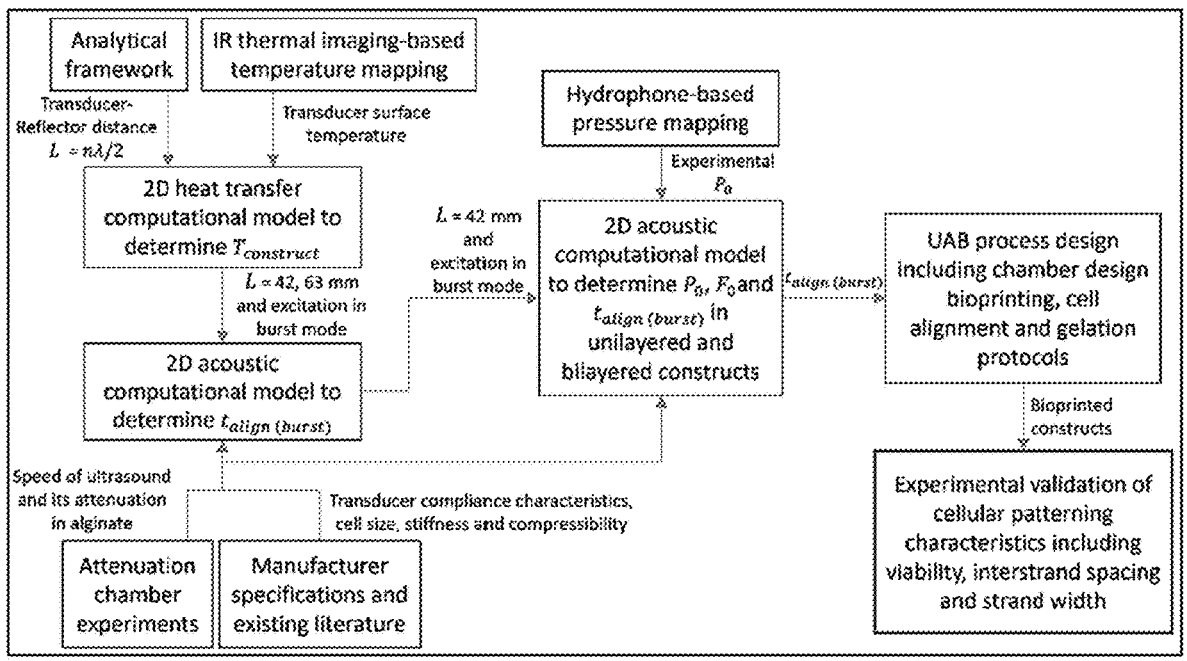
FIG. 22 illustrates a roadmap of the constitutive studies to investigate the process physics of ultrasound-assisted bioprinting and the characteristics of bioprinted constructs, as provided in accordance with some embodiments of the presently disclosed subject matter.

FIGS. 21 and 22 illustrate additional aspects of the presently disclosed subject matter.

FIG. 21(a) illustrates the cross-patterning ultrasound alignment chamber that contains orthogonally arranged transducer-reflector pairs. FIG. 21(b) illustrates a schematic representation of the SBAW generated due to transducer excitation, and the resulting acoustic pressure distribution which exerts $F_{radiation}$ on the cells to align them at the pressure nodes of the SBAW. FIG. 21(c) illustrates the bioink being printed as adjacent strands (blue lines depict that rectilinear pattern of deposition) into the chamber pre-filled with PBS buffer to constitute the first layer of the construct. It can be seen that the MG63 are homogeneously distributed across this layer. FIG. 21(d) illustrates transducer #1, when excited using a sinusoidal voltage signal, vibrating along its thickness (along x-axis) to align the cells along nodal planes parallel to the transducer surface (y-z plane). FIG. 21(e) illustrates the alginate being gradually crosslinked by introducing the crosslinker ($CaCl_2$) to entrap the aligned cells within the first layer. FIG. 21(f) illustrates the second layer of bioink being printed on top of the crosslinked first layer after aspirating all the fluid (PBS+$CaCl_2$) in the chamber and adding fresh PBS. FIG. 21(g) illustrates transducer #2, when excited using a sinusoidal voltage signal, vibrating along its thickness (along y-axis) to impart an orthogonal cellular alignment (x-z plane) relative to the first layer (0°-90° alignment). FIG. 21(h) illustrates the crosslinker ($CaCl_2$) being introduced to gradually crosslink the second alginate layer while entrapping the aligned cells.

FIG. 22 illustrates a roadmap of the constitutive studies to investigate the process physics of ultrasound-assisted bioprinting and the characteristics of bioprinted constructs.

FIGS. 23 and 24 illustrate additional aspects of the presently disclosed subject matter.

Figure 23A:
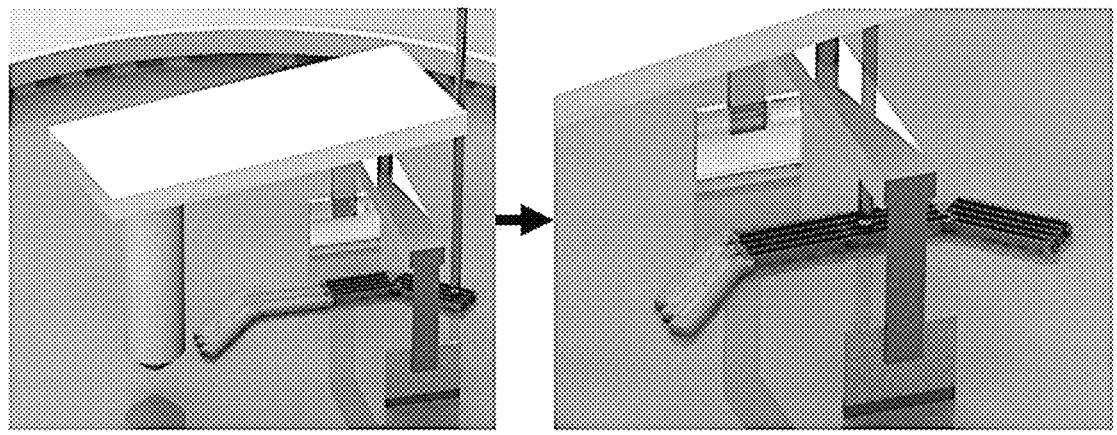
FIG. 23a illustrates a perspective view of a printhead dispensing the bioink into the chamber with the transducers or transducer-reflector pair following behind on the path along which bioink that has been already deposited; and, FIG. 23b illustrates a close-up of the printhead, as provided in accordance with some embodiments of the presently disclosed subject matter.
Figure 23B:
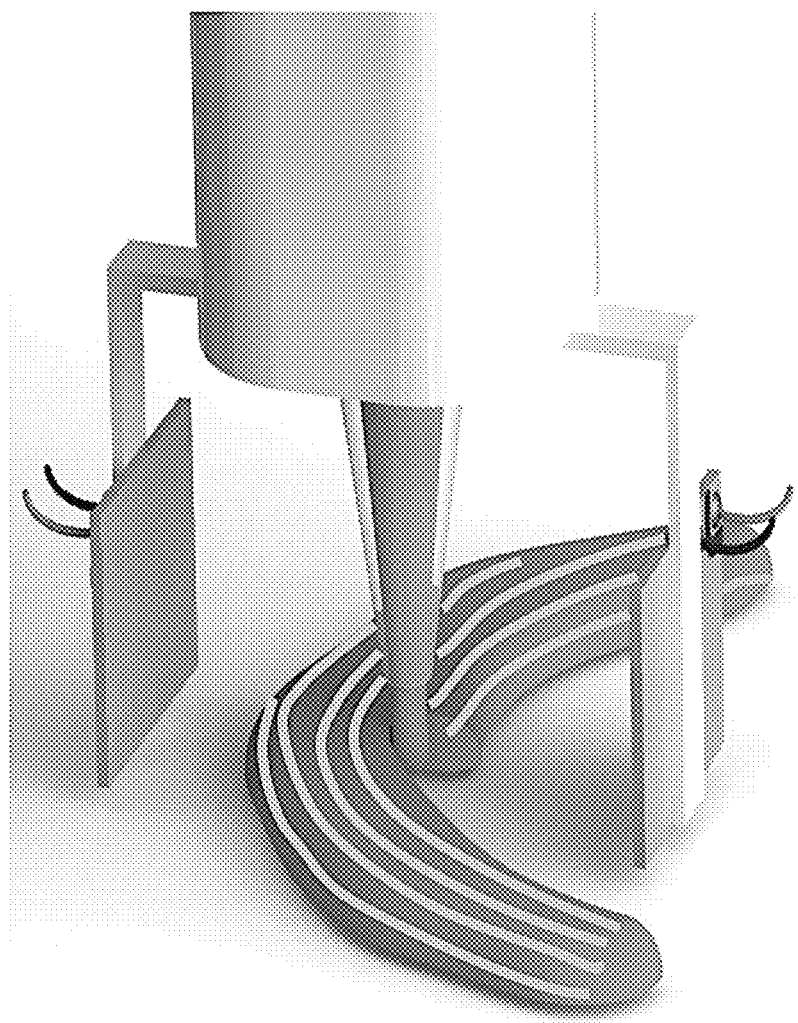

FIG. 23a illustrates a perspective view of a printhead dispensing the bioink into the chamber. The transducers or transducer-reflector pair follows behind on the path along which bioink that has been already deposited; and, FIG. 23b illustrates a close-up of the printhead. Printhead dispenses the bioink into the chamber. The transducers or transducer-reflector pair follows behind on the path along which bioink that has been already deposited. The SBAW inducted between the transducers/transducer-reflector pair align the cells or particles along the nodes or nodal planes, parallel to the surface of the transducer. Aligned particles are entrapped when the fluid matrix is crosslinked; the beam represents heat/light/chemical based crosslinking mechanisms. The transducers follow the dispensing head and continue aligning the particles, with the crosslinking of previously aligned matrix occurring in parallel. The orientation of the transducers can keep changing to accommodate new alignment pattern of particles. Multiple layers can be created as the apparatus is movable in Z-axis. The distance between transducers can be varied to accommodate the size of the construct. The orientation of particles in previously cross-linked layers is not affected by the new orientation of the transducers.

Figure 24A:
FIG. 24a illustrates collagen bundles after centrifugation obtained from experiments with acellular constructs showing aligned collagen bundles in GelMA.
Figure 24B:
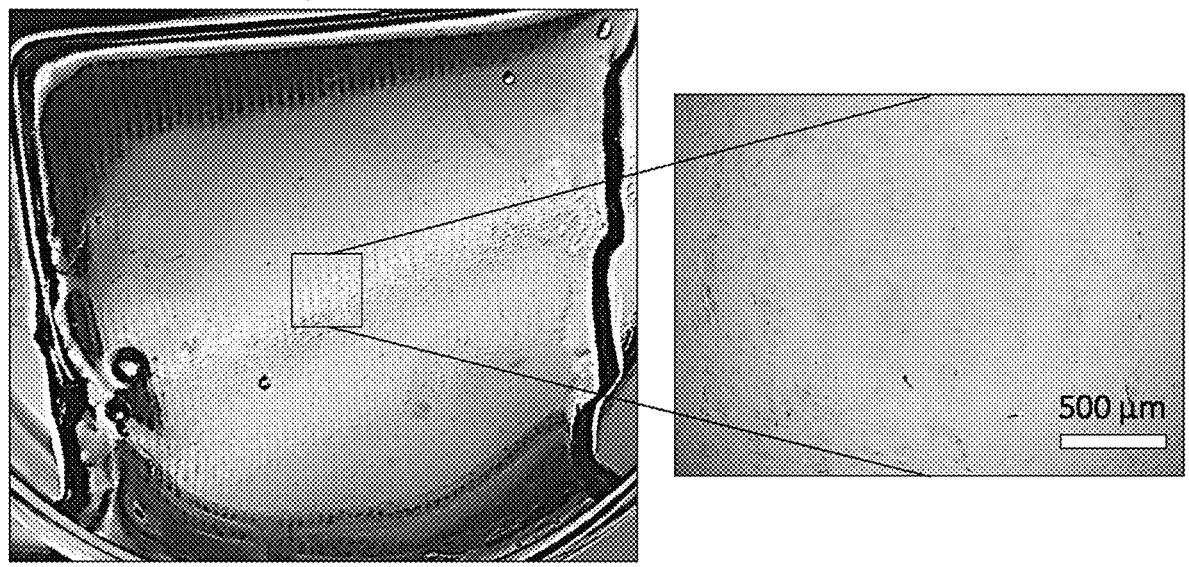
FIG. 24b illustrates GelMA constructs with aligned cells and collagen bundles obtained from experiments with acellular constructs showing aligned collagen bundles in GelMA.
Figure 24C:
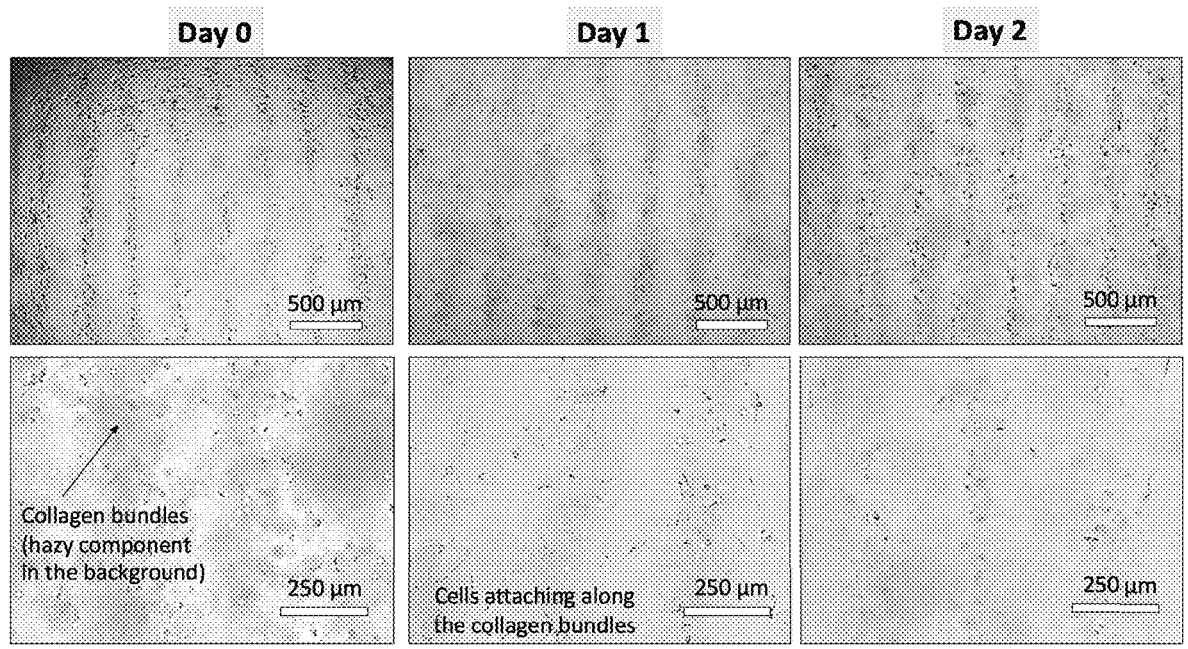
FIG. 24c illustrates aligned cells and collagen bundles in GelMA from day 0 through day 2 of an experiment with aligned cells and collagen bundles in GelMA; and, FIG. 24d illustrates aligned cells and collagen bundles in GelMA on day 3 of the experiment with aligned cells and collagen bundles in GelMA, as provided in accordance with some embodiments of the presently disclosed subject matter.
Figure 24D:
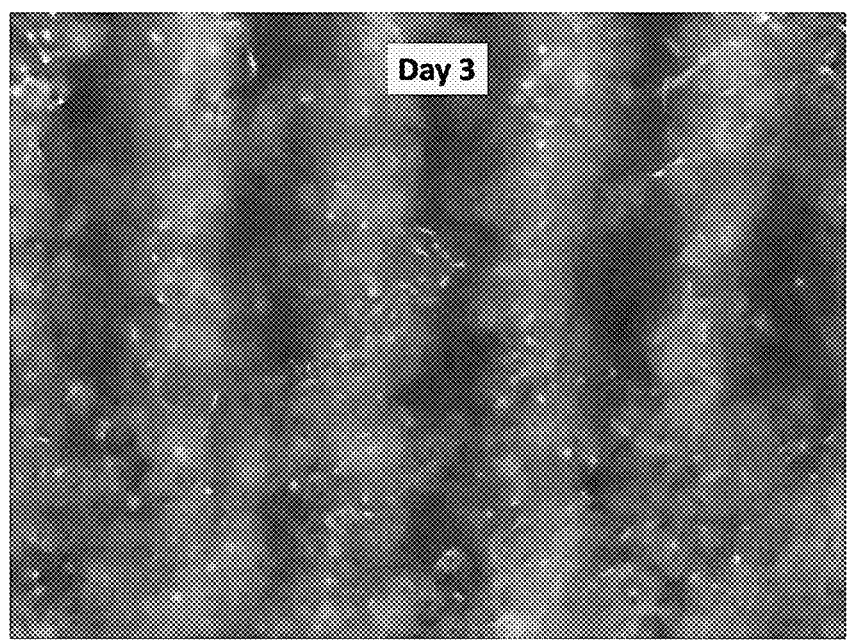

FIG. 24a illustrates collagen bundles (average diameter 30 um) after centrifugation forming part of experiments with acellular constructs showing aligned collagen bundles in GelMA; FIG. 24b illustrates GelMA constructs with aligned cells and collagen bundles forming part of experiments with acellular constructs showing aligned collagen bundles in GelMA; FIG. 24c illustrates aligned cells and collagen bundles in GelMA from day 0 through day 2 of an experiment with aligned cells and collagen bundles in GelMA; and, FIG. 24d illustrates aligned cells and collagen bundles in GelMA on day 3 of the experiment with aligned cells and collagen bundles in GelMA.

It is to be noted that since the viscosity of crosslinked alginate is several orders of magnitude higher than its uncrosslinked solution counterpart, the alignment of cells entrapped within the crosslinked first layer is not affected by transducer excitation during printing and alignment of the subsequent layer. It should be noted that to achieve parallel alignment (0°-0°) across layers, either transducer #1 or transducer #2 can be excited after depositing each layer.

Whereas the description discusses depositing a bioink fluid matrix containing a suspension of cells or particles into a chamber, bioink fluid matrix can contain various substances including proteins, micro particles, nano-particles, micro-fibers, nano-fibers, and similar other items.

As to the above, they are merely specific embodiments of the present invention; however, the scope of protection of the present invention is not limited thereto, and within the disclosed technical scope of the present invention, any modifications or substitutions that a person skilled in the art could readily conceive of should fall within the scope of protection of the present invention. Thus, the scope of protection of the present invention shall be determined by the scope of protection of the appended claims.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

These and other changes can be made to the disclosure in light of the Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

What is claimed is:

1. A method of ultrasound-assisted three-dimensional (3D) bioprinting, the method comprising:
    depositing a bioink fluid matrix containing a suspension of cells or particles into a chamber comprising a 3D-printing head, and a piezo transducer and a reflector positioned on opposing ends of the chamber;
    vibrating the piezo transducer to generate longitudinal bulk acoustic waves within the bioink fluid matrix such that waves emanating from the piezo transducer and reflected waves from the reflector superimpose to form a standing bulk acoustic wave; and
    driving the cells or particles to cluster and align the cells or particles along one or more nodes or nodal planes formed within the bioink fluid matrix at points of intersection of the standing bulk acoustic wave to form a construct, wherein:
    the nodal planes are spaced apart from each other by a distance equaling half a wavelength of the standing bulk acoustic wave,
    the nodes or nodal planes mimic a contour of vibrating surfaces of the piezo transducer or the reflector, or organize a pattern determined using computational modeling, and
    the 3D-printing head comprises an apparatus for gelling or solidifying the suspension of cells or particles.

2. The method of claim 1, further comprising solidifying the bioink fluid matrix using one or more of: chemical, heat, and light treatment to entrap the aligned cells or particles in place.

3. The method of claim 1, further comprising gelling the bioink fluid matrix using one or more of: chemical, heat, and light treatment to entrap the aligned cells or particles in place.

4. The method of claim 1, wherein a chamber shape and a number of piezo transducers is configured based on a predetermined pattern of cell arrangement.

5. The method of claim 1, further comprising providing additional piezo transducers wherein a control algorithm vibrates the piezo transducers in a specified sequence to obtain a predetermined pattern of cell arrangement.

6. The method of claim 1, wherein spacing between the piezo transducer and the reflector is equal to an integer multiple of half the wavelength of the standing bulk acoustic wave.

7. The method of claim 1, wherein spacing between the piezo transducer and the reflector is correlated to a frequency of the standing bulk acoustic wave.

8. The method of claim 1, further comprising one or more of: increasing a frequency of the standing bulk acoustic wave to decrease a width of the nodal planes; increasing a voltage amplitude supplied to the piezo transducer to decrease a width of the nodes or nodal planes; increasing excitation duration or actuation duration of the piezo transducer to decrease a width of the nodes or nodal planes; delaying a crosslinking initiation or a gelling initiation within the chamber to reduce a width of the nodes or nodal planes; and increasing a frequency of the standing bulk acoustic wave to decrease spacing between adjacent nodal planes.

9. The method of claim 1, wherein the piezo transducer is electrically coupled to an intermediate high frequency radio frequency power amplifier.

10. The method of claim 1, wherein the piezo transducer is electrically coupled to one or more of a function generator and a signal generator.

11. The method of claim 1, further comprising crosslinking the aligned cells or particles nodes or nodal planes by one or more of a gelling process and a solidifying process.

12. The method of claim 1, wherein the bioink fluid matrix is a homogenous suspension of one or more of: cells, proteins, micro particles, nano-particles, micro-fibers and nano-fibers.

13. The method of claim 1, further comprising:
    transferring the chamber comprising a completed construct with aligned cells or particles to an incubator; and
    maturing the construct, using the incubator, over a predetermined time period under predetermined environmental conditions.

14. The method of claim 1, wherein the 3D-printing head further comprises a dispenser of the bioink fluid matrix.

15. The method of claim 1, wherein the 3D-printing head further comprises an apparatus for orienting the piezo transducers.

16. A method of ultrasound-assisted three-dimensional (3D) bioprinting, the method comprising:
    depositing a bioink fluid matrix containing a suspension of cells or particles into a chamber, the chamber comprising a 3D-printing head and two piezo transducers on opposing ends of the chamber;
    vibrating the piezo transducers to generate longitudinal bulk acoustic waves within the bioink fluid matrix such that waves from opposing piezo transducers superimpose to form a standing bulk acoustic wave; and
    driving the cells or particles to cluster and align along one or more nodes or nodal planes formed within the bioink fluid matrix at points of intersection of the standing bulk acoustic wave to form a construct,
    wherein the nodes or nodal planes are spaced apart from each other by a distance equaling half a wavelength of the standing bulk acoustic wave,
    wherein the nodes mimic a contour of vibrating surfaces of the piezo transducers, or a pattern determined using computational modeling, and
    the 3D-printing head comprises an apparatus for gelling or solidifying the suspension of cells or particles.

17. The method of claim 16, wherein spacing between the piezo transducers is equal to an integer multiple of half the wavelength of the standing bulk acoustic wave.

18. The method of claim 16, further comprising:
transferring the chamber comprising a completed construct with aligned cells or particles to an incubator; and
maturing the construct, using the incubator, over a predetermined time period under predetermined environmental conditions.

19. The method of claim 15, wherein the cells or particles comprise one or more of: proteins, micro particles, nanoparticles, micro-fibers and nano-fibers.

20. A method of ultrasound-assisted three-dimensional (3D) bioprinting, the method comprising:
depositing a bioink fluid matrix containing a suspension of cells into a chamber comprising a 3D-printing head, and a piezo transducer and a reflector positioned on opposing ends of the chamber;
vibrating the piezo transducer to generate longitudinal bulk acoustic waves within the bioink fluid matrix such that waves emanating from the piezo transducer and reflected waves from the reflector superimpose to form a standing bulk acoustic wave; and
driving the cells to cluster and align along one or more nodes or nodal planes formed within the bioink fluid matrix at points of intersection of the standing bulk acoustic wave to form a construct,
wherein the nodal planes are spaced apart from each other by a distance equaling half a wavelength of the standing bulk acoustic wave,
wherein the nodes or nodal planes mimic a contour of vibrating surfaces of the piezo transducer or the reflector, or organize a pattern determined using computational modeling, and
the 3D-printing head comprises an apparatus for gelling or solidifying the suspension of cells or particles.

21. The method of claim 20, further comprising:
transferring the chamber comprising a completed construct with aligned cells to an incubator; and
maturing the construct, using the incubator, over a predetermined time period under predetermined culture conditions.

* * * * *